(12) United States Patent
Moyle

(10) Patent No.: US 6,486,303 B1
(45) Date of Patent: Nov. 26, 2002

(54) METHOD FOR MAKING HORMONE HETERODIMERS

(75) Inventor: William R. Moyle, Piscataway, NJ (US)

(73) Assignee: University of Medicine & Dentistry of New Jersey, New Brunswick, NJ (US)

(*) Notice: Subject to any disclaimer, the term of this patent is extended or adjusted under 35 U.S.C. 154(b) by 0 days.

(21) Appl. No.: 09/059,625

(22) Filed: Apr. 14, 1998

(51) Int. Cl.$^7$ .................. C07K 14/59; C07K 17/00; C12P 21/02
(52) U.S. Cl. ............. 530/387.3; 530/395; 530/397; 530/398; 530/388.22; 435/69.7; 435/69.4
(58) Field of Search .................. 530/387.3, 395, 530/397, 398, 388–22; 435/69.7, 69.4

(56) References Cited

FOREIGN PATENT DOCUMENTS

WO    WO 91/16922    * 11/1991

OTHER PUBLICATIONS

Mohamed et al. Steroid Biochemistry and Molecular Biology, vol. 51, No. 5/6, pp. 241–250, 1994.*

* cited by examiner

*Primary Examiner*—Yvonne Eyler
*Assistant Examiner*—Fozia Hamud
(74) *Attorney, Agent, or Firm*—Michael J. Wise

(57) ABSTRACT

The present invention relates to a method for preparing heterodimeric analogs of cysteine knot proteins. More specifically, the invention relates to a method for forming a subunit combination of a cysteine knot protein having an α-subunit and a β-subunit to prepare a heterodimeric protein analog which comprises the steps of (a) attaching a dimerization domain to the amino termini of both an α-subunit and β-subunit of a cysteine knot protein; and (b) dimerizing the α-subunit and β-subunit to form a heterodimeric protein analog. In another embodiment, the invention relates to a method for forming a subunit combination of a cysteine knot protein having an α-subunit and a β-subunit to prepare a heterodimeric protein analog which comprises the steps of (a) attaching a dimerization domain to the amino terminus of an α-subunit and the carboxy terminus of a β-subunit of a cysteine knot protein; and (b) dimerizing the α-subunit and β-subunit to form a heterodimeric protein analog.

18 Claims, 21 Drawing Sheets

Figure 1

```
                                                                          -10
                             M  E  M  F  Q  G  L  L  L  L  L  L  L  S  M  G  G  T  W
5'-CTCGAGTCTAGACCCAGCTTAGACAAGGACGCACCAAGGCAGGGGACGATGGAGATGTTCCAGGGGCTGCTGCTGCTGTTGCTGTGCTGAGCATGGGCGGGACATGG-3'
3'-GAGCTCAGATCTGGGTCGAATCTGTTCCGTCCGTGGTTCCTACCTCTACAAGGTCCCCGACGACGACAACGACGACGACGACAACGACTCGTACCCGCCCTGTACC-5'
    XhoI   XbaI
                                         -1  1                   10                            20
                                          A  S  C  R  P  I  N  A  T  L  A  V  E  K  E  G  C  P  V  C  I
5'-GCTAGCTGCCGCCCCATCAATGCCACCCTGGCTGTGGAGAAGGAGGGCTGCCCCGTGTGCATCAACACCACCATCTGTGCCGGCTACTGCCCCACC-3'
3'-CGATCGACGGCGGGGTAGTTACGGTGGGACCGACACCTCTTCCTCCCGACGGGGCACACGTAGTTGTGGTGGTAGACACGGCCGATGACGGGGTGG-5'
    NheI
                 30                                 40
  T  V  N  T  T  I  C  A  G  Y  C  P  T

M  T  R  V  L  Q  G  V  L  P  A  L  P  Q  V  V  C  N  Y  R  D  V  R  F  E  S  I  R  L  P  G  C  P  R
5'-ATGACCCGCGTGCTGCAGGGCGTCCTGCCTGCCCTGCCTCAGGTGGTGTGCAACTATCGCGATGTGCGCTTCGAGTCCATCCGGCTCCCTGCTGCCCCGCGC-3'
3'-TACTGGGCGCACGACGTCCCGCAGGACGGACGGGACGGAGTCCACCACACGTTGATAGCGCTACACGCGAAGCTCAGGTAGCCGAGGACGACGGGGCGCG-5'
                 50                                 60                                 70
                                      80                                 90                                 100
  G  V  N  P  V  V  S  Y  A  V  A  L  S  C  Q  C  A  L  C  R  R  S  T  T  D  C  G  G  P  K  D  H  P  L
5'-GGGGTGAACCCCGTGGTCTCCTACGCCGTGGCTCTCAGCTGTCAATGTGCACTCTGCCGCCGCAGCACCACTGACTGCGGGGGTCCCAAGGACCACCCCTTG-3'
3'-CCCGCACTTGGGGCACCAGAGGATGCGGCACCAGAGTCGACAGTTACACGTGAGAGCGGCGTCGTGGTGACTGACGCCCCCAGGGTTCCTGGTGGGGAAC-5'
                                      110                                120                                130
  T  C  D  D  P  R  F  Q  D  S  S  S  K  A  P  P  P  S  L  P  S  P  S  R  L  P  G  P  S  D  T  P  I
5'-ACCTGTGATGACCCCCGCTTCCAGGACTCCTCTTCCTCAAAGGCCCCTCCCCCCAGCCTCCCAAGCCCATCCCGACTCCCGGGCCCCTCCGACACCCCGATC-3'
3'-TGGACACTACTGGGGGCGAAGGTCCTGAGGAGAAGGAGTTTCCGGGGAGGGGGTCGGAGGGTTCGGAGGGTTCGGGATAGGGCTGAGGGCCCCGGGGAGGCTGTGGGGCTAG-5'
            140
  L  P  Q  *
      145
5'-CTCCCACAATAAAGGCTTCTCAATCCGCAAGCTGGGAGCTCGACCCGCGGAGCTCGGATCC-3'
3'-GAGGGTGTTATTTCCGAAGAGTTAGGCGTTCGACCCTCGAGCCTGGGCGCCTCGAGCCTAGG-5'
                                                    SstI    BamHI
```

Figure 2

```
                                              M  E  M  F  Q  G  L  L  L  L  L  L  L  S  M  G  G  T  W
                                                                    -10
5'-CTCGAGTCTAGACCCAGCTTAGACAAGGCAGGGGACGCACCAAGGATGGAGATGTTCCAGGGGCTGCTGCTGTTGCTGCTGCTGAGCATGGGCGGGACATGG-3'
3'-GAGCTCAGATCTGGGTCGAATCTGTTCCGTCCCCTGCGTGGTTCCTACCTCTACAAGGTCCCCGACGACGACAACGACGACGACTCGTACCCGCCCTGTACC-5'
   XhoI    XbaI

-1  1                       10                            20                           30
        A  S  C  G  G  L  T  D  T  L  Q  A  E  T  D  Q  L  E  D  K  K  S  A  L  Q  T  E  I  A  N  L  L  K  E
5'-GCTAGCTGTGGTGGGTTAACCGATACCCTGCAAGCTGAAACTGATCAACTGGAAGATAAGAAATCTGCTCTGCAAACTGAAATCGCTAATCTGCTGAAAGAG-3'
3'-CGATCGACACCACCCAATTGGCTATGGGACGTTCGACTTTGACTAGTTGACCTTCTATTCTTTAGACGAGACGTTTGACTTTAGCGATTAGACGACTTTCTC-5'
   NheI

K  E  K  L  E  F  I  L  A  G  Q  D  C  P  E  C  T  L  Q
                  40                           50
5'-AAGGAAAAGCTTGAGTTCATCCTGGCCGGCCAAGATTGTCCGGAATGCACGCTACAGGGATCC-5'
3'-TTCCTTTTCGAACTCAAGTAGGACCGGCCGGTTCTAACAGGCCTTACGTGCGATGTCCCTAGG-3'
   HindIII        NgoMI      BspEI BsmI        BamHI
```

Figure 3

```
                              -20                            -10
                 M  E  M  F  Q  G  L  L  L  L  L  L  L  S  M  G  G  T  W
5'-CTCGAGTCTAGACCAGCTTAGACAAGGCAGGGACGCACCAAGGATGGAGATGTTCCAGGGGCTGCTGCTGCTGCTGTTGCTGTGCTGAGCATGGGGGGACATGG-3'
3'-GAGCTCAGATCTGGGTCGAATCTGTTCCGTCCCTGCGTGGTTCCTACCTCTACAAGGTCCCCGACGACGACGACGACAACGACACGACTCGTACCCCCTGTACC-5'
   XhoI  XbaI

-1  1                        10                        20                        30
    A  S  C  G  G  R  I  A  R  L  E  E  K  V  K  T  L  K  A  Q  N  S  E  L  A  S  T  A  N  M  L  R  E  Q
5'-GCTAGCTGTGCGGCCGCATTGCTAGATTGGAAGAGAAAGTTAAAACTCTGAAGGCCCAAAACAGCGAACTGGCTTCCACTGCTAATATGCTGCGTGAACAA-3'
3'-CGATCGACACCGCCGGCGTAACGATCTAACCTTCTCTTTCAATTTTGAGACTTCCGGGTTTTGTCGCTTGACCGAAGGTGACGATTATACGACGCACTTGTT-5'
   NheI 40                        50
    V  A  Q  L  K  Q  K  V  M  G  L  R  P  R  C  L  S  R  *
5'-GTCGCTCAACTGAAGCAAAAGGTTATGGGGTTTGCGCCCTAGGTGCCTTAGCAGGTAAGGATCC-3'
3'-CAGCGAGTTGACTTCGTTTTCCAATACCCCAAACGCGGGATCCACGGAATCGTCCATTCCTAGG-5'
                                        AvrII    BspMI      BamHI
```

Figure 4

| Primer | Base Sequence |
|---|---|

```
#1004   5'-GAATTCGCTAGCTGTGGTGGGTTAACCGAT-
           ACCCTGCAAGCTGAAACTGAT-3'
#1002   5'-ACCCTGCAAGCTGAAACTGATCAACTGAAGATAAGAAATCTGCTCTGCAAACTGAAATCGCT-3'
#1003                                                3'-TAGACGAGACGTTTGACTTTAGCGATTAGACGACTTTCTCTTCCTTTCGAACTCAAG-5'
#1005                                                       3'-CTTTCTCTTCCTTTCGAACTCAAG-
                                                        TAGGACGGCCGGTTCTAACAGGCCCTTAGGTGCGATGTCCCTAGGCTTAAG-5'

#1008   5'-GAATTCGCTAGCTGTGGCGGCCGCATTGCT-
           AGATTGGAAGAGAGAAGTTAAAACT-3'
#1006   5'-AGATTGGAAGAGAGAAGTTAAAACTCTGAAGGCCCAAAACAGCGAACTGGCTTCCACTGCTAAT-3'
#1007                                                3'-CTTGACCGAAGGTGACGATTATACGACGCACTTGTTCAGGGAGTTGACTTCGTT-
                                                                                                   TTCCAA-5'
#1009                                                       3'-AGTTGACTTCGTT-
                                           TTCCAATACCCAAACGCGGGATCCACGGAATCGTCCATTCCTAGGCTTAAG-5'

#739    5'-GCGGCGGCCATATGTTACACCAACAACGAAACCAACAC-3'
#839    5'-TGCTTCTCTAGAGCATATCCAACTCCAATTGAGATCTAAGAAGACTCACTGTCCAAAAGCAAGTCACTAGTGAGTCCACTTGC-3'
#850    5'-CCATTGAGATCTAAGAAGACTATGTTGGTCCAAAAGCAAGTCACTAGTGAGTCCACTTGC-3'
#851    5'-ACAAGTACTGCAGTGACAAGCAGTGTGTTGCTCCACTTTGAAACC-3'
#1053   5'-AGCTTGAGTTCATCCTGCCGGCCAAGATGCT-3'
#1054   5'-CCGGAGCATCTTGGCCGGCCAGGATGAACTCA-3'
#845    5'-CCGGCTGTTGTCCTACCATGACACGTGCTGCA-3'
#874    5'-GCACACGTGTCATGGTAGGACAACAG-3'
#1026   5'-CTGCGTCCTAGGTGTCGTCCTATTAATGCTACTCTGGCTGTTGAGAAGGAAGGTTGTCCTGT-3'
#1027   5'-ACAATAGCGGCACAGATGGTAGTGTTAACAGTAATGCCACAGGACAACCTTCCTTCTCAAC-3'
#435    5'-GTGGCTCTCAGCTGTCAATGCGCGCTCTGCCGCAGATCTACCACTACTGACTCGCGGGTCCCTAAGGACCAC-3'
#436    5'-CCACACGGATCCGAGCTCTTAGCGGGGTCATCACAGGTCAAGGTGGTCCTTAGGGACCCCGCAGTCCAGT-3'
#837    5'-CGCGCTTTAAAG-3'
#838    5'-GATCCTTTAAAG-3'
```

Figure 5

```
                                                                            M   E   M   F   Q   G   L   L   L   L   L   L   S   M   G   G   T   W   A   S
5'-CTCGAGTCTAGACCAGCTTAGACAAGGCAGGGAGGACGCACCAAGGATGGAGATGTTCCAGGGCTGCTGTTGCTGCTGCTGTTGCTGAGCATGGGCGGGACATGGGCTAGC-3'
3'-GAGCTCAGATCTGGGTCGAATCTGTTCCGTCCGTCCCCTGCGGTTCCTACCTGGTGTTCCGAGACAACGACGACGACGACGACTCGTACCCGCCCCTGTACCGATCG-5'
                    XhoI   XbaI                                                                                                                   NheI

C   G   G   L   T   D   T   L   Q   A   E   T   D   Q   L   E   D   K   K   S   A   L   Q   T   E   I   A   N   L   L   K   E   K   L
5'-TGTGGTGGGTTAACCGATACCCTGCAAGCTGAAACTGATCAACTGGAAGATAAGAAATCTGCTCTGCAAACTGAAATCGCTAATCTGCTGAAAGAGAAAGCTT-3'
3'-ACACCACCCAATTGGCTATGGGACGTTCGACTTTGACTAGTTGACCTTCTATTCTTTAGACGAGACGTTTGACTTTAGCGATTAGACGACTTTCTCTTTCGAA-5'
                                                                                                                                HindIII E   F   I   L   A   G   Q   D   C   P   E   C   T   L   Q   E   N   P   F   F   S   Q   P   G   A   P   I   L   Q   C   M   G   C   C   F   S
5'-GAGTTCATCCTGGCCGGCCAAGATTGTCCGGAATGCACGCTACAGGAAAACCCATTCTTCTCCCAGCCGGGTGCCCAATACTTCAGTGCATGGGCTGCTGCTTCTCT-3'
3'-CTCAAGTAGGACCGGCCGGTTCTAACAGGCCTTACGTGCGATGTCCTTTTGGGTAAGAAGAGGGTCGGCCCACGGGTTATGAAGTCACGTACCCGACGACGAAGAGA-5'
                    NgoMI         BspEI   BsmI R   A   Y   P   T   P   L   R   S   K   K   T   M   L   V   Q   K   N   V   T   S   E   S   T   C   C   V   A   K   S   Y   N   R   V   T   V
5'-AGAGCATATCCCACTCCACTAAGGTCCAAGAGACGATGTTGGTCCAAAGAACGTCACCTCAGAGTCCACTGCTGTGTAGCTAAATCATATAACAGGTCACAGTA-3'
3'-TCTCGTATAGGGTGAGGTGATTCCAGGTTCTTCTGCTACAACCAGGTTTCTTGCAGTGGAGTCTCAGTGAACGACACATCGATTTAGTATATTGTCCAGTGTCAT-5'
                    XbaI M   G   G   F   K   V   E   N   H   T   A   C   H   C   S   T   C   Y   Y   H   K   S   *
5'-ATGGGGGGTTTCAAAGTGGAGAACCACACGCGTGCCACTGCCAGTACTTGTTATTATCACAAATCTTAAATGTTTACCAAGTGCTGTCTTGATGACTGCTGATTTC-3'
3'-TACCCCCCAAAGTTTCACCTCTTGGTGTGCACGGTGACGGTCATGAACAATAATAGTGTTTAGAATTTACAAAATGTTCACGACAGAACTACTGACGACTAAAAG-5'
                                             DraIII      PstI   ScaI 5'-TGGAATGGAAAATTAAGTTGTTTAGTGTTTATGGCTTTGTTGTGAGATAAAACTCTCCTTTCCTTACCATACCACTTTGACACGCTTCAAGGATATACTCGAGCTTTACT-3'
3'--ACCTTACCTTTTAATTCAACAAATCACAAACTACTTCTATTTGAGAGGAAAAGGAATGTATGGTGAAACTGTGCGAAGTTCCTATATGACGTCGAAATGA-5'

5'-GCCTTCCTCCTTATCCTACAGTACAATCAGCAGTCTAGTTCTTCTTTCATTGGAATGAATACAGCATTAAGCTGGGGATCC-3'
3'--CGGAAGGAGGAATAGGATGTCATGTTAGTCGTCAGATCAAGAAGAAAGTAAACCTTACTTATGTCGTAATTCGACCCCTAGG-5'
                                                                                BamHI
```

Figure 6

```
                                    M   E   M   F   Q   G   L   L   L   L   L   L   S   M   G   G   T   W
5'-CTCGAGTCTAGACCCAGCTTAGACAAGGCAGGGACGCACCAAGGATGGAGATGTTCCAGGGGCTGCTGCTGTTGCTGTCTGCTGAGCATGGGCGGGACATGG-3'
3'-GAGCTCAGATCTGGGTCGAATCTGTTCCGTCCTCCGTCGTGGTTCCTACCTCTACAAGGTCCCCGACGACGACAACGACGACTCGTACCGCCCTGTACC-5'
   XhoI XbaI

A   S   C   G   G   R   I   A   R   L   E   E   K   V   K   T   L   K   A   Q   N   S   E   L   A   S   T   A   N   M   L   R   E   Q
5'-GCTAGCTGTGGCGCCGGCCATTGCTAGATTGGAAGAGAAGTTAAAACTCTGAAGGCCCAAAACAGGAACTGGCTTCCACTGCTAATATGCTGCGTGAACAA-3'
3'-CGATCGACACCGCCGGCCGTAACGATCTAACCTTCTCTTCAATTTTGAGACTTCCGGGTTTTGTCCTTGACCGAAGTGACGATTATACGACGCACTTGTT-5'
   NheI

V   A   Q   L   K   Q   K   V   M   G   L   R   P   R   C   R   P   I   N   A   T   L   A   V   E   K   E   G   C   P   V   C   I   T
5'-GTCGCTCAACTGAAGCAAAAGGTTATGGGTTTGCGCCCTAGGTGCCGCCCATCAATGCCACCCTGGCTGTGGAGAAGGAAGGCTGCCCGTGTGCATCACC-3'
3'-CAGCGAGTTGACTTCGTTTTCCAATACCCAAACGCGGGATCCACGGCGGGTAGTTACGGTGGGACCGACACCTCTTCCTCCGACGGGCACACGTAGTGG-5'
               AvrII BanI

V   N   T   T   I   C   A   G   Y   C   P   T   M   T   R   V   L   Q   G   V   L   P   A   L   P   Q   V   V   C   N   Y   R   D   V
5'-GTCAACACCACCATCTGTGCCGGCTACTGCCCCACCATGACCCGCGTGCTGCAGGGCGTCCTCCCGGCCCTGCCTCAGGTGGTGTGCAACTACCGCGATGTG-3'
3'-CAGTTGTGGTGGTAGACACGGCCGATGACGGGGTGGTACTGGGCGCACGACGTCCCGCAGGAGCGGGACGAGTCCACCACACGTTGATGGCGCTACAC-5'

R   F   E   S   I   R   L   P   G   C   P   R   G   V   N   P   V   V   S   Y   A   V   A   L   S   C   Q   C   A   L   C   R   R   S
5'-CGCTTCGAGTCCATCCGGCTCCCTGGCTGCCCGCGCGGCGTGAACCCCGTGGTCTCCTACGCCGTGGCTCTCAGCTGCCAGTGTGCACTCTGCCGCCGCAGC-3'
3'-GCGAAGCTCAGGTAGGCCGAGGGACCGACGGGCGCGCCGCACTTGGGGCACCAGAGATGCGGCACCGAGAGTCGACAGTTACACGTGAGACGGCGGCGTCG-5'

T   T   D   C   G   G   P   K   D   H   P   L   T   C   D   D   D   P   R   F   Q   D   S   S   S   K   A   P   P   P   S   L   P   S
5'-ACCACTGACTGCGGGGGTCCCAAGGACCACCCCTTGACCTGTGATGACGACCCCGCTTCCAGGACTCCTCTTCCTCAAAGGCCCCCCCAGCCTTCCAAGC-3'
3'-TGGTGACTGACGCCCCCAGGGTTCCTGGTGGGAACACTGACTGCTGGGGCGAAGGTCCTGAGGAGAAGAGGAGTTTCCGGGGGGGGTCGGAAGGTTCG-5'

P   S   R   L   P   G   P   S   D   T   P   I   L   P   Q   *
5'-CCATCCCGACTCCCGGGGCCCTCGACACCCCGATCCTCCAATAAAGGCTTCTCAATCCGCAAGCTGGGAGCTCGGATCC-3'
3'-GGTAGGGCTGAGGGCCCCGGGAGCTGTGGGGCTAGGAGGGCTAGGAGGTTATTTCCGAAGAGTTAGGCGTTCGACCCTCGAGCCTAGG-5'
                                                                                      BamHI

5'-AGCTCGGATCC-3'
3'-TCGAGCCTAGG-5'
         BamHI
```

Figure 9

```
                                                        M  D  Y  Y  R  K  Y  A  A  I  F
5'-CTCGAGTCTAGAACCCAGCTTGGCAGTCAACCGCCCTGAACACATCCTGCAAAAAGCCCAGAGAAAGGAGCGCCATGGATTACTACAGAAAATATGCAGCTATCTTT-3'
3'-GAGCTCAGATCTGGGTCGAACCGTCAGTTGGCGGGACACTTGTGTAGGACGTCAGAGAAGCCCAGAGAAGCCCTGTTCCTGCGGTACCTAATGATGTCTTTTATACGTCGATAGAAA-5'
   XhoI  XbaI                                                                                                    NheI

L  H  V  L  H  S  A  P  D  V  Q  D  C  P  E  C  T  L  Q  E  N  P  F  F  S  Q  P  G  A  P  I  L  Q  C  M
5'-CTGCATGTTCTCCATTCCGCTCCTGATGTGCAGGATTGCCCAGAATGCACGCTACAGGAAAACCCATTCTTCTCCCAGCCGGGTGCCCCAATACTTCAGTGCATG-3'
3'-GACGTACAAGAGAGGTAAGGCGAGGACTACACGTCCTAACGGGTCTTACGTGCGATGTCCTTTTGGGTAAGAAGAGGGTCGGCCCACGGGGTTATGAAGTCACGTAC-5'
                                                       BsmI

G  C  C  F  S  R  A  Y  P  T  P  L  R  S  K  K  T  M  L  V  Q  K  D  V  T  S  E  S  T  C  C  V  A  K  S
5'-GGCTGCTGCTTCTCTAGAGCATATCCCACTCCACTAAGATCTAAGAAGACTATGTTGGTCCAAAAGGACGTCACTAGTGAGTCCACTTGCTGTGTAGCTAAATCA-3'
3'-CCGACGACGAAGAGATCTCGTATAGGGTGAGGTGATTCTAGATTCTTCTGATACAACAGGTTTTCCTGCAGTGATGACTCAGGTGAACGACACATCGATTTAGT-5'
                  XbaI           BglII                                  AatII  SpeI

G  C  C  F  S  R  A  Y  P  T  P  L  R  S  K  K  T  M  L  V  Q  K  D  V  T  S  E  S  T  C  C  V  A  K  S
                                                                                                            *
   Y  N  R  V  T  V  M  G  G  F  K  V  E  N  H  T  A  C  H  C  S  T  C  Y  Y  H  K  S  *
5'-TATAACAGGGTCACAGTAATGGGGGGTTTCAAAGTGGAGAACCACACGGCGTGCCACTGCAGTACTTGTTATTATCACAAATCTTAAATGTTTACCAAGTGCTG-3'
3'-ATATTGTCCCAGTGTCATTACCCCCCAAAGTTTCACCCTCTTGGTGTGCCGCACGGTGACGTCATGAACAATAATAGTGTTTAGAATTACAAAATGTTCACGAC-5'
                                DraIII                      PstI   ScaI

5'-TCTTGATGACTGCTGATTTCTGGAATGGAAATTAAGTTGTTTAGTGTTTATGGCTTTGTGAGATAAAACTCTCCTTTCCTTACCATACCACTTTGACACGCT-3'
3'-AGAACTACTGACGACTAAAGACCTTACCTTTAATTCAACAAATCACAAATACCGAAACTCTATTTTGAGAGAAAAGGAATGGTATGGTGAAACTGTGCGA-5'

5'-TCAAGGATATACTGCAGCTTTACTGCCTTCCCCCTTATCCTACAGTACAATCAGCAGTCTAGTTCTTTCATTGGAATGAATACAGCATTAAGCTGGGGATCC-3'
3'-AGTTCCTATATGACGTCGAAATGACGGAAGGAGGGAATAGAGATGTCATGTTAGTCGTCAGATCAAGAAAGTAAACCTTACTTATGTCGTAATTCGACCCCTAGG-5'
                                                                                                       BamHI
```

Figure 10

```
                              M  E  M  F  Q  G  L  L  L  L  L  L  L  S  M  G  G  T  W  A  S
5'-CTCGAGTCTAGACCCAGCTTAGACAAGGCAGGGACGCACCAAGGATGGAGATGTTCCAGGGCTGCTGCTGTTGCTGCTGTTGCTGAGCATGGGCGGGACATGGGACATGGCTAGC-3'
3'-GAGCTCAGATCTGGGTCGAATCTGTTCCGTCCCTGCGTGGTTCCTACCTCACAAGGTCCCCGACGACGACAACGACGACGACTCGTACCCGCCCTGTACCCGATCG-5'
   XhoI  XbaI                                                                                               NheI

C  G  G  L  T  D  T  L  Q  A  E  T  D  Q  L  E  D  K  K  S  A  L  Q  T  E  I  A  N  L  L  K  E  K  E  K  L
5'-TGTGGTGGGTTAACCGATACCCTGCAAGCTGAAACTGATCAACTGGAAGATAAGAAATCGCTCTGCAAACTGAAATCGCTAATCTGCTGAAAGAGAAGAAAGCTT-3'
3'-ACACCACCCAATTGGCTATGGGACGTTCGACTTTGACTAGTTGACCTTCTATTCTTTAGCGAGACGTTGACTTTAGCGATTAGACGACTTTCTCTTCTTCGAA-5'
                                                                                                      HindIII C  G  G  L  T  D  T  L  Q  A  E  T  D  Q  L  E  D  K  K  S  A  L  Q  T  E  I  A  N  L  L  K  E  K  E  K  L
    E  F  I  L  A  G  Q  D  C  P  E  C  T  L  Q  E  N  P  F  F  S  Q  P  G  A  P  I  L  Q  C  M  G  C  C  F  S
5'-GAGTTCATCCTGGCCGGCCAAGATTGTCCGGAATGCACGCTACAGGAGAATCCCTTCTTCTCCCAGCCGGGTGCCCCAATACTTCAGTGCATGGGCTGCTGCTCT-3'
3'-CTCAAGTAGGACCGGCCGGTTCTAACAGGCCTTACGTGCGATGTCCTTTTAGGTAAGAAGAGGTCGGCCCACGGGTTATGAAGTCACGTACCCGACGACGAAGAGA-5'
                        NgoMI  BspEI BsmI R  A  Y  P  T  P  L  R  S  K  K  T  M  L  V  Q  K  D  V  T  S  E  S  T  C  C  V  A  K  S  Y  N  R  V  T  V
5'-AGAGCATATCCCACTCCACTCCGAGCTAAGAAGACTATGTTGGTCCAAAAGGACGTCACTAGTGAGTCCACTTGCTGTAGCTAAATCATATAACAGGGTCACAGTA-3'
3'-TCTCGTATAGGGTGAGGTGATTCTAGATTCTTCTGATAACAACCAGTTTCCTGCAGTGATCACTCAGTTTAGCGTGAACGACACATCGATTTAGTATATTGTCCAGTGTCAT-5'
   XbaI                                   AatII SpeI M  G  G  F  K  V  E  N  H  T  A  C  H  C  S  T  C  Y  Y  H  K  S  *
5'-ATGGGGGGTTTCAAAGTGGAGAACCACACGGCTGCCACTGCAGTACTTGTTATTATCACAAATCTTAAATGTTTACCAAGTGCTGTCTTGATGACTGCTGATTTC-3'
3'-TACCCCCCAAAGTTTCACCTCTTGGTGCCGACACGGTGACGTCATGAACAATATAGTGTTTAGAATTTACAAATGTTACAAAATGGTTCACGACAGAACTACTGACGACTAAAAG-5'
                                          DraIII  PstI  ScaI 5'-TGGAATGGAAAATTAAGTGTTTAGTGTTATGGCTTTGTGAGATAAAACTCTCCTTTCCTTACCATACCACTTTGACACGCTTCAAGGATATACTGCAGCTTTACT-3'
3'-ACCTTACCTTTTAATTCAACAAATCACAAATACCGAAACACTCTATTTTGAGAGGAAAAGGAATGGTATGGTGCAAGTTCCTATATGACGTCGAAATGA-5'

5'-GCCTTCCTCCTTATCCTACAGTACAATCAGCAGTCTAGTTCTTTCATTGGAATGAATACAGCATTAAGCTGGGGATCC-3'
3'-CGGAAGGAGGAATAGGATGTCATGTTAGTCGTCAGATCAAGATCAAGAAAAGTAAACCTTACTTATGTCGACCCCCTAGG-5'
                                                                       BamHI
```

Figure 10A
    Amino-MEMFQGLLLLLLLSMGGTWA-SCGGLTDTLQAETDQLEDKKSALQTEIANLLKEKEKLEFILAG-KSKR-
QDCPECTLQENPFFSQPGAPILQCMGCC-
    FSRAYPTPLRSKKTMLVQKNVTSESTCCVAKSYNRVTVMGGFKVENHTACHCSTCYYHKS-Carboxyl Figure 10B
    Amino-MEMFQGLLLLLLLSMGGTWA-SCGGRIARLEEKVKTLKAQNSELASTANMLREQVAQLKQKVMG-KSKR-
LRPRCRPINATLAVEKEGCPVCITVNTT- ICAGYCPTMTRVLQGVLPALPQVVCNYRDVRFESIRLPGCPRGVNPVVSYAVALSCQCALCRRSTTDCGGPKDHPLTCD
DPRFQDSSSSKAPPPSLPSPSRLPG-
    PSDTPILPQ-Carboxyl

Figure 11

```
                                      M   E   M   F   Q   G   L   L   L   L   L   L   L   S   M   G   G   T   W   A   S
5'-CTCGAGTCTAGACCAGCTTAGACAAGGCAGGGGACGCACCAAGGATGGAGATGTTCCAGGGGCTGCTGCTGTTGCTGCTGAGCATGGGCGGGGACATGGGCTAGC-3'
3'-GAGCTCAGATCTGGGTCGAATCTGTTCCGTCCCCTGCGTGGTTCCTACCTCTACAAGGTCCCCGACGACGACAACGACGACGACTCGTACCCGCCCTGTACCCGATCG-5'
    XhoI XbaI                                                                                                    NheI

C   G   G   L   T   D   T   L   Q   A   E   T   D   Q   L   E   D   K   K   S   A   L   Q   T   E   I   A   N   L   L   K   E   K   E   K   L
5'-TGTGGTGGGTTAACCGATACCCTGCAAGCTGAAACTGATCAACTGGAAGATAAGAAATCTGCTCTGCAAACTGAAATCGCTAATCTGCTGAAAGAGAAAGAAAGCTT-3'
3'-ACACCACCCAATTGGCTATGGGACGTTCGACTTTGACTAGTTGACCTTCTATTCTTTAGACGAGACGGTTTGACTTTAGCGATTAGACGACTTTCTCTTTCTTTCGAA-5'
                                                                                                            HindIII E   F   I   L   A   G   Q   D   A   P   E   C   T   L   Q   E   N   P   F   F   S   Q   P   G   A   P   I   L   Q   C   M   G   C   C   F   S
5'-GAGTTCATCCTGGCCGGCCAAGATGCTCCGGAATGCACGCTACAGGAGAAACCATTCTTCTCCCAGCCGGGTGCCCCAATACTTCAGTGCATGGCTGCTGCTTCT-3'
3'-CTCAAGTAGGACCGGCCGGTTCTACGAGGCCTTACGTGCGATGTCCTCTTTGGGTAAGAAGAGGGTCGGCCCACGGGGTTATGAAGTCACGTACCCGACGACGAAGAGA-5'
              NgoMI        BspEI BsmI R   A   Y   P   P   L   R   S   K   K   T   M   L   V   Q   K   N   V   T   S   E   S   T   C   C   V   A   K   S   Y   N   R   V   T   V
5'-AGAGCATATCCCACTCCACTAAGGTCCAAGAAGACGATGTTGGTCCAAAAGAACGTCACCTCAGAGTCCACTTGCTGTAGCTAAATCATATAACAGGGTCACAGTA-3'
3'-TCTCGTATAGGGTGAGGTGATTCCAGGTTCTTCTGCTACAAGCCAGGTTTCTTGCAGTGGAGTCTCAGTGAACGACACATCGATTTAGTATATTGTCCCAGTGTCAT-5'
    XbaI M   G   G   E   K   V   E   N   H   T   A   C   H   C   S   T   C   Y   Y   H   K   S   *
5'-ATGGGGGGTTTCAAAGTGGAGAACCACACGGCTGCCACTGCAGTACTTGTTATTATCACAAATCTTAAATGTTTACCAAGTGCTGTCTCTTGATGACTGCTGATTTC-3'
3'-TACCCCCCAAAGTTTCACCTCTTGGTGTGCCGCCACGGTGACGTCATGAACGATGTGACGTCATGAACAATAATAGTGTTTAGAATTTACAAAATGTTACGACAGAACTACTGACGACTAAAAG-5'
                                      DraIII       PstI ScaI 5'-TGGAATGGAAAATTAAGTTGTTTAGTGTTTATGGCTTTGTGAGATAAAACTCTCCTTTTCCTTACCATACCACTTTGACACGCTTCAAGGATATACTGCAGTTTACT-3'
3'-ACCTTACCTTTTAATTCAACAAATCACAAATCACGAAACACTCTATTTTGAGAGGAAAAGGAATGTGAAACTGTGCGAAGTTCCTATATGACGTCGAAATGA-5'

5'-GCCTTCCTCCCTTATCCTACAGTACAATCAGCAGTCTAGTTCTTTTCATTTGGAATGAATACAGCATTAAGCTGGGGATCC-3'
3'-CGGAAGGAGGGAATAGGATGTCATGTTAGTCGTCAGATCAAGAAAAGTAAACTTACTTATGTCGTAATTCGACCCCTAGG-5'
                                                                                BamHI
```

Figure 12

```
                    M   E   M   F   Q   G   L   L   L   L   L   L   S   M   G   G   T   W
5'-CTCGAGTCTAGACCCAGCTTAGACAAGGACGCACCAAGGATGGAGATGTTCCAGGGGCTGCTGCTGTTGCTGTTGCTGTCTGAGCATGGGGGACATGG-3'
3'-GAGCTCAGATCTGGGTCGAATCTGTTCCGTCCCCTGCGTGGTTCCTACCTCTACAAGGTCCCCGACGACGACAACGACGACGACTCGTACCGCCTGTACC-5'
   XhoI XbaI

A   S   C   G   G   R   I   A   R   L   E   E   K   V   K   T   L   K   A   Q   N   S   E   L   A   S   T   A   N   M   L   R   E   Q
5'-GCTAGCTGTGGCGGCCGCATTGCTAGATTGGAAGAGAAAGTTAAAACTCTGAAGGCCCAAAACAGCGAACTGCTTCCACTGCTAATATGCTGTGAACAA-3'
3'-CGATCGACACCGCCGGCGTAACGATCTAACCTTCTCTTTCAATTTGAGACTTCCGGGTTTGTCGCTTGACGAAGGTGACGATTATACGACGACTTGTT-5'
   NheI

V   A   Q   L   K   Q   K   V   M   G   L   R   P   R   C   R   P   I   N   A   T   L   A   V   E   K   E   G   C   P   V   C   I   T
5'-GTCGCTCAACTGAAGCAAAAGGTTATGGGTTTGCGCCCTAGTGCCCGCCCATCAATGCCACCCTGGCTGTGGAGAAGGAGGGCTGCCCCGTGTGCATCACC-3'
3'-CAGCGAGTTGACTTCGTTTTCCAATACCCAAACGCGGGATCCACGGGCCCTAGTTACGGTGGGACCGACACCTCTTCCTCCCGACGGGGCACACGTAGTGG-5'
                                      AvrII BanI

V   N   T   T   I   C   A   G   Y   C   P   T   M   T   R   V   L   Q   G   V   L   P   A   L   P   Q   V   V   C   N   Y   R   D   V
5'-GTCAACACCACCATCTGTGCCGGCTGTGTCTCCACCATGACACGTGTCTGCAGGGCGTCCTCCCGGCCTCAGGTGGTGTGCAACTACCGCGATGTG-3'
3'-CAGTTGTGGTGGTAGACAGGCGCCGACAACAGAGATGGTACTGTGCACACGACGTCCCGCAGGAGGGCCGGAGTCCACCACACGTTGATGGCGCTACAC-5'
                                PstI
                      NgoMI

R   F   E   S   I   R   L   P   G   C   P   R   G   V   N   P   V   V   S   Y   A   V   A   L   S   C   Q   C   A   L   C   R   R   S
5'-CGCTTCGAGTCCATCCGGCTCCCTGGCTGCCCCCGTGGTCTCTCAGCTGCACTCTGCGCCGCAGC-3'
3'-GCGAAGCTCAGGTAGGCCGAGGGACCGACGGGGCGCGCCGCACTTGGGGCACCAGAGATGCGCACCGAGGATCGACAGTTACACGTGAGACGGGCGTCG-5'

T   T   D   C   G   G   P   K   D   H   P   L   T   C   D   D   P   R   F   Q   D   S   S   S   K   A   P   P   P   S   L   P   S
5'-ACCACTACTGACTGCGGGGGTCCAAGGACCACCCCTTGACCTGTGATGATGACCCCCGCTTCCAAGACTCCTCTTCCTCAAAGGCCCCTCCCCCAGCCTTCCAAGC-3'
3'-TGGTGATGACTGACGCCCCCAGGGTTCCTGGTGGGGAACTGGACACTACTGGGGGCGAAGGTTCTGAGGAGAAGGAGTTTCCGGGAGGGGGGGTCGAAGGTTCG-5'

P   S   R   L   P   G   P   S   D   T   P   I   L   P   Q   *
5'-CCATCCCGACTCCCGGGGCCCTCGAGACACCCCGATCCTCCCACAATAAAGGCTTCAATCCGCAAGCTGGGAGCTCGATCCGGAGCTCGCGTCGACCCGCGG-3'
3'-GGTAGGGCTGAGGGCCCCGGGAGCCTGTGGGGCTAGGAGGGTGTTATTTCCGAAGAGAGTTAGGCGTTCGACCCTCGAGCCTCGAGCTCCAGCTGGGCGCC-5'

5'-AGCTCGGATCC-3'
3'-TCGAGCCTAGG-5'
         BamHI
```

Figure 13

```
                                                M  E  M  F  Q  G  L  L  L  L  L  L  S  M  G  G  T  W
5'-CTCGAGTCTAGACCCAGCTTAGACAAGGATGGAGAGTTCCAGGGGACGCACCAAGGCAGGGGACGCACCAAGATGGAGAGTTCCAGGGGACGCTGCTGTTGCTGTGCTCTGCTGAGCATGGGCGGACATGG-3'
3'-GAGCTCAGATCTGGGTCGAATCTGTTCCGTCCCCTGCGTGGTTCCTACCTACAAGTCCCCGACGACGACAACGACGACGACTCGTACCGCCCTGTACC-5'
   XhoI XbaI

A  S  C  G  G  R  I  A  R  L  E  E  K  V  K  T  L  K  A  Q  N  S  E  L  A  S  T  A  N  M  L  R  E  Q
5'-GCTAGCTGTGGCGGCCGCCATTGCTAGATTGGAAGAGAAGAGTTAAAACTCTGAAGGCCCAAAACAGGAACTGGCTTCCACTGCTAATATGTGCGTGAACAA-3'
3'-CGATCGACACCGCCGGCGGTAACGATCTAACCTTCTCTTCAATTTGAGACTTCCGGTTTGTGCTTGACCGAAGTGACGATTATACACGCACTTGTT-5'
   NheI

V  A  Q  L  K  Q  K  V  M  G  L  R  P  R  C  R  P  I  N  A  T  L  A  V  E  K  E  G  C  P  V  A  I  T
5'-GTCGCTCAACTGAAGCAAAAGGTTATGGGTTTGCGCCCTAGGTGTCGTCCTATTAATGCTACTCTGGCTGTTGAGAAGGAAGGTTGTCCTGTGGCCATTACT-3'
3'-CAGCGAGTTGACTTCGTTTTCCAATACCCAAACGCGGGATCCACAGCAGGATAATTACGATGAGACGACAACTCTTCCTTCCAACAGGACACCGGTAATGA-5'
                 AvrII BanI

V  N  T  T  I  C  A  G  Y  C  P  T  M  T  R  V  L  Q  G  V  L  P  A  L  P  Q  V  V  C  N  Y  R  D  V
5'-GTTAACACTACCATCTGTGCCGGCTGTGTGTCCTACCATGACACGTGCTGCAGGGGTCTCCTCCCGGCCCTGCCTCAGGTGTGTGCAACTACCGCGATGTG-3'
3'-CAATTGTGATGGTAGACACGGCCGACAACAGGATGGTACTGTGCACGACGTCCCCCAGAGGAGGGCCGGAGTCCACCACAGTTGATGGCGCTACAC-5'
          NgoMI                                                              PstI

R  F  E  S  I  R  L  P  G  C  P  R  G  V  N  P  V  V  S  Y  A  V  A  L  S  C  Q  C  A  L  C  R  R  S
5'-CGCTTCGAGTCCATCCGGCTCCCCGGCTGCCCCCGTGGCGTGAACCCCGTGGTCTCTACGCCGTGGCTCTCAGCTGTGCACTCTGCCGCCGCAGC-3'
3'-GCGAAGCTCAGGTAGGCCGAGGGGCCGACGGGGCACCAGAGATGCGGCACCGAGAGTCGACAGTTACACGTGAGACGGCGGCGTCG-5'

T  T  D  C  G  G  P  K  D  H  P  L  T  C  D  D  D  P  R  F  Q  D  S  S  S  K  A  P  P  P  S  L  P  S
5'-ACCACTGACTGCGGGGGTCCCAAGGACCACCCCTTGACCTGTGATGATGACCCCCGCTTCCAGGACTCCTCTTCCAAAGGCCCCTCCCCCAGCCTTCCAAGC-3'
3'-TGGTGACTGACGCCCCCAGGGTTCCTGGTGGGGGAACTGGACACTACTGGGGGCGAAGGTCCTGAGGAGAAGGAGTTTCCGGGGAGGGGGTCGAAGGTTCG-5'

P  S  R  L  P  G  P  S  D  T  P  I  L  P  Q  *
5'-CCATCCCGGACTCCCGGGGCCCTCGGACACCCCGATCCTCCCACAATAAAGGCTTCCAATCCGCAAGCTGGGAGCTCGGATCCGGCGCGTCGACCCGCGG-3'
3'-GGTAGGGCTGAGGGCCCCGGGGAGCCTGTGGGGGCTAGGAGAGTGTTATTTCCGAAGAGTTAGGCGTTCGACCCCTCGAGCCTCGAGCCGGCGCAGCTGGGCGCC-5'

5'-AGCTCGGATCC-3'
3'-TCGAGCCTAGG-5'
            BamHI
```

Figure 14

```
                         M  E  M  F  Q  G  L  L  L  L  L  L  L  S  M  G  G  T  W
5'-CTCGAGTCTAGACCCAGCTTAGACAAGGCAGGACGCACCAAGGAGATGGAGATGTTCCAGGGGCTGCTGCTGTTGCTGCTGTTGCTGCTGAGCATGGGCGGGACATGG-3'
3'-GAGCTCAGATCTGGGTCGAATCTGTTCCGTCCTGCGTGGTTCCTACCTCTACAAGGTCCCCGACGACGACAACGACGACGACTCGTACCCGCCCTGTACC-5'
   XhoI  XbaI

A  S  C  G  G  R  I  A  R  L  E  E  K  V  K  T  L  K  A  Q  N  S  E  L  A  S  T  A  N  M  L  R  E  Q
5'-GCTAGCTGTGGCGGCCGCATTGCTAGATTGGAAGAGAAGTTAAAACTCTGAAGGCCCAAAACAGCGAACTGCTTCCACTGCGAACTGCTGCGTGAACAA-3'
3'-CGATCGACACCGCCGGCGTAACGATCTAACCTTCTCTTCAATTTGAGACTTCCGGGTTTTGTCGCTTGACCGAAGGTGACGATTATACGACGCACTGTT-5'
   NheI

V  A  Q  L  K  Q  K  V  M  G  L  R  P  R  C  R  P  I  N  A  T  L  A  V  E  K  E  G  C  P  V  A  I  T
5'-GTCGCTCAACTGAAGCAAAAGGTTATGGGTTTGCGCCCTAGGTGTCGTCCTATTAATGCTACTCTGGCTGTTGAGAAGGAAGGTTGTCCTGTGGCCATTACT-3'
3'-CAGCGAGTTGACTTCGTTTTCCAATACCCAAACGCGGGATCCACAGCAGGATAATTACGATGAGACGACCAACTCTTCCTTCCAACAGGACACCGGTAATGA-5'
           AvrII  BanI

V  N  T  T  I  C  A  G  Y  C  P  T  M  T  R  V  L  Q  G  V  L  P  A  L  P  Q  V  V  C  N  Y  R  D  V
5'-GTTAACACTACCATCTGTGCCGGCTACTGTCCTACCATGACACGTGTCTGCAGGGCGTCCTCCCCGCCTCCAGGTGGTGCAACTACCGGCGATGTG-3'
3'-CAATTGTGATGGTAGACACGGCCGATGACAGGATGGTACTGTGCACAGACGTCCCGCAGGAGGCCGGACGAGTCCACACACGTTGATGGCGCTACAC-5'
                                           PstI
                     NgoMI

R  F  E  S  I  R  L  P  G  C  P  R  G  V  N  P  V  V  S  Y  A  V  A  L  S  C  Q  C  A  L  *
5'-CGCTTCGAGTCCATCCGGCTCCCTGGCTGCCCGCGCGGCGTGAACCCCGTGGTCTCCTACGCCGTGGCTCTCAGCTGTCAATGCGCTTTAAAGGATCC-3'
3'-GCGAAGCTCAGGTAGGCCGAGGGACCGACGGGCGCGCCGCACTTGGGGCACCAGAGATGCCGCACCGAGAGTCGACAGTTACGCCGAAATTCCTAGG-5'
                                                                       BssHII  DraI  BamHI
```

Figure 17

Full-length hCG α-subunit:
Amino-MEMFQGLLLLLLLSMGGTWA-SCGGLTDTLQAETDQLEDKKSALQTEIANLLKEKEKLEFILAG-KSKR-APDVQDCPECTLQENPFFSQPGAPILQC-
MGCCFSRAYPTPLRSKKTMLVQKNVTSESTCCVAKSYNRVTVMGGFKVENHTACHCSTCYYHKS-Carboxyl Full-length hCG β-subunit:
Amino-MEMFQGLLLLLLLSMGGTWA-SCGGRIARLEEKVKTLKAQNSELASTANMLREQVAQLKQKVMG-KSKR-SKEPLRPRCRPINATLAVEKEGCPVCIT-
VNTICAGYCPTMTRVLQGVLPALPQVVCNYRDVRFESIRLPGCPRGVNPVVSYAVALSCQCALCRRSTTDCGGPKDHPLTCDDPRFQDSSSSKAPPSLPSPS-
RLPGPSDTPILPQ-Carboxyl Full-length hLH β-subunit:
Amino-MEMFQGLLLLLLLSMGGTWA-SCGGRIARLEEKVKTLKAQNSELASTANMLREQVAQLKQKVMG-KSKR-SREPLRPWCHPINAILAVEKEGCPVCIT-
VNTTICAGYCPTMMRVLQAVLPPLPQVVCTYRDVRFESIRLPGCPRGVDPVVSFPVALSCRCALCRRSTSDCGGPKDHPLTCDHPQ-Carboxyl Full-length hFSH β-subunit:
Amino-MEMFQGLLLLLLLSMGGTWA-SCGGRIARLEEKVKTLKAQNSELASTANMLREQVAQLKQKVMGSKEPLR-KSKR-NSCELTNITIAIEKEECRFCIS-
INTTWCAGYCYTRDLVYKDPARPKIQKTCTFKELVYETVRVPGCAHHADSLYTYPVATQCHCGKCDSDSTDCTVRGLGPSYCSFGEMKE-carboxyl Full-length hTSH β-subunit:
Amino-MEMFQGLLLLLLLSMGGTWA-SCGGRIARLEEKVKTLKAQNSELASTANMLREQVAQLKQKVMGSKEPLRG-KSKR-FCIPTEYTMHIERRECAYCLT-
INTTICAGYCMTRDINGKLFLPKYALSQDVCTYRDFIYRTVEIPGCPLHVAPYFSYPVALSCKCGKCNTDYSDCIHEAIKTNYCTKPQKSY-carboxyl Full-length hCG/hFSH β-subunit chimera:
Amino-MEMFQGLLLLLLLSMGGTWA-SCGGRIARLEEKVKTLKAQNSELASTANMLREQVAQLKQKVMG-KSKR-SKEPLRPRCRPINATLAVEKEGCPVCIT-
VNTTICAGYCPTMTRVLQGVLPALPQVVCNYRDVRFESIRLPGCPRGVNPVVSYAVALSCQCALCDSDSTDCTVRGLGPSYCSFGEMKESSSSKAPPSLPSPS-
RLPGPSDTPILPQ-Carboxyl Full-length hCG/hTSH β-subunit chimera:
Amino-MEMFQGLLLLLLLSMGGTWA-SCGGRIARLEEKVKTLKAQNSELASTANMLREQVAQLKQKVMG-KSKR-SKEPLRPRCRPINATLAVEKEGCPVCIT-
VNTTICAGYCPTMTRVLQGVLPALPQVVCNYRDVRFESIRLPGCPRGVNPVVSYAVALSCQCALCNTDYSDCIHEAIKTNYCTKPQKSYSSSSKAPPSLPSPS-
RLPGPSDTPILPQ-Carboxyl

Figure 18

Full-length hCG α-subunit:
Amino-MEMFQGLLLLLLLSMGGTWA-[variable region]-[ADAAPTVSIFPPSSEQLTSGGASVVCFLNNFYPKDINVKWKIDGSERQNGVLNSWTDQDSKD-STYSMSSTLTWTKDEYERHNSYTCEATHKTSTSPIVKSFNRNEC]G-KSKR-APDVQDCPECTLQENPFFSQPGAPILQCMGCCFSRAYPTPLRSKKTMLVQKNVTSE-STCCVAKSYNRVTVMGGFKVENHTACHCSTCYYHKS-Carboxyl Full-length hCG β-subunit:
Amino-MEMFQGLLLLLLLSMGGTWA-[variable region]-[SAKTTPPSVYPLAPGSAAQTNSMVTLGCLVKGYFPEPVTVTWNSGSLSSGVHTFPAVLESDL-YTLSSSVTVPSSPRPSETVTCNVAHPASSTKVDKKIVPRDC]G-KSKR-SKEPLRPRCRPINATLAVEKEGCPVCITVNTTICAGYCPTMTRVLQGVLPALPQVVCNY-RDVRFESIRLPGCPRGVNPVVSYAVALSCQCALCRRSTTDCGGPKDHPLTCDDPRFQDSSSSKAPPSLPSPSRLPGPSDTPILPQ-Carboxyl Full-length hLH β-subunit:
Amino-MEMFQGLLLLLLLSMGGTWA-[variable region]-[SAKTTPPSVYPLAPGSAAQTNSMVTLGCLVKGYFPEPVTVTWNSGSLSSGVHTFPAVLESDL-YTLSSSVTVPSSPRPSETVTCNVAHPASSTKVDKKIVPRDC]G-KSKR-SREPLRPWCHPINAILAVEKEGCPVCITVNTTICAGYCPTMRVLQAVLPPLPQVVCTY-RDVRFESIRLPGCPRGVDPVVSFPVALSCRCALCRRSTSDCGGPKDHPLTCDHPQ-Carboxyl Full-length hFSH β-subunit:
Amino-MEMFQGLLLLLLLSMGGTWA-[variable region]-[SAKTTPPSVYPLAPGSAAQTNSMVTLGCLVKGYFPEPVTVTWNSGSLSSGVHTFPAVLESDL-YTLSSSVTVPSSPRPSETVTCNVAHPASSTKVDKKIVPRDC]G-KSKR-NSCELTNITIAIEKEECRFCISINTTWCAGYCYTRDLVYKDPARPKIQKTCTFKELVYE-TVRVPGCAHHADSLYTYPVATQCHCGKCDSDSTDCTVRGLGPSYCSFGEMKE-carboxyl Full-length hTSH β-subunit:
Amino-MEMFQGLLLLLLLSMGGTWA-[variable region]-[SAKTTPPSVYPLAPGSAAQTNSMVTLGCLVKGYFPEPVTVTWNSGSLSSGVHTFPAVLESDL-YTLSSSVTVPSSPRPSETVTCNVAHPASSTKVDKKIVPRDC]G-KSKR-FCIPTEYTMHIERRECAYCLTINTTICAGYCMTRDINGKLFLPKYALSQDVCTYRDFIY-RTVEIPGCPLHVAPYFSYPVALSCKCGKCNTDYSDCIHEAIKTNYCTKPQKSY-carboxyl Full-length hCG/hFSH β-subunit chimera:
Amino-MEMFQGLLLLLLLSMGGTWA-[variable region]-[SAKTTPPSVYPLAPGSAAQTNSMVTLGCLVKGYFPEPVTVTWNSGSLSSGVHTFPAVLESDL-YTLSSSVTVPSSPRPSETVTCNVAHPASSTKVDKKIVPRDC]G-KSKR-SKEPLRPRCRPINATLAVEKEGCPVCITVNTTICAGYCPTMTRVLQGVLPALPQVVCNY-RDVRFESIRLPGCPRGVNPVVSYAVALSCQCALCDSDSTDCTVRGLGPSYCSFGEMKESSSSKAPPSLPSPSRLPGPSDTPILPQ-Carboxyl Full-length hCG/hTSH β-subunit chimera:
Amino-MEMFQGLLLLLLLSMGGTWA-[variable region]-[SAKTTPPSVYPLAPGSAAQTNSMVTLGCLVKGYFPEPVTVTWNSGSLSSGVHTFPAVLESDL-YTLSSSVTVPSSPRPSETVTCNVAHPASSTKVDKKIVPRDC]G-KSKR-SKEPLRPRCRPINATLAVEKEGCPVCITVNTTICAGYCPTMTRVLQGVLPALPQVVCNY-RDVRFESIRLPGCPRGVNPVVSYAVALSCQCALCNTDYSDCIHEAIKTNYCTKPQKSYSSSSKAPPPSLPSPSRLPGPSDTPILPQ-Carboxyl

Figure 19

Full-length hCG α-subunit:
Amino-MEMFQGLLLLLLLSMGGTWA-[variable region]-[ADAAPTVSIFPPSSEQLTSGGASVVCFLNNFYPKDINVKWKIDGSERQNGVLNSWTDQDSKD-
STYSMSSTLTWTKDEYERHNSYTCEATHKTSTSPIVKSENRNEA]G-KSKR-APDVQDCPECTLQENPFFSQPGAPILQCMGCCFSRAYPTPLRSKKTMLVQKNVTSE-
STCCVAKSYNRVTVMGFKVENHTACHCSTCYYHKS-Carboxyl Full-length hCG β-subunit:
Amino-MEMFQGLLLLLLLSMGGTWA-[variable region]-[SAKTTPPSVYPLAPGSAAQTNSMVTLGCLVKGYFPEPVTVTWNSGSLSSGVHTFPAVLESDL-
YTLSSSVTVPSSPRPSETVTCNVAHPASSTKVDKKIVPRDA]G-KSKR-SKEPLRPRCRPINATLAVEKEGCPVCITVNTTICAGYCPTMTRVLQGVLPALPQVVCNY-
RDVRFESIRLPGCPRGVNPVVSYAVALSCQCALCRRSTTDCGGPKDHPLTCDDPRFQDSSSSKAPPSLPSPSRLPGPSDTPILPQ-Carboxyl Full-length hLH β-subunit:
Amino-MEMFQGLLLLLLLSMGGTWA-[variable region]-[SAKTTPPSVYPLAPGSAAQTNSMVTLGCLVKGYFPEPVTVTWNSGSLSSGVHTFPAVLESDL-
YTLSSSVTVPSSPRPSETVTCNVAHPASSTKVDKKIVPRDA]G-KSKR-SREPLRPWCHPINAILAVEKEGCPVCITVNTTICAGYCPTMMRVLQAVLPPLPQVVCTY-
RDVRFESIRLPGCPRGVDPVVSFPVALSCRCALCRRSTDCGGPKDHPLTCDHPQ-Carboxyl Full-length hFSH β-subunit:
Amino-MEMFQGLLLLLLLSMGGTWA-[variable region]-[SAKTTPPSVYPLAPGSAAQTNSMVTLGCLVKGYFPEPVTVTWNSGSLSSGVHTFPAVLESDL-
YTLSSSVTVPSSPRPSETVTCNVAHPASSTKVDKKIVPRDA]G-KSKR-NSCELTNITIAIEKEECRFCISINTTWCAGYCYTRDLVYKDPARPKIQKTCTFKELVYE-
TVRVPGCAHHADSLYTYPVATQCHCGKCDSDSTDCTVRGLGPSYCSFGEMKE-carboxyl Full-length hTSH β-subunit:
Amino-MEMFQGLLLLLLLSMGGTWA-[variable region]-[SAKTTPPSVYPLAPGSAAQTNSMVTLGCLVKGYFPEPVTVTWNSGSLSSGVHTFPAVLESDL-
YTLSSSVTVPSSPRPSETVTCNVAHPASSTKVDKKIVPRDA]G-KSKR-FCIPTEYTMHIERRECAYCLTINTTICAGYCMTRDINGKLFLPKYALSQDVCTYRDFIY-
RTVEIPGCPLHVAPYFSYPVALSCKCGKCNTDYSDCIHEAIKTNYCTKPQKSY-carboxyl Full-length hCG/hFSH β-subunit chimera:
Amino-MEMFQGLLLLLLLSMGGTWA-[variable region]-[SAKTTPPSVYPLAPGSAAQTNSMVTLGCLVKGYFPEPVTVTWNSGSLSSGVHTFPAVLESDL-
YTLSSSVTVPSSPRPSETVTCNVAHPASSTKVDKKIVPRDA]G-KSKR-SKEPLRPRCRPINATLAVEKEGCPVCITVNTTICAGYCPTMTRVLQGVLPALPQVVCNY-
RDVRFESIRLPGCPRGVNPVVSYAVALSCQCALCDSDSTDCTVRGLGPSYCSFGEMKESSSSKAPPPSLPSPSRLPGPSDTPILPQ-Carboxyl Full-length hCG/hTSH β-subunit chimera:
Amino-MEMFQGLLLLLLLSMGGTWA-[variable region]-[SAKTTPPSVYPLAPGSAAQTNSMVTLGCLVKGYFPEPVTVTWNSGSLSSGVHTFPAVLESDL-
YTLSSSVTVPSSPRPSETVTCNVAHPASSTKVDKKIVPRDA]G-KSKR-SKEPLRPRCRPINATLAVEKEGCPVCITVNTTICAGYCPTMTRVLQGVLPALPQVVCNY-
RDVRFESIRLPGCPRGVNPVVSYAVALSCQCALCNTDYSDCIHEAIKTNYCTKPQKSYSSSSKAPPPSLPSPSRLPGPSDTPILPQ-Carboxyl

Figure 20

Full-length hCG β-subunit containing a Jun dimerization domain at its C-terminus:
Amino-MEMFQGLLLLLLLSMGGTWA-SKEPLRPRCRPINATLAVEKEGCPVCITVNTTICAGYCPTMTRVLQGVLPALPQVVCNY-
RDVRFESIRLPGCPRGVNPVVSYAVALSCQCALCRRSTTDCGGPKDHPLTCDDPRFQDSSSSKAPPPSLPSPSRLPGPSDTPILPQ-
RIARLEEKVKTLKAQNSELASTANMLREQVAQLKQKVM-Carboxyl Full-length hCG β-subunit containing a linker and a Jun dimerization domain at its C-terminus:
Amino-MEMFQGLLLLLLLSMGGTWA-SKEPLRPRCRPINATLAVEKEGCPVCITVNTTICAGYCPTMTRVLQGVLPALPQVVCNY-
RDVRFESIRLPGCPRGVNPVVSYAVALSCQCALCRRSTTDCGGPKDHPLTCDDPRFQDSSSSKAPPPSLPSPSRLPGPSDTPILPQ-
GSGSGS-RIARLEEKVKTLKAQNSELASTANMLREQVAQLKQKVM-Carboxyl hLH β-subunit containing hCG C-terminus, a linker, and a Jun dimerization domain at its C-terminus:
Amino-MEMFQGLLLLLLLSMGGTWA-SREPLRPWCHPINAILAVEKEGCPVCITVNTTICAGYCPTMMRVLQAVLPPLPQVVCTY-
RDVRFESIRLPGCPRGVDPVVSFPVALSCRCALCRRSTSDCGGPKDHPLTCDDPRFQDSSSSKAPPPSLPSPSRLPGPSDTPILPQ-
GSGSGS-RIARLEEKVKTLKAQNSELASTANMLREQVAQLKQKVM-Carboxyl hFSH β-subunit containing hCG C-terminus, a linker, and a Jun dimerization domain at its C-terminus:
Amino-MEMFQGLLLLLLLSMGGTWA-NSCELTNITIAIEKEECRFCISINTTWCAGYCYTRDLVYKDPARPKIQKTCTFKELVYE-
TVRVPGCAHHADSLYTYPVATQCHCGKCDSDTDCTVRGLGPSYCSFGEMKESSSSKAPPPSLPSPSRLPGPSDTPILPQ-
GSGSGS-RIARLEEKVKTLKAQNSELASTANMLREQVAQLKQKVM-Carboxyl hTSH β-subunit containing hCG C-terminus, a linker, and a Jun dimerization domain at its C-terminus:
Amino-MEMFQGLLLLLLLSMGGTWA-FCIPTEYTMHIERRECAYCLTINTTICAGYCMTRDINGKLFLPKYALSQDVCTYRDFIY-
RTVEIPGCPLHVAPYFSYPVALSCKCGKCNTDYSDCIHEAIKTNYCTKPQKSYSSSSKAPPPSLPSPSRLPGPSDTPILPQ-
GSGSGS-RIARLEEKVKTLKAQNSELASTANMLREQVAQLKQKVM-Carboxyl Full-length hCG β-subunit containing a Jun dimerization domain at its C-terminus expected to form an intersubunit disulfide with the α-subunit:
Amino-MEMFQGLLLLLLLSMGGTWA-SKEPLRPRCRPINATLAVEKEGCPVCITVNTTICAGYCPTMTRVLQGVLPALPQVVCNY-
RDVRFESIRLPGCPRGVNPVVSYAVALSCQCALCRRSTTDCGGPKDHPLTCDDPRFQDSSSSKAPPPSLPSPSRLPGPSDTPILPQ-
CGGRIARLEEKVKTLKAQNSELASTANMLREQVAQLKQKVM-Carboxyl Full-length hCG β-subunit containing a linker and a Jun dimerization domain at its C-terminus expected to form an intersubunit disulfide with the α-subunit:
Amino-MEMFQGLLLLLLLSMGGTWA-SKEPLRPRCRPINATLAVEKEGCPVCITVNTTICAGYCPTMTRVLQGVLPALPQVVCNY-
RDVRFESIRLPGCPRGVNPVVSYAVALSCQCALCRRSTTDCGGPKDHPLTCDDPRFQDSSSSKAPPPSLPSPSRLPGPSDTPILPQ-
GSGSGS-CGGRIARLEEKVKTLKAQNSELASTANMLREQVAQLKQKVM-Carboxyl

SEQUENCE LISTING (1) GENERAL INFORMATION:

(iii) NUMBER OF SEQUENCES: 90

(2) INFORMATION FOR SEQ ID NO:1:

(i) SEQUENCE CHARACTERISTICS:
        (A) LENGTH: 158 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:1:

```
Met Glu Met Phe Gln Gly Leu Leu Leu Leu Leu Leu Ser Met Gly
1               5                   10                  15

Gly Thr Trp Ala Ser Cys Arg Pro Ile Asn Ala Thr Leu Ala Val Glu
                20                  25                  30

Lys Glu Gly Cys Pro Val Cys Ile Thr Val Asn Thr Thr Ile Cys Ala
            35                  40                  45

Gly Tyr Cys Pro Thr Met Thr Arg Val Leu Gln Gly Val Leu Pro Ala
        50                  55                  60

Leu Pro Gln Val Val Cys Asn Tyr Arg Asp Val Arg Phe Glu Ser Ile
65                  70                  75                  80

Arg Leu Pro Gly Cys Pro Arg Gly Val Asn Pro Val Val Ser Tyr Ala
                85                  90                  95

Val Ala Leu Ser Cys Gln Cys Ala Leu Cys Arg Arg Ser Thr Thr Asp
            100                 105                 110

Cys Gly Gly Pro Lys Asp His Pro Leu Thr Cys Asp Asp Pro Arg Phe
        115                 120                 125

Gln Asp Ser Ser Ser Ser Lys Ala Pro Pro Pro Ser Leu Pro Ser Pro
    130                 135                 140

Ser Arg Leu Pro Gly Pro Ser Asp Thr Pro Ile Leu Pro Gln
145                 150                 155
```

(2) INFORMATION FOR SEQ ID NO:2:

(i) SEQUENCE CHARACTERISTICS:
        (A) LENGTH: 587 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO

-continued (xi) SEQUENCE DESCRIPTION: SEQ ID NO:2:

```
CTCGAGTCTA GACCCAGCTT AGACAAGGCA GGGGACGCAC CAAGGATGGA GATGTTCCAG      60
GGGCTGCTGC TGTTGCTGCT GCTGAGCATG GGCGGGACAT GGGCTAGCTG CCGCCCCATC     120
AATGCCACCC TGGCTGTGGA GAAGGAGGGC TGCCCCGTGT GCATCACCGT CAACACCACC     180
ATCTGTGCCG GCTACTGCCC CACCATGACC CGCGTGCTGC AGGGCGTCCT CCCGGCCCTG     240
CCTCAGGTGG TGTGCAACTA TCGCGATGTG CGCTTCGAGT CCATCCGGCT CCCTGGCTGC     300
CCGCGCGGCG TGAACCCCGT GGTCTCCTAC GCCGTGGCTC TCAGCTGTCA ATGTGCACTC     360
TGCCGCCGCA GCACCACTGA CTGCGGGGGT CCCAAGGACC ACCCCTTGAC CTGTGATGAC     420
CCCCGCTTCC AGGACTCCTC TTCCTCAAAG GCCCCTCCCC CCAGCCTCCC AAGCCCATCC     480
CGACTCCCGG GGCCCTCGGA CACCCCGATC CTCCCACAAT AAAGGCTTCT CAATCCGCAA     540
GCTGGGGAGC TCGGATCCGC GCGCGTCGAC CCGCGGAGCT CGGATCC                   587
```

(2) INFORMATION FOR SEQ ID NO:3:

(i) SEQUENCE CHARACTERISTICS:
        (A) LENGTH: 587 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
GAGCTCAGAT CTGGGTCGAA TCTGTTCCGT CCCCTGCGTG GTTCCTACCT CTACAAGGTC      60
CCCGACGACG ACAACGACGA CGACTCGTAC CCGCCCTGTA CCCGATCGAC GGCGGGGTAG     120
TTACGGTGGG ACCGACACCT CTTCCTCCCG ACGGGGCACA CGTAGTGGCA GTTGTGGTGG     180
TAGACACGGC CGATGACGGG GTGGTACTGG GCGCACGACG TCCCGCAGGA GGGCCGGGAC     240
GGAGTCCACC ACACGTTGAT AGCGCTACAC GCGAAGCTCA GGTAGGCCGA GGGACCGACG     300
GGCGCGCCGC ACTTGGGGCA CCAGAGGATG CGGCACCGAG AGTCGACAGT TACACGTGAG     360
ACGGCGGCGT CGTGGTGACT GACGCCCCCA GGGTTCCTGG TGGGGAACTG GACACTACTG     420
GGGGCGAAGG TCCTGAGGAG AAGGAGTTTC CGGGGAGGGG GGTCGGAGGG TTCGGGTAGG     480
GCTGAGGGCC CCGGGAGCCT GTGGGGCTAG GAGGGTGTTA TTTCCGAAGA GTTAGGCGTT     540
CGACCCCTCG AGCCTAGGCG CGCGCAGCTG GGCGCCTCGA GCCTAGG                   587
```

(2) INFORMATION FOR SEQ ID NO:4:

(i) SEQUENCE CHARACTERISTICS:
        (A) LENGTH: 72 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:4:

```
Met Glu Met Phe Gln Gly Leu Leu Leu Leu Leu Leu Leu Ser Met Gly
1               5                   10                  15
```

Gly Thr Trp Ala Ser Cys Gly Gly Leu Thr Asp Thr Leu Gln Ala Glu
            20                  25                  30

Thr Asp Gln Leu Glu Asp Lys Lys Ser Ala Leu Gln Thr Glu Ile Ala
        35                  40                  45

Asn Leu Leu Lys Glu Lys Glu Lys Leu Glu Phe Ile Leu Ala Gly Gln
    50                  55                  60

Asp Cys Pro Glu Cys Thr Leu Gln
65                  70

(2) INFORMATION FOR SEQ ID NO:5:

(i) SEQUENCE CHARACTERISTICS:
        (A) LENGTH: 267 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:5:

| | | | | |
|---|---|---|---|---|
| CTCGAGTCTA GACCCAGCTT AGACAAGGCA GGGGACGCAC CAAGGATGGA GATGTTCCAG | 60 |
| GGGCTGCTGC TGTTGCTGCT GCTGAGCATG GGCGGGACAT GGGCTAGCTG TGGTGGGTTA | 120 |
| ACCGATACCC TGCAAGCTGA AACTGATCAA CTGGAAGATA AGAAATCTGC TCTGCAAACT | 180 |
| GAAATCGCTA ATCTGCTGAA AGAGAAGGAA AAGCTTGAGT TCATCCTGGC CGGCCAAGAT | 240 |
| TGTCCGGAAT GCACGCTACA GGGATCC | 267 |

(2) INFORMATION FOR SEQ ID NO:6:

(i) SEQUENCE CHARACTERISTICS:
        (A) LENGTH: 267 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:6:

| | | | | |
|---|---|---|---|---|
| GAGCTCAGAT CTGGGTCGAA TCTGTTCCGT CCCCTGCGTG GTTCCTACCT CTACAAGGTC | 60 |
| CCCGACGACG ACAACGACGA CGACTCGTAC CCGCCCTGTA CCCGATCGAC ACCACCCAAT | 120 |
| TGGCTATGGG ACGTTCGACT TTGACTAGTT GACCTTCTAT TCTTTAGACG AGACGTTTGA | 180 |
| CTTTAGCGAT TAGACGACTT TCTCTTCCTT TTCGAACTCA AGTAGGACCG GCCGGTTCTA | 240 |
| ACAGGCCTTA CGTGCGATGT CCCTAGG | 267 |

(2) INFORMATION FOR SEQ ID NO:7:

(i) SEQUENCE CHARACTERISTICS:
        (A) LENGTH: 71 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:7:

```
Met Glu Met Phe Gln Gly Leu Leu Leu Leu Leu Leu Ser Met Gly
1               5                   10                  15

Gly Thr Trp Ala Ser Cys Gly Gly Arg Ile Ala Arg Leu Glu Glu Lys
                20                  25                  30

Val Lys Thr Leu Lys Ala Gln Asn Ser Glu Leu Ala Ser Thr Ala Asn
                35                  40                  45

Met Leu Arg Glu Gln Val Ala Gln Leu Lys Gln Lys Val Met Gly Leu
    50                  55                  60

Arg Pro Arg Cys Leu Ser Arg
65                  70
```

(2) INFORMATION FOR SEQ ID NO:8:

(i) SEQUENCE CHARACTERISTICS:
        (A) LENGTH: 267 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:8:

```
CTCGAGTCTA GACCCAGCTT AGACAAGGCA GGGGACGCAC CAAGGATGGA GATGTTCCAG      60

GGGCTGCTGC TGTTGCTGCT GCTGAGCATG GGCGGGACAT GGGCTAGCTG TGGCGGCCGC     120

ATTGCTAGAT TGGAAGAGAA AGTTAAAACT CTGAAGGCCC AAAACAGCGA ACTGGCTTCC     180

ACTGCTAATA TGCTGCGTGA ACAAGTCGCT CAACTGAAGC AAAAGGTTAT GGGTTTGCGC     240

CCTAGGTGCC TTAGCAGGTA AGGATCC                                        267
```

(2) INFORMATION FOR SEQ ID NO:9:

(i) SEQUENCE CHARACTERISTICS:
        (A) LENGTH: 267 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:9:

```
GAGCTCAGAT CTGGGTCGAA TCTGTTCCGT CCCCTGCGTG GTTCCTACCT CTACAAGGTC      60

CCCGACGACG ACAACGACGA CGACTCGTAC CCGCCCTGTA CCCGATCGAC ACCGCCGGCG     120

TAACGATCTA ACCTTCTCTT TCAATTTTGA GACTTCCGGG TTTTGTCGCT TGACCGAAGG     180

TGACGATTAT ACGACGCACT TGTTCAGCGA GTTGACTTCG TTTTCCAATA CCCAAACGCG     240

GGATCCACGG AATCGTCCAT TCCTAGG                                        267
```

(2) INFORMATION FOR SEQ ID NO:10:

(i) SEQUENCE CHARACTERISTICS:
        (A) LENGTH: 51 base pairs
        (B) TYPE: nucleic acid (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:10:

GAATTCGCTA GCTGTGGTGG GTTAACCGAT ACCCTGCAAG CTGAAACTGA T          51

(2) INFORMATION FOR SEQ ID NO:11:

(i) SEQUENCE CHARACTERISTICS:
            (A) LENGTH: 63 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:11:

ACCCTGCAAG CTGAAACTGA TCAACTGGAA GATAAGAAAT CTGCTCTGCA AACTGAAATC       60

GCT                                                                    63

(2) INFORMATION FOR SEQ ID NO:12:

(i) SEQUENCE CHARACTERISTICS:
            (A) LENGTH: 58 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:12:

TAGACGAGAC GTTTGACTTT AGCGATTAGA CGACTTTCTC TTCCTTTTCG AACTCAAG         58

(2) INFORMATION FOR SEQ ID NO:13:

(i) SEQUENCE CHARACTERISTICS:
            (A) LENGTH: 76 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:13:

CTTTCTCTTC CTTTTCGAAC TCAAGTAGGA CCGGCCGGTT CTAACAGGCC TTACGTGCGA       60

TGTCCCTAGG CTTAAG                                                      76

(2) INFORMATION FOR SEQ ID NO:14:

(i) SEQUENCE CHARACTERISTICS:
            (A) LENGTH: 54 base pairs

```
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:14:

GAATTCGCTA GCTGTGGCGG CCGCATTGCT AGATTGGAAG AGAAAGTTAA AACT            54

(2) INFORMATION FOR SEQ ID NO:15:

(i) SEQUENCE CHARACTERISTICS:
        (A) LENGTH: 63 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:15:

AGATTGGAAG AGAAAGTTAA AACTCTGAAG GCCCAAAACA GCGAACTGGC TTCCACTGCT      60

AAT                                                                  63

(2) INFORMATION FOR SEQ ID NO:16:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:16:

CTTGACCGAA GGTGACGATT ATACGACGCA CTTGTTCAGC GAGTTGACTT CGTTTTCCAA      60

(2) INFORMATION FOR SEQ ID NO:17:

(i) SEQUENCE CHARACTERISTICS:
        (A) LENGTH: 64 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:17:

AGTTGACTTC GTTTTCCAAT ACCCAAACGC GGGATCCACG GAATCGTCCA TTCCTAGGCT      60

TAAG                                                                 64

(2) INFORMATION FOR SEQ ID NO:18:

(i) SEQUENCE CHARACTERISTICS:
```

(A) LENGTH: 36 base pairs
    (B) TYPE: nucleic acid
    (C) STRANDEDNESS: unknown
    (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:18:

GCGCGCCATA TGTTACACCA ACAACGAAAC CAACAC                          36

(2) INFORMATION FOR SEQ ID NO:19:

(i) SEQUENCE CHARACTERISTICS:
    (A) LENGTH: 84 base pairs
    (B) TYPE: nucleic acid
    (C) STRANDEDNESS: unknown
    (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:19:

TGCTTCTCTA GAGCATATCC AACTCCATTG AGATCTAAGA AGACTATGTT GGTCCAAAAG    60

CAAGTCACTA GTGAGTCCAC TTGC                                        84

(2) INFORMATION FOR SEQ ID NO:20:

(i) SEQUENCE CHARACTERISTICS:
    (A) LENGTH: 60 base pairs
    (B) TYPE: nucleic acid
    (C) STRANDEDNESS: unknown
    (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:20:

CCATTGAGAT CTAAGAAGAC TATGTTGGTC CAAAAGGACG TCACTAGTGA GTCCACTTGC    60

(2) INFORMATION FOR SEQ ID NO:21:

(i) SEQUENCE CHARACTERISTICS:
    (A) LENGTH: 45 base pairs
    (B) TYPE: nucleic acid
    (C) STRANDEDNESS: unknown
    (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:21:

ACAAGTACTG CAGTGACAAG CAGTGTGTTG CTCCACTTTG AAACC                  45

(2) INFORMATION FOR SEQ ID NO:22:

(i) SEQUENCE CHARACTERISTICS:
    (A) LENGTH: 32 base pairs (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:22:

AGCTTGAGTT CATCCTGGCC GGCCAAGATG CT                                32

(2) INFORMATION FOR SEQ ID NO:23:

(i) SEQUENCE CHARACTERISTICS:
            (A) LENGTH: 32 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:23:

CCGGAGCATC TTGGCCGGCC AGGATGAACT CA                                32

(2) INFORMATION FOR SEQ ID NO:24:

(i) SEQUENCE CHARACTERISTICS:
            (A) LENGTH: 34 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:24:

CCGGCTGTTG TCCTACCATG ACACGTGTGC TGCA                              34

(2) INFORMATION FOR SEQ ID NO:25:

(i) SEQUENCE CHARACTERISTICS:
            (A) LENGTH: 26 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:25:

GCACACGTGT CATGGTAGGA CAACAG                                       26

(2) INFORMATION FOR SEQ ID NO:26:

(i) SEQUENCE CHARACTERISTICS:
            (A) LENGTH: 62 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:26:

CTGCGTCCTA GGTGTCGTCC TATTAATGCT ACTCTGGCTG TTGAGAAGGA AGGTTGTCCT    60

GT    62

(2) INFORMATION FOR SEQ ID NO:27:

(i) SEQUENCE CHARACTERISTICS:
        (A) LENGTH: 63 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:27:

ACAATAGCCG GCACAGATGG TAGTGTTAAC AGTAATGGCC ACAGGACAAC CTTCCTTCTC    60

AAC    63

(2) INFORMATION FOR SEQ ID NO:28:

(i) SEQUENCE CHARACTERISTICS:
        (A) LENGTH: 69 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:28:

GTGGCTCTCA GCTGTCAATG CGCGCTCTGC CGCAGATCTA CCACTGACTG CGGGGTCCCT    60

AAGGACCAC    69

(2) INFORMATION FOR SEQ ID NO:29:

(i) SEQUENCE CHARACTERISTICS:
        (A) LENGTH: 72 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:29:

CCACACGGAT CCGAGCTCTT AGCGGGGGTC ATCACAGGTC AAGGGGTGGT CCTTAGGGAC    60

CCCGCAGTCA GT    72

(2) INFORMATION FOR SEQ ID NO:30:

(i) SEQUENCE CHARACTERISTICS:
            (A) LENGTH: 12 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:30:

CGCGCTTTAA AG                                                              12

(2) INFORMATION FOR SEQ ID NO:31:

(i) SEQUENCE CHARACTERISTICS:
            (A) LENGTH: 12 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:31:

GATCCTTTAA AG                                                              12

(2) INFORMATION FOR SEQ ID NO:32:

(i) SEQUENCE CHARACTERISTICS:
            (A) LENGTH: 151 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:32:

Met Glu Met Phe Gln Gly Leu Leu Leu Leu Leu Leu Ser Met Gly
1               5                   10                  15

Gly Thr Trp Ala Ser Cys Gly Gly Leu Thr Asp Thr Leu Gln Ala Glu
            20                  25                  30

Thr Asp Gln Leu Glu Asp Lys Lys Ser Ala Leu Gln Thr Glu Ile Ala
        35                  40                  45

Asn Leu Leu Lys Glu Lys Glu Lys Leu Glu Phe Ile Leu Ala Gly Gln
50                  55                  60

Asp Cys Pro Glu Cys Thr Leu Gln Glu Asn Pro Phe Phe Ser Gln Pro
65                  70                  75                  80

Gly Ala Pro Ile Leu Gln Cys Met Gly Cys Cys Phe Ser Arg Ala Tyr
            85                  90                  95

Pro Thr Pro Leu Arg Ser Lys Lys Thr Met Leu Val Gln Lys Asn Val
            100                 105                 110

Thr Ser Glu Ser Thr Cys Cys Val Ala Lys Ser Tyr Asn Arg Val Thr
        115                 120                 125

Val Met Gly Gly Phe Lys Val Glu Asn His Thr Ala Cys His Cys Ser
130                 135                 140

```
Thr Cys Tyr Tyr His Lys Ser
145                 150
```

(2) INFORMATION FOR SEQ ID NO:33:

(i) SEQUENCE CHARACTERISTICS:
        (A) LENGTH: 729 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:33:

```
CTCGAGTCTA GACCCAGCTT AGACAAGGCA GGGGACGCAC CAAGGATGGA GATGTTCCAG    60
GGGCTGCTGC TGTTGCTGCT GCTGAGCATG GGCGGGACAT GGGCTAGCTG TGGTGGGTTA   120
ACCGATACCC TGCAAGCTGA AACTGATCAA CTGGAAGATA AGAAATCTGC TCTGCAAACT   180
GAAATCGCTA ATCTGCTGAA AGAGAAGGAA AAGCTTGAGT TCATCCTGGC CGGCCAAGAT   240
TGTCCGGAAT GCACGCTACA GGAAAACCCA TTCTTCTCCC AGCCGGGTGC CCCAATACTT   300
CAGTGCATGG GCTGCTGCTT CTCTAGAGCA TATCCCACTC CACTAAGGTC CAAGAAGACG   360
ATGTTGGTCC AAAAGAACGT CACCTCAGAG TCCACTTGCT GTGTAGCTAA ATCATATAAC   420
AGGGTCACAG TAATGGGGGG TTTCAAAGTG GAGAACCACA CGGCGTGCCA CTGCAGTACT   480
TGTTATTATC ACAAATCTTA AATGTTTTAC CAAGTGCTGT CTTGATGACT GCTGATTTTC   540
TGGAATGGAA AATTAAGTTG TTTAGTGTTT ATGGCTTTGT GAGATAAAAC TCTCCTTTTC   600
CTTACCATAC CACTTTGACA CGCTTCAAGG ATATACTGCA GCTTTACTGC CTTCCTCCTT   660
ATCCTACAGT ACAATCAGCA GTCTAGTTCT TTTCATTTGG AATGAATACA GCATTAAGCT   720
GGGGGATCC                                                          729
```

(2) INFORMATION FOR SEQ ID NO:34:

(i) SEQUENCE CHARACTERISTICS:
        (A) LENGTH: 729 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:34:

```
GAGCTCAGAT CTGGGTCGAA TCTGTTCCGT CCCCTGCGTG GTTCCTACCT CTACAAGGTC    60
CCCGACGACG ACAACGACGA CGACTCGTAC CCGCCCTGTA CCCGATCGAC ACCACCCAAT   120
TGGCTATGGG ACGTTCGACT TTGACTAGTT GACCTTCTAT TCTTTAGACG AGACGTTTGA   180
CTTTAGCGAT TAGACGACTT TCTCTTCCTT TTCGAACTCA AGTAGGACCG GCCGGTTCTA   240
ACAGGCCTTA CGTGCGATGT CCTTTTGGGT AAGAAGAGGG TCGCCCACG GGTTATGAA    300
GTCACGTACC CGACGACGAA GAGATCTCGT ATAGGGTGAG GTGATTCCAG GTTCTTCTGC   360
TACAACCAGG TTTTCTTGCA GTGGAGTCTC AGGTGAACGA CACATCGATT TAGTATATTG   420
TCCCAGTGTC ATTACCCCCC AAAGTTTCAC CTCTTGGTGT GCCGCACGGT GACGTCATGA   480
```

ACAATAATAG TGTTTAGAAT TTACAAAATG GTTCACGACA GAACTACTGA CGACTAAAAG      540

ACCTTACCTT TTAATTCAAC AAATCACAAA TACCGAAACA CTCTATTTTG AGAGGAAAAG      600

GAATGGTATG GTGAAACTGT GCGAAGTTCC TATATGACGT CGAAATGACG GAAGGAGGAA      660

TAGGATGTCA TGTTAGTCGT CAGATCAAGA AAAGTAAACC TTACTTATGT CGTAATTCGA      720

CCCCCTAGG                                                              729

(2) INFORMATION FOR SEQ ID NO:35:

(i) SEQUENCE CHARACTERISTICS:
        (A) LENGTH: 204 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:35:

```
Met Glu Met Phe Gln Gly Leu Leu Leu Leu Leu Leu Ser Met Gly
1               5                   10                  15

Gly Thr Trp Ala Ser Cys Gly Gly Arg Ile Ala Arg Leu Glu Glu Lys
            20                  25                  30

Val Lys Thr Leu Lys Ala Gln Asn Ser Glu Leu Ala Ser Thr Ala Asn
        35                  40                  45

Met Leu Arg Glu Gln Val Ala Gln Leu Lys Gln Lys Val Met Gly Leu
    50                  55                  60

Arg Pro Arg Cys Arg Pro Ile Asn Ala Thr Leu Ala Val Glu Lys Glu
65                  70                  75                  80

Gly Cys Pro Val Cys Ile Thr Val Asn Thr Thr Ile Cys Ala Gly Tyr
                85                  90                  95

Cys Pro Thr Met Thr Arg Val Leu Gln Gly Val Leu Pro Ala Leu Pro
                100                 105                 110

Gln Val Val Cys Asn Tyr Arg Asp Val Arg Phe Glu Ser Ile Arg Leu
            115                 120                 125

Pro Gly Cys Pro Arg Gly Val Asn Pro Val Val Ser Tyr Ala Val Ala
    130                 135                 140

Leu Ser Cys Gln Cys Ala Leu Cys Arg Arg Ser Thr Thr Asp Cys Gly
145                 150                 155                 160

Gly Pro Lys Asp His Pro Leu Thr Cys Asp Asp Pro Arg Phe Gln Asp
                165                 170                 175

Ser Ser Ser Ser Lys Ala Pro Pro Ser Leu Pro Ser Pro Ser Arg
                180                 185                 190

Leu Pro Gly Pro Ser Asp Thr Pro Ile Leu Pro Gln
        195                 200
```

(2) INFORMATION FOR SEQ ID NO:36:

(i) SEQUENCE CHARACTERISTICS:
        (A) LENGTH: 725 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:36:

| | | | | | |
|---|---|---|---|---|---|
| CTCGAGTCTA | GACCCAGCTT | AGACAAGGCA | GGGGACGCAC | CAAGGATGGA | GATGTTCCAG | 60 |
| GGGCTGCTGC | TGTTGCTGCT | GCTGAGCATG | GGCGGGACAT | GGGCTAGCTG | TGGCGGCCGC | 120 |
| ATTGCTAGAT | TGGAAGAGAA | AGTTAAAACT | CTGAAGGCCC | AAAACAGCGA | ACTGGCTTCC | 180 |
| ACTGCTAATA | TGCTGCGTGA | ACAAGTCGCT | CAACTGAAGC | AAAAGGTTAT | GGGTTTGCGC | 240 |
| CCTAGGTGCC | GCCCCATCAA | TGCCACCCTG | GCTGTGGAGA | AGGAGGGCTG | CCCCGTGTGC | 300 |
| ATCACCGTCA | ACACCACCAT | CTGTGCCGGC | TACTGCCCCA | CCATGACCCG | CGTGCTGCAG | 360 |
| GGCGTCCTCC | CGGCCCTGCC | TCAGGTGGTG | TGCAACTACC | GCGATGTGCG | CTTCGAGTCC | 420 |
| ATCCGGCTCC | CTGGCTGCCC | GCGCGGCGTG | AACCCCGTGG | TCTCCTACGC | CGTGGCTCTC | 480 |
| AGCTGTCAAT | GTGCACTCTG | CCGCCGCAGC | ACCACTGACT | GCGGGGGTCC | CAAGGACCAC | 540 |
| CCCTTGACCT | GTGATGACCC | CCGCTTCCAG | GACTCCTCTT | CCTCAAAGGC | CCCTCCCCCC | 600 |
| AGCCTTCCAA | GCCCATCCCG | ACTCCCGGGG | CCCTCGGACA | CCCCGATCCT | CCCACAATAA | 660 |
| AGGCTTCTCA | ATCCGCAAGC | TGGGGAGCTC | GGATCCGCGC | GCGTCGACCC | GCGGAGCTCG | 720 |
| GATCC | | | | | | 725 |

(2) INFORMATION FOR SEQ ID NO:37:

(i) SEQUENCE CHARACTERISTICS:
        (A) LENGTH: 725 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:37:

| | | | | | |
|---|---|---|---|---|---|
| GAGCTCAGAT | CTGGGTCGAA | TCTGTTCCGT | CCCCTGCGTG | GTTCCTACCT | CTACAAGGTC | 60 |
| CCCGACGACG | ACAACGACGA | CGACTCGTAC | CCGCCCTGTA | CCCGATCGAC | ACCGCCGGCG | 120 |
| TAACGATCTA | ACCTTCTCTT | TCAATTTTGA | GACTTCCGGG | TTTTGTCGCT | TGACCGAAGG | 180 |
| TGACGATTAT | ACGACGCACT | TGTTCAGCGA | GTTGACTTCG | TTTTCCAATA | CCCAAACGCG | 240 |
| GGATCCACGG | CGGGGTAGTT | ACGGTGGGAC | CGACACCTCT | TCCTCCCGAC | GGGGCACACG | 300 |
| TAGTGGCAGT | TGTGGTGGTA | GACACGGCCG | ATGACGGGGT | GGTACTGGGC | GCACGACGTC | 360 |
| CCGCAGGAGG | GCCGGGACGG | AGTCCACCAC | ACGTTGATGG | CGCTACACGC | GAAGCTCAGG | 420 |
| TAGGCCGAGG | GACCGACGGG | CGCGCCGCAC | TTGGGGCACC | AGAGGATGCG | GCACCGAGAG | 480 |
| TCGACAGTTA | CACGTGAGAC | GGCGGCGTCG | TGGTGACTGA | CGCCCCCAGG | GTTCCTGGTG | 540 |
| GGGAACTGGA | CACTACTGGG | GGCGAAGGTC | CTGAGGAGAA | GGAGTTTCCG | GGGAGGGGGG | 600 |
| TCGGAAGGTT | CGGGTAGGGC | TGAGGGCCCC | GGGAGCCTGT | GGGGCTAGGA | GGGTGTTATT | 660 |
| TCCGAAGAGT | TAGGCGTTCG | ACCCCTCGAG | CCTAGGCGCG | CGCAGCTGGG | CGCCAGCTCG | 720 |
| GATCC | | | | | | 725 |

(2) INFORMATION FOR SEQ ID NO:38:

(i) SEQUENCE CHARACTERISTICS:
        (A) LENGTH: 20 amino acids
        (B) TYPE: amino acid (C) STRANDEDNESS: unknown
(D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:38:

```
Met Glu Met Phe Gln Gly Leu Leu Leu Leu Leu Leu Ser Met Gly
1               5                   10                  15
Gly Thr Trp Ala
            20
```

(2) INFORMATION FOR SEQ ID NO:39:

(i) SEQUENCE CHARACTERISTICS:
(A) LENGTH: 5 amino acids
(B) TYPE: amino acid
(C) STRANDEDNESS: unknown
(D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:39:

```
Asp Asp Asp Asp Lys
1               5
```

(2) INFORMATION FOR SEQ ID NO:40:

(i) SEQUENCE CHARACTERISTICS:
(A) LENGTH: 109 amino acids
(B) TYPE: amino acid
(C) STRANDEDNESS: unknown
(D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:40:

```
Met Asp Tyr Tyr Arg Lys Tyr Ala Ala Ile Phe Leu His Val Leu His
1               5                   10                  15

Ser Ala Pro Asp Val Gln Asp Cys Pro Glu Cys Thr Leu Gln Glu Asn
                20                  25                  30

Pro Phe Phe Ser Gln Pro Gly Ala Pro Ile Leu Gln Cys Met Gly Cys
            35                  40                  45

Cys Phe Ser Arg Ala Tyr Pro Thr Pro Leu Arg Ser Lys Lys Thr Met
    50                  55                  60

Leu Val Gln Lys Asp Val Thr Ser Glu Ser Thr Cys Cys Val Ala Lys
65                  70                  75                  80

Ser Tyr Asn Arg Val Thr Val Met Gly Gly Phe Lys Val Glu Asn His
                85                  90                  95

Thr Ala Cys His Cys Ser Thr Cys Tyr Tyr His Lys Ser
                100                 105
```

(2) INFORMATION FOR SEQ ID NO:41:

(i) SEQUENCE CHARACTERISTICS:

(A) LENGTH: 631 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:41:

CTCGAGTCTA GACCCAGCTT GGCAGTCAAC CGCCCTGAAC ACATCCTGCA AAAAGCCCAG      60

AGAAAGGAGC GCCATGGATT ACTACAGAAA ATATGCAGCT ATCTTTCTGC ATGTTCTCCA     120

TTCCGCTCCT GATGTGCAGG ATTGCCCAGA ATGCACGCTA CAGGAAAACC CATTCTTCTC     180

CCAGCCGGGT GCCCCAATAC TTCAGTGCAT GGGCTGCTGC TTCTCTAGAG CATATCCCAC     240

TCCACTAAGA TCTAAGAAGA CTATGTTGGT CCAAAAGGAC GTCACTAGTG AGTCCACTTG     300

CTGTGTAGCT AAATCATATA ACAGGGTCAC AGTAATGGGG GGTTTCAAAG TGGAGAACCA     360

CACGGCGTGC CACTGCAGTA CTTGTTATTA TCACAAATCT TAAATGTTTT ACCAAGTGCT     420

GTCTTGATGA CTGCTGATTT TCTGGAATGG AAAATTAAGT TGTTTAGTGT TTATGGCTTT     480

GTGAGATAAA ACTCTCCTTT TCCTTACCAT ACCACTTTGA CACGCTTCAA GGATATACTG     540

CAGCTTTACT GCCTTCCTCC TTATCCTACA GTACAATCAG CAGTCTAGTT CTTTTCATTT     600

GGAATGAATA CAGCATTAAG CTGGGGGATC C                                   631

(2) INFORMATION FOR SEQ ID NO:42:

(i) SEQUENCE CHARACTERISTICS:
            (A) LENGTH: 631 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:42:

GAGCTCAGAT CTGGGTCGAA CCGTCAGTTG GCGGCACTTG TGTAGGACGT TTTTCGGGTC      60

TCTTTCCTCG CGGTACCTAA TGATGTCTTT TATACGTCGA TAGAAAGACG TACAAGAGGT     120

AAGGCGAGGA CTACACGTCC TAACGGGTCT TACGTGCGAT GTCCTTTTGG GTAAGAAGAG     180

GGTCGGCCCA CGGGGTTATG AAGTCACGTA CCCGACGACG AAGAGATCTC GTATAGGGTG     240

AGGTGATTCT AGATTCTTCT GATACAACCA GGTTTTCCTG CAGTGATGAC TCAGGTGAAC     300

GACACATCGA TTTAGTATAT TGTCCCAGTG TCATTACCCC CCAAAGTTTC ACCTCTTGGT     360

GTGCCGCACG GTGACGTCAT GAACAATAAT AGTGTTTAGA ATTTACAAAA TGGTTCACGA     420

CAGAACTACT GACGACTAAA AGACCTTACC TTTTAATTCA ACAAATCACA AATACCGAAA     480

CACTCTATTT TGAGAGGAAA AGGAATGGTA TGGTGAAACT GTGCGAAGTT CCTATATGAC     540

GTCGAAATGA CGGAAGGAGG AATAGGATGT CATGTTAGTC GTCAGATCAA GAAAAGTAAA     600

CCTTACTTAT GTCGTAATTC GACCCCCTAG G                                   631

(2) INFORMATION FOR SEQ ID NO:43:

(i) SEQUENCE CHARACTERISTICS:
            (A) LENGTH: 151 amino acids (B) TYPE: amino acid
                    (C) STRANDEDNESS: unknown
                    (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:43:

```
Met Glu Met Phe Gln Gly Leu Leu Leu Leu Leu Leu Ser Met Gly
1               5                   10                  15

Gly Thr Trp Ala Ser Cys Gly Gly Leu Thr Asp Thr Leu Gln Ala Glu
            20                  25                  30

Thr Asp Gln Leu Glu Asp Lys Lys Ser Ala Leu Gln Thr Glu Ile Ala
        35                  40                  45

Asn Leu Leu Lys Glu Lys Glu Lys Leu Glu Phe Ile Leu Ala Gly Gln
    50                  55                  60

Asp Cys Pro Glu Cys Thr Leu Gln Glu Asn Pro Phe Phe Ser Gln Pro
65                  70                  75                  80

Gly Ala Pro Ile Leu Gln Cys Met Gly Cys Cys Phe Ser Arg Ala Tyr
                85                  90                  95

Pro Thr Pro Leu Arg Ser Lys Lys Thr Met Leu Val Gln Lys Asp Val
            100                 105                 110

Thr Ser Glu Ser Thr Cys Cys Val Ala Lys Ser Tyr Asn Arg Val Thr
        115                 120                 125

Val Met Gly Gly Phe Lys Val Glu Asn His Thr Ala Cys His Cys Ser
    130                 135                 140

Thr Cys Tyr Tyr His Lys Ser
145                 150
```

(2) INFORMATION FOR SEQ ID NO:44:

(i) SEQUENCE CHARACTERISTICS:
            (A) LENGTH: 729 base pairs
            (B) TYPE: nucleic acid
            (C) STRANDEDNESS: unknown
            (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:44:

```
CTCGAGTCTA GACCCAGCTT AGACAAGGCA GGGGACGCAC CAAGGATGGA GATGTTCCAG      60

GGGCTGCTGC TGTTGCTGCT GCTGAGCATG GGCGGGACAT GGGCTAGCTG TGGTGGGTTA     120

ACCGATACCC TGCAAGCTGA AACTGATCAA CTGGAAGATA AGAAATCTGC TCTGCAAACT     180

GAAATCGCTA ATCTGCTGAA AGAGAAGGAA AAGCTTGAGT TCATCCTGGC CGGCCAAGAT     240

TGTCCGGAAT GCACGCTACA GGAAAACCCA TTCTTCTCCC AGCCGGGTGC CCCAATACTT     300

CAGTGCATGG GCTGCTGCTT CTCTAGAGCA TATCCCACTC CACTAAGATC TAAGAAGACT     360

ATGTTGGTCC AAAAGGACGT CACTAGTGAG TCCACTTGCT GTGTAGCTAA ATCATATAAC     420

AGGGTCACAG TAATGGGGGG TTTCAAAGTG GAGAACCACA CGGCGTGCCA CTGCAGTACT     480

TGTTATTATC ACAAATCTTA AATGTTTTAC CAAGTGCTGT CTTGATGACT GCTGATTTTC     540

TGGAATGGAA AATTAAGTTG TTTAGTGTTT ATGGCTTTGT GAGATAAAAC TCTCCTTTTC     600
```

| | |
|---|---|
| CTTACCATAC CACTTTGACA CGCTTCAAGG ATATACTGCA GCTTTACTGC CTTCCTCCTT | 660 |
| ATCCTACAGT ACAATCAGCA GTCTAGTTCT TTTCATTTGG AATGAATACA GCATTAAGCT | 720 |
| GGGGGATCC | 729 |

(2) INFORMATION FOR SEQ ID NO:45:

(i) SEQUENCE CHARACTERISTICS:
        (A) LENGTH: 729 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:45:

| | |
|---|---|
| GAGCTCAGAT CTGGGTCGAA TCTGTTCCGT CCCCTGCGTG GTTCCTACCT CTACAAGGTC | 60 |
| CCCGACGACG ACAACGACGA CGACTCGTAC CCGCCCTGTA CCCGATCGAC ACCACCCAAT | 120 |
| TGGCTATGGG ACGTTCGACT TGACTAGTT GACCTTCTAT TCTTTAGACG AGACGTTTGA | 180 |
| CTTTAGCGAT TAGACGACTT TCTCTTCCTT TTCGAACTCA AGTAGGACCG GCCGGTTCTA | 240 |
| ACAGGCCTTA CGTGCGATGT CCTTTTGGGT AAGAAGAGGG TCGGCCCACG GGGTTATGAA | 300 |
| GTCACGTACC CGACGACGAA GAGATCTCGT ATAGGGTGAG GTGATTCTAG ATTCTTCTGA | 360 |
| TACAACCAGG TTTTCCTGCA GTGATGACTC AGGTGAACGA CACATCGATT TAGTATATTG | 420 |
| TCCCAGTGTC ATTACCCCCC AAAGTTTCAC CTCTTGGTGT GCCGCACGGT GACGTCATGA | 480 |
| ACAATAATAG TGTTTAGAAT TTACAAAATG GTTCACGACA GAACTACTGA CGACTAAAAG | 540 |
| ACCTTACCTT TTAATTCAAC AAATCACAAA TACCGAAACA CTCTATTTTG AGAGGAAAAG | 600 |
| GAATGGTATG GTGAAACTGT GCGAAGTTCC TATATGACGT CGAAATGACG GAAGGAGGAA | 660 |
| TAGGATGTCA TGTTAGTCGT CAGATCAAGA AAAGTAAACC TTACTTATGT CGTAATTCGA | 720 |
| CCCCCTAGG | 729 |

(2) INFORMATION FOR SEQ ID NO:46:

(i) SEQUENCE CHARACTERISTICS:
        (A) LENGTH: 151 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:46:

```
Met Glu Met Phe Gln Gly Leu Leu Leu Leu Leu Leu Ser Met Gly
 1               5                  10                  15

Gly Thr Trp Ala Ser Cys Gly Gly Leu Thr Asp Thr Leu Gln Ala Glu
              20                  25                  30

Thr Asp Gln Leu Glu Asp Lys Lys Ser Ala Leu Gln Thr Glu Ile Ala
          35                  40                  45

Asn Leu Leu Lys Glu Lys Glu Lys Leu Glu Phe Ile Leu Ala Gly Gln
      50                  55                  60

Asp Ala Pro Glu Cys Thr Leu Gln Glu Asn Pro Phe Phe Ser Gln Pro
```

```
            65                  70                  75                  80
Gly Ala Pro Ile Leu Gln Cys Met Gly Cys Cys Phe Ser Arg Ala Tyr
                        85                  90                  95

Pro Thr Pro Leu Arg Ser Lys Lys Thr Met Leu Val Gln Lys Asn Val
                100                 105                 110

Thr Ser Glu Ser Thr Cys Cys Val Ala Lys Ser Tyr Asn Arg Val Thr
            115                 120                 125

Val Met Gly Gly Phe Lys Val Glu Asn His Thr Ala Cys His Cys Ser
    130                 135                 140

Thr Cys Tyr Tyr His Lys Ser
145                 150
```

(2) INFORMATION FOR SEQ ID NO:47:

(i) SEQUENCE CHARACTERISTICS:
        (A) LENGTH: 729 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:47:

```
CTCGAGTCTA GACCCAGCTT AGACAAGGCA GGGGACGCAC CAAGGATGGA GATGTTCCAG    60
GGGCTGCTGC TGTTGCTGCT GCTGAGCATG GGCGGGACAT GGGCTAGCTG TGGTGGGTTA   120
ACCGATACCC TGCAAGCTGA AACTGATCAA CTGGAAGATA AGAAATCTGC TCTGCAAACT   180
GAAATCGCTA ATCTGCTGAA AGAGAAGGAA AAGCTTGAGT TCATCCTGGC CGGCCAAGAT   240
GCTCCGGAAT GCACGCTACA GGAAAACCCA TTCTTCTCCC AGCCGGGTGC CCCAATACTT   300
CAGTGCATGG GCTGCTGCTT CTCTAGAGCA TATCCCACTC CACTAAGGTC AAGAAGACG    360
ATGTTGGTCC AAAAGAACGT CACCTCAGAG TCCACTTGCT GTGTAGCTAA ATCATATAAC   420
AGGGTCACAG TAATGGGGGG TTTCAAAGTG GAGAACCACA CGGCGTGCCA CTGCAGTACT   480
TGTTATTATC ACAAATCTTA AATGTTTTAC CAAGTGCTGT CTTGATGACT GCTGATTTTC   540
TGGAATGGAA AATTAAGTTG TTTAGTGTTT ATGGCTTTGT GAGATAAAAC TCTCCTTTTC   600
CTTACCATAC CACTTTGACA CGCTTCAAGG ATATACTGCA GCTTTACTGC CTTCCTCCTT   660
ATCCTACAGT ACAATCAGCA GTCTAGTTCT TTTCATTTGG AATGAATACA GCATTAAGCT   720
GGGGGATCC                                                          729
```

(2) INFORMATION FOR SEQ ID NO:48:

(i) SEQUENCE CHARACTERISTICS:
        (A) LENGTH: 729 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:48:

```
GAGCTCAGAT CTGGGTCGAA TCTGTTCCGT CCCCTGCGTG GTTCCTACCT CTACAAGGTC    60
```

-continued

```
CCCGACGACG ACAACGACGA CGACTCGTAC CCGCCCTGTA CCCGATCGAC ACCACCCAAT    120

TGGCTATGGG ACGTTCGACT TTGACTAGTT GACCTTCTAT TCTTTAGACG AGACGTTTGA    180

CTTTAGCGAT TAGACGACTT TCTCTTCCTT TTCGAACTCA AGTAGGACCG GCCGGTTCTA    240

CGAGGCCTTA CGTGCGATGT CCTTTTGGGT AAGAAGAGGG TCGGCCCACG GGGTTATGAA    300

GTCACGTACC CGACGACGAA GAGATCTCGT ATAGGGTGAG GTGATTCCAG GTTCTTCTGC    360

TACAACCAGG TTTTCTTGCA GTGGAGTCTC AGGTGAACGA CACATCGATT TAGTATATTG    420

TCCCAGTGTC ATTACCCCCC AAAGTTTCAC CTCTTGGTGT GCCGCACGGT GACGTCATGA    480

ACAATAATAG TGTTTAGAAT TTACAAAATG GTTCACGACA GAACTACTGA CGACTAAAAG    540

ACCTTACCTT TTAATTCAAC AAATCACAAA TACCGAAACA CTCTATTTTG AGAGGAAAAG    600

GAATGGTATG GTGAAACTGT GCGAAGTTCC TATATGACGT CGAAATGACG GAAGGAGGAA    660

TAGGATGTCA TGTTAGTCGT CAGATCAAGA AAAGTAAACC TTACTTATGT CGTAATTCGA    720

CCCCCTAGG                                                            729
```

(2) INFORMATION FOR SEQ ID NO:49:

(i) SEQUENCE CHARACTERISTICS:
        (A) LENGTH: 204 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:49:

```
Met Glu Met Phe Gln Gly Leu Leu Leu Leu Leu Leu Ser Met Gly
 1               5                  10                  15

Gly Thr Trp Ala Ser Cys Gly Gly Arg Ile Ala Arg Leu Glu Glu Lys
            20                  25                  30

Val Lys Thr Leu Lys Ala Gln Asn Ser Glu Leu Ala Ser Thr Ala Asn
        35                  40                  45

Met Leu Arg Glu Gln Val Ala Gln Leu Lys Gln Lys Val Met Gly Leu
    50                  55                  60

Arg Pro Arg Cys Arg Pro Ile Asn Ala Thr Leu Ala Val Glu Lys Glu
65                  70                  75                  80

Gly Cys Pro Val Cys Ile Thr Val Asn Thr Thr Ile Cys Ala Gly Tyr
                85                  90                  95

Cys Pro Thr Met Thr Arg Val Leu Gln Gly Val Leu Pro Ala Leu Pro
                100                 105                 110

Gln Val Val Cys Asn Tyr Arg Asp Val Arg Phe Glu Ser Ile Arg Leu
            115                 120                 125

Pro Gly Cys Pro Arg Gly Val Asn Pro Val Val Ser Tyr Ala Val Ala
    130                 135                 140

Leu Ser Cys Gln Cys Ala Leu Cys Arg Arg Ser Thr Thr Asp Cys Gly
145                 150                 155                 160

Gly Pro Lys Asp His Pro Leu Thr Cys Asp Asp Pro Arg Phe Gln Asp
                165                 170                 175

Ser Ser Ser Ser Lys Ala Pro Pro Ser Leu Pro Ser Pro Ser Arg
                180                 185                 190

Leu Pro Gly Pro Ser Asp Thr Pro Ile Leu Pro Gln
            195                 200
```

(2) INFORMATION FOR SEQ ID NO:50:

(i) SEQUENCE CHARACTERISTICS:
        (A) LENGTH: 725 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:50:

```
CTCGAGTCTA GACCCAGCTT AGACAAGGCA GGGGACGCAC CAAGGATGGA GATGTTCCAG      60
GGGCTGCTGC TGTTGCTGCT GCTGAGCATG GGCGGGACAT GGGCTAGCTG TGGCGGCCGC     120
ATTGCTAGAT TGGAAGAGAA AGTTAAAACT CTGAAGGCCC AAAACAGCGA ACTGGCTTCC     180
ACTGCTAATA TGCTGCGTGA ACAAGTCGCT CAACTGAAGC AAAAGGTTAT GGGTTTGCGC     240
CCTAGGTGCC GCCCCATCAA TGCCACCCTG GCTGTGGAGA AGGAGGGCTG CCCCGTGTGC     300
ATCACCGTCA ACACCACCAT CTGTGCCGGC TGTTGTCCTA CCATGACACG TGTGCTGCAG     360
GGCGTCCTCC CGGCCCTGCC TCAGGTGGTG TGCAACTACC GCGATGTGCG CTTCGAGTCC     420
ATCCGGCTCC CTGGCTGCCC GCGCGGCGTG AACCCCGTGG TCTCCTACGC CGTGGCTCTC     480
AGCTGTCAAT GTGCACTCTG CCGCCGCAGC ACCACTGACT GCGGGGGTCC CAAGGACCAC     540
CCCTTGACCT GTGATGACCC CCGCTTCCAG GACTCCTCTT CCTCAAAGGC CCCTCCCCCC     600
AGCCTTCCAA GCCCATCCCG ACTCCCGGGG CCCTCGGACA CCCCGATCCT CCCACAATAA     660
AGGCTTCTCA ATCCGCAAGC TGGGGAGCTC GGATCCGCGC GCGTCGACCC GCGGAGCTCG     720
GATCC                                                                725
```

(2) INFORMATION FOR SEQ ID NO:51:

(i) SEQUENCE CHARACTERISTICS:
        (A) LENGTH: 725 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:51:

```
GAGCTCAGAT CTGGGTCGAA TCTGTTCCGT CCCCTGCGTG GTTCCTACCT CTACAAGGTC      60
CCCGACGACG ACAACGACGA CGACTCGTAC CCGCCCTGTA CCCGATCGAC ACCGCCGGCG     120
TAACGATCTA ACCTTCTCTT TCAATTTTGA GACTTCCGGG TTTTGTCGCT TGACCGAAGG     180
TGACGATTAT ACGACGCACT TGTTCAGCGA GTTGACTTCG TTTTCCAATA CCCAAACGCG     240
GGATCCACGG CGGGGTAGTT ACGGTGGGAC CGACACCTCT TCCTCCCGAC GGGGCACACG     300
TAGTGGCAGT TGTGGTGGTA GACACGGCCG ACAACAGGAT GGTACTGTGC ACACGACGTC     360
CCGCAGGAGG GCCGGGACGG AGTCCACCAC ACGTTGATGG CGCTACACGC GAAGCTCAGG     420
TAGGCCGAGG GACCGACGGG CGCGCCGCAC TTGGGGCACC AGAGGATGCG GCACCGAGAG     480
TCGACAGTTA CACGTGAGAC GGCGGCGTCG TGGTGACTGA CGCCCCCAGG GTTCCTGGTG     540
```

```
GGGAACTGGA CACTACTGGG GGCGAAGGTC CTGAGGAGAA GGAGTTTCCG GGGAGGGGGG      600

TCGGAAGGTT CGGGTAGGGC TGAGGGCCCC GGGAGCCTGT GGGGCTAGGA GGGTGTTATT      660

TCCGAAGAGT TAGGCGTTCG ACCCCTCGAG CCTAGGCGCG CGCAGCTGGG CGCCTCGAGC      720

CTAGG                                                                 725
```

(2) INFORMATION FOR SEQ ID NO:52:

(i) SEQUENCE CHARACTERISTICS:
        (A) LENGTH: 4 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:52:

```
Ile Glu Gly Arg
1
```

(2) INFORMATION FOR SEQ ID NO:53:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:53:

```
Ala Leu Ala Pro Arg Ala Ser Pro Val Ala Leu
1               5                   10
```

(2) INFORMATION FOR SEQ ID NO:54:

(i) SEQUENCE CHARACTERISTICS:
        (A) LENGTH: 204 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:54:

```
Met Glu Met Phe Gln Gly Leu Leu Leu Leu Leu Leu Ser Met Gly
1               5                   10                  15

Gly Thr Trp Ala Ser Cys Gly Gly Arg Ile Ala Arg Leu Glu Glu Lys
                20                  25                  30

Val Lys Thr Leu Lys Ala Gln Asn Ser Glu Leu Ala Ser Thr Ala Asn
            35                  40                  45

Met Leu Arg Glu Gln Val Ala Gln Leu Lys Gln Lys Val Met Gly Leu
        50                  55                  60

Arg Pro Arg Cys Arg Pro Ile Asn Ala Thr Leu Ala Val Glu Lys Glu
65                  70                  75                  80
```

```
Gly Cys Pro Val Ala Ile Thr Val Asn Thr Thr Ile Cys Ala Gly Tyr
                85                  90                  95
Cys Pro Thr Met Thr Arg Val Leu Gln Gly Val Leu Pro Ala Leu Pro
            100                 105                 110
Gln Val Val Cys Asn Tyr Arg Asp Val Arg Phe Glu Ser Ile Arg Leu
            115                 120                 125
Pro Gly Cys Pro Arg Gly Val Asn Pro Val Val Ser Tyr Ala Val Ala
            130                 135                 140
Leu Ser Cys Gln Cys Ala Leu Cys Arg Arg Ser Thr Thr Asp Cys Gly
145                 150                 155                 160
Gly Pro Lys Asp His Pro Leu Thr Cys Asp Asp Pro Arg Phe Gln Asp
                165                 170                 175
Ser Ser Ser Ser Lys Ala Pro Pro Ser Leu Pro Ser Pro Ser Arg
                180                 185                 190
Leu Pro Gly Pro Ser Asp Thr Pro Ile Leu Pro Gln
            195                 200
```

(2) INFORMATION FOR SEQ ID NO:55:

(i) SEQUENCE CHARACTERISTICS:
        (A) LENGTH: 725 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:55:

```
CTCGAGTCTA GACCCAGCTT AGACAAGGCA GGGGACGCAC CAAGGATGGA GATGTTCCAG    60
GGGCTGCTGC TGTTGCTGCT GCTGAGCATG GGCGGGACAT GGGCTAGCTG TGGCGGCCGC   120
ATTGCTAGAT TGGAAGAGAA AGTTAAAACT CTGAAGGCCC AAAACAGCGA ACTGGCTTCC   180
ACTGCTAATA TGCTGCGTGA CAAGTCGCT CAACTGAAGC AAAAGGTTAT GGGTTTGCGC   240
CCTAGGTGTC GTCCTATTAA TGCTACTCTG GCTGTTGAGA AGGAAGGTTG TCCTGTGGCC   300
ATTACTGTTA ACACTACCAT CTGTGCCGGC TGTTGTCCTA CCATGACACG TGTGCTGCAG   360
GGCGTCCTCC CGGCCCTGCC TCAGGTGGTG TGCAACTACC GCGATGTGCG CTTCGAGTCC   420
ATCCGGCTCC CTGGCTGCCC GCGCGGCGTG AACCCCGTGG TCTCCTACGC CGTGGCTCTC   480
AGCTGTCAAT GTGCACTCTG CCGCCGCAGC ACCACTGACT GCGGGGGTCC CAAGGACCAC   540
CCCTTGACCT GTGATGACCC CCGCTTCCAG GACTCCTCTT CCTCAAAGGC CCCTCCCCCC   600
AGCCTTCCAA GCCCATCCCG ACTCCCGGGG CCCTCGGACA CCCCGATCCT CCCACAATAA   660
AGGCTTCTCA ATCCGCAAGC TGGGGAGCTC GGATCCGCGC GCGTCGACCC GCGGAGCTCG   720
GATCC                                                              725
```

(2) INFORMATION FOR SEQ ID NO:56:

(i) SEQUENCE CHARACTERISTICS:
        (A) LENGTH: 725 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:56:

```
GAGCTCAGAT CTGGGTCGAA TCTGTTCCGT CCCCTGCGTG GTTCCTACCT CTACAAGGTC      60

CCCGACGACG ACAACGACGA CGACTCGTAC CCGCCCTGTA CCCGATCGAC ACCGCCGGCG     120

TAACGATCTA ACCTTCTCTT TCAATTTTGA GACTTCCGGG TTTTGTCGCT TGACCGAAGG     180

TGACGATTAT ACGACGCACT TGTTCAGCGA GTTGACTTCG TTTTCCAATA CCCAAACGCG     240

GGATCCACAG CAGGATAATT ACGATGAGAC CGACAACTCT TCCTTCCAAC AGGACACCGG     300

TAATGACAAT TGTGATGGTA GACACGGCCG ACAACAGGAT GGTACTGTGC ACACGACGTC     360

CCGCAGGAGG GCCGGGACGG AGTCCACCAC ACGTTGATGG CGCTACACGC GAAGCTCAGG     420

TAGGCCGAGG GACCGACGGG CGCGCCGCAC TTGGGGCACC AGAGGATGCG GCACCGAGAG     480

TCGACAGTTA CACGTGAGAC GGCGGCGTCG TGGTGACTGA CGCCCCCAGG GTTCCTGGTG     540

GGGAACTGGA CACTACTGGG GGCGAAGGTC CTGAGGAGAA GGAGTTTCCG GGAGGGGGG     600

TCGGAAGGTT CGGGTAGGGC TGAGGGCCCC GGGAGCCTGT GGGGCTAGGA GGGTGTTATT     660

TCCGAAGAGT TAGGCGTTCG ACCCCTCGAG CCTAGGCGCG CGCAGCTGGG CGCCTCGAGC     720

CTAGG                                                                 725
```

(2) INFORMATION FOR SEQ ID NO:57:

(i) SEQUENCE CHARACTERISTICS:
            (A) LENGTH: 15 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:57:

```
Ser Glu Arg Leu Tyr Ser Gly Leu Pro Arg Leu Glu Ala Arg Gly
1               5                  10                  15
```

(2) INFORMATION FOR SEQ ID NO:58:

(i) SEQUENCE CHARACTERISTICS:
            (A) LENGTH: 212 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:58:

```
Met Glu Met Phe Gln Gly Leu Leu Leu Leu Leu Leu Ser Met Gly
1               5                  10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
```

```
            50                  55                  60
Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                 85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
                115                 120                 125

Thr Cys Asp Asp Pro Arg Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln Gly Ser Gly Ser Gly Ser Cys Gly Gly Arg Ile
                165                 170                 175

Ala Arg Leu Glu Glu Lys Val Lys Thr Leu Lys Ala Gln Asn Ser Glu
                180                 185                 190

Leu Ala Ser Thr Ala Asn Met Leu Arg Glu Gln Val Ala Gln Leu Lys
                195                 200                 205

Gln Lys Val Met
    210

(2) INFORMATION FOR SEQ ID NO:59:

(i) SEQUENCE CHARACTERISTICS:
        (A) LENGTH: 151 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:59:

Met Glu Met Phe Gln Gly Leu Leu Leu Leu Leu Leu Ser Met Gly
  1               5                  10                  15

Gly Thr Trp Ala Ser Cys Gly Gly Arg Ile Ala Arg Leu Glu Glu Lys
                 20                  25                  30

Val Lys Thr Leu Lys Ala Gln Asn Ser Glu Leu Ala Ser Thr Ala Asn
                 35                  40                  45

Met Leu Arg Glu Gln Val Ala Gln Leu Lys Gln Lys Val Met Gly Leu
 50                  55                  60

Arg Pro Arg Cys Arg Pro Ile Asn Ala Thr Leu Ala Val Glu Lys Glu
 65                  70                  75                  80

Gly Cys Pro Val Ala Ile Thr Val Asn Thr Thr Ile Cys Ala Gly Tyr
                 85                  90                  95

Cys Pro Thr Met Thr Arg Val Leu Gln Gly Val Leu Pro Ala Leu Pro
                100                 105                 110

Gln Val Val Cys Asn Tyr Arg Asp Val Arg Phe Glu Ser Ile Arg Leu
                115                 120                 125

Pro Gly Cys Pro Arg Gly Val Asn Pro Val Val Ser Tyr Ala Val Ala
                130                 135                 140

Leu Ser Cys Gln Cys Ala Leu
145                 150
```

(2) INFORMATION FOR SEQ ID NO:60:

(i) SEQUENCE CHARACTERISTICS:
      (A) LENGTH: 508 base pairs
      (B) TYPE: nucleic acid
      (C) STRANDEDNESS: unknown
      (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:60:

```
CTCGAGTCTA GACCCAGCTT AGACAAGGCA GGGGACGCAC CAAGGATGGA GATGTTCCAG      60
GGGCTGCTGC TGTTGCTGCT GCTGAGCATG GGCGGGACAT GGGCTAGCTG TGGCGGCCGC     120
ATTGCTAGAT TGGAAGAGAA AGTTAAAACT CTGAAGGCCC AAAACAGCGA ACTGGCTTCC     180
ACTGCTAATA TGCTGCGTGA ACAAGTCGCT CAACTGAAGC AAAAGGTTAT GGGTTTGCGC     240
CCTAGGTGTC GTCCTATTAA TGCTACTCTG GCTGTTGAGA AGGAAGGTTG TCCTGTGGCC     300
ATTACTGTTA ACACTACCAT CTGTGCCGGC TGTTGTCCTA CCATGACACG TGTGCTGCAG     360
GGCGTCCTCC CGGCCCTGCC TCAGGTGGTG TGCAACTACC GCGATGTGCG CTTCGAGTCC     420
ATCCGGCTCC CTGGCTGCCC GCGCGGCGTG AACCCCGTGG TCTCCTACGC CGTGGCTCTC     480
AGCTGTCAAT GCGCGCTTTA AAGGATCC                                        508
```

(2) INFORMATION FOR SEQ ID NO:61:

(i) SEQUENCE CHARACTERISTICS:
      (A) LENGTH: 508 base pairs
      (B) TYPE: nucleic acid
      (C) STRANDEDNESS: unknown
      (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:61:

```
GAGCTCAGAT CTGGGTCGAA TCTGTTCCGT CCCCTGCGTG GTTCCTACCT CTACAAGGTC      60
CCCGACGACG ACAACGACGA CGACTCGTAC CCGCCCTGTA CCCGATCGAC ACCGCCGGCG     120
TAACGATCTA ACCTTCTCTT TCAATTTTGA GACTTCCGGG TTTTGTCGCT TGACCGAAGG     180
TGACGATTAT ACGACGCACT TGTTCAGCGA GTTGACTTCG TTTTCCAATA CCCAAACGCG     240
GGATCCACAG CAGGATAATT ACGATGAGAC CGACAACTCT TCCTTCCAAC AGGACACCGG     300
TAATGACAAT TGTGATGGTA GACACGGCCG ACAACAGGAT GGTACTGTGC ACACGACGTC     360
CCGCAGGAGG GCCGGGACGG AGTCCACCAC ACGTTGATGG CGCTACACGC GAAGCTCAGG     420
TAGGCCGAGG GACCGACGGG CGCGCCGCAC TTGGGGCACC AGAGGATGCG GCACCGAGAG     480
TCGACAGTTA CGCGCGAAAT TTCCTAGG                                        508
```

(2) INFORMATION FOR SEQ ID NO:62:

(i) SEQUENCE CHARACTERISTICS:
      (A) LENGTH: 155 amino acids
      (B) TYPE: amino acid
      (C) STRANDEDNESS: unknown
      (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:62:

Met Glu Met Phe Gln Gly Leu Leu Leu Leu Leu Leu Ser Met Gly
1               5                   10                  15

Gly Thr Trp Ala Ser Cys Gly Gly Leu Thr Asp Thr Leu Gln Ala Glu
            20                  25                  30

Thr Asp Gln Leu Glu Asp Lys Lys Ser Ala Leu Gln Thr Glu Ile Ala
            35                  40                  45

Asn Leu Leu Lys Glu Lys Glu Lys Leu Glu Phe Ile Leu Ala Gly Lys
        50                  55                  60

Ser Lys Arg Gln Asp Cys Pro Glu Cys Thr Leu Gln Glu Asn Pro Phe
65                  70                  75                  80

Phe Ser Gln Pro Gly Ala Pro Ile Leu Gln Cys Met Gly Cys Cys Phe
                85                  90                  95

Ser Arg Ala Tyr Pro Thr Pro Leu Arg Ser Lys Lys Thr Met Leu Val
            100                 105                 110

Gln Lys Asn Val Thr Ser Glu Ser Thr Cys Cys Val Ala Lys Ser Tyr
        115                 120                 125

Asn Arg Val Thr Val Met Gly Gly Phe Lys Val Glu Asn His Thr Ala
    130                 135                 140

Cys His Cys Ser Thr Cys Tyr Tyr His Lys Ser
145                 150                 155

(2) INFORMATION FOR SEQ ID NO:63:

(i) SEQUENCE CHARACTERISTICS:
            (A) LENGTH: 208 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:63:

Met Glu Met Phe Gln Gly Leu Leu Leu Leu Leu Leu Ser Met Gly
1               5                   10                  15

Gly Thr Trp Ala Ser Cys Gly Gly Arg Ile Ala Arg Leu Glu Glu Lys
            20                  25                  30

Val Lys Thr Leu Lys Ala Gln Asn Ser Glu Leu Ala Ser Thr Ala Asn
            35                  40                  45

Met Leu Arg Glu Gln Val Ala Gln Leu Lys Gln Lys Val Met Gly Lys
        50                  55                  60

Ser Lys Arg Leu Arg Pro Arg Cys Arg Pro Ile Asn Ala Thr Leu Ala
65                  70                  75                  80

Val Glu Lys Glu Gly Cys Pro Val Cys Ile Thr Val Asn Thr Thr Ile
                85                  90                  95

Cys Ala Gly Tyr Cys Pro Thr Met Thr Arg Val Leu Gln Gly Val Leu
            100                 105                 110

Pro Ala Leu Pro Gln Val Val Cys Asn Tyr Arg Asp Val Arg Phe Glu
        115                 120                 125

```
Ser Ile Arg Leu Pro Gly Cys Pro Arg Gly Val Asn Pro Val Val Ser
130                 135                 140
Tyr Ala Val Ala Leu Ser Cys Gln Cys Ala Leu Cys Arg Arg Ser Thr
145                 150                 155                 160
Thr Asp Cys Gly Gly Pro Lys Asp His Pro Leu Thr Cys Asp Asp Pro
                165                 170                 175
Arg Phe Gln Asp Ser Ser Ser Lys Ala Pro Pro Ser Leu Pro
            180                 185                 190
Ser Pro Ser Arg Leu Pro Gly Pro Ser Asp Thr Pro Ile Leu Pro Gln
                195                 200                 205
```

(2) INFORMATION FOR SEQ ID NO:64:

(i) SEQUENCE CHARACTERISTICS:
  (A) LENGTH: 159 amino acids
  (B) TYPE: amino acid
  (C) STRANDEDNESS: unknown
  (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:64:

```
Met Glu Met Phe Gln Gly Leu Leu Leu Leu Leu Leu Ser Met Gly
1               5                   10                  15
Gly Thr Trp Ala Ser Cys Gly Gly Leu Thr Asp Thr Leu Gln Ala Glu
                20                  25                  30
Thr Asp Gln Leu Glu Asp Lys Lys Ser Ala Leu Gln Thr Glu Ile Ala
                35                  40                  45
Asn Leu Leu Lys Glu Lys Glu Lys Leu Glu Phe Ile Leu Ala Gly Lys
50                  55                  60
Ser Lys Arg Ala Pro Asp Val Gln Asp Cys Pro Glu Cys Thr Leu Gln
65                  70                  75                  80
Glu Asn Pro Phe Phe Ser Gln Pro Gly Ala Pro Ile Leu Gln Cys Met
                85                  90                  95
Gly Cys Cys Phe Ser Arg Ala Tyr Pro Thr Pro Leu Arg Ser Lys Lys
                100                 105                 110
Thr Met Leu Val Gln Lys Asn Val Thr Ser Glu Ser Thr Cys Cys Val
            115                 120                 125
Ala Lys Ser Tyr Asn Arg Val Thr Val Met Gly Gly Phe Lys Val Glu
130                 135                 140
Asn His Thr Ala Cys His Cys Ser Thr Cys Tyr Tyr His Lys Ser
145                 150                 155
```

(2) INFORMATION FOR SEQ ID NO:65:

(i) SEQUENCE CHARACTERISTICS:
  (A) LENGTH: 212 amino acids
  (B) TYPE: amino acid
  (C) STRANDEDNESS: unknown
  (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:65:

-continued

```
Met Glu Met Phe Gln Gly Leu Leu Leu Leu Leu Leu Ser Met Gly
1               5                   10                  15

Gly Thr Trp Ala Ser Cys Gly Gly Arg Ile Ala Arg Leu Glu Glu Lys
            20                  25                  30

Val Lys Thr Leu Lys Ala Gln Asn Ser Glu Leu Ala Ser Thr Ala Asn
                35                  40                  45

Met Leu Arg Glu Gln Val Ala Gln Leu Lys Gln Lys Val Met Gly Lys
    50                  55                  60

Ser Lys Arg Ser Lys Glu Pro Leu Arg Pro Arg Cys Arg Pro Ile Asn
65                  70                  75                  80

Ala Thr Leu Ala Val Glu Lys Glu Gly Cys Pro Val Cys Ile Thr Val
                85                  90                  95

Asn Thr Thr Ile Cys Ala Gly Tyr Cys Pro Thr Met Thr Arg Val Leu
                100                 105                 110

Gln Gly Val Leu Pro Ala Leu Pro Gln Val Val Cys Asn Tyr Arg Asp
            115                 120                 125

Val Arg Phe Glu Ser Ile Arg Leu Pro Gly Cys Pro Arg Gly Val Asn
    130                 135                 140

Pro Val Val Ser Tyr Ala Val Ala Leu Ser Cys Gln Cys Ala Leu Cys
145                 150                 155                 160

Arg Arg Ser Thr Thr Asp Cys Gly Gly Pro Lys Asp His Pro Leu Thr
                165                 170                 175

Cys Asp Asp Pro Arg Phe Gln Asp Ser Ser Ser Lys Ala Pro Pro
            180                 185                 190

Pro Ser Leu Pro Ser Pro Ser Arg Leu Pro Gly Pro Ser Asp Thr Pro
            195                 200                 205

Ile Leu Pro Gln
    210
```

(2) INFORMATION FOR SEQ ID NO:66:

(i) SEQUENCE CHARACTERISTICS:
        (A) LENGTH: 181 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:66:

```
Met Glu Met Phe Gln Gly Leu Leu Leu Leu Leu Leu Ser Met Gly
1               5                   10                  15

Gly Thr Trp Ala Ser Cys Gly Gly Arg Ile Ala Arg Leu Glu Glu Lys
            20                  25                  30

Val Lys Thr Leu Lys Ala Gln Asn Ser Glu Leu Ala Ser Thr Ala Asn
                35                  40                  45

Met Leu Arg Glu Gln Val Ala Gln Leu Lys Gln Lys Val Met Gly Lys
    50                  55                  60

Ser Lys Arg Ser Arg Glu Pro Leu Arg Pro Trp Cys His Pro Ile Asn
65                  70                  75                  80

Ala Ile Leu Ala Val Glu Lys Glu Gly Cys Pro Val Cys Ile Thr Val
                85                  90                  95

Asn Thr Thr Ile Cys Ala Gly Tyr Cys Pro Thr Met Met Arg Val Leu
                100                 105                 110
```

```
Gln Ala Val Leu Pro Pro Leu Pro Gln Val Val Cys Thr Tyr Arg Asp
        115                 120                 125

Val Arg Phe Glu Ser Ile Arg Leu Pro Gly Cys Pro Arg Gly Val Asp
130                 135                 140

Pro Val Val Ser Phe Pro Val Ala Leu Ser Cys Arg Cys Ala Leu Cys
145                 150                 155                 160

Arg Arg Ser Thr Ser Asp Cys Gly Gly Pro Lys Asp His Pro Leu Thr
                165                 170                 175

Cys Asp His Pro Gln
            180
```

(2) INFORMATION FOR SEQ ID NO:67:

(i) SEQUENCE CHARACTERISTICS:
        (A) LENGTH: 184 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:67:

```
Met Glu Met Phe Gln Gly Leu Leu Leu Leu Leu Ser Met Gly
1               5                   10                  15
                                                            Gly
Gly Thr Trp Ala Ser Cys Gly Gly Arg Ile Ala Arg Leu Glu Glu Lys
            20                  25                  30

Val Lys Thr Leu Lys Ala Gln Asn Ser Glu Leu Ala Ser Thr Ala Asn
        35                  40                  45

Met Leu Arg Glu Gln Val Ala Gln Leu Lys Gln Lys Val Met Gly Ser
    50                  55                  60

Lys Glu Pro Leu Arg Lys Ser Lys Arg Asn Ser Cys Glu Leu Thr Asn
65              70                  75                      80

Ile Thr Ile Ala Ile Glu Lys Glu Glu Cys Arg Phe Cys Ile Ser Ile
                85                  90                  95

Asn Thr Thr Trp Cys Ala Gly Tyr Cys Tyr Thr Arg Asp Leu Val Tyr
                100                 105                 110

Lys Asp Pro Ala Arg Pro Lys Ile Gln Lys Thr Cys Thr Phe Lys Glu
            115                 120                 125

Leu Val Tyr Glu Thr Val Arg Val Pro Gly Cys Ala His His Ala Asp
130                 135                 140

Ser Leu Tyr Thr Tyr Pro Val Ala Thr Gln Cys His Cys Gly Lys Cys
145                 150                 155                 160

Asp Ser Asp Ser Thr Asp Cys Thr Val Arg Gly Leu Gly Pro Ser Tyr
                165                 170                 175

Cys Ser Phe Gly Glu Met Lys Glu
            180
```

(2) INFORMATION FOR SEQ ID NO:68:

(i) SEQUENCE CHARACTERISTICS:
        (A) LENGTH: 186 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:68:

```
Met Glu Met Phe Gln Gly Leu Leu Leu Leu Leu Leu Ser Met Gly
1               5                   10                  15

Gly Thr Trp Ala Ser Cys Gly Gly Arg Ile Ala Arg Leu Glu Glu Lys
            20                  25                  30

Val Lys Thr Leu Lys Ala Gln Asn Ser Glu Leu Ala Ser Thr Ala Asn
                35                  40                  45

Met Leu Arg Glu Gln Val Ala Gln Leu Lys Gln Lys Val Met Gly Ser
        50                  55                  60

Lys Glu Pro Leu Arg Gly Lys Ser Lys Arg Phe Cys Ile Pro Thr Glu
65                  70                  75                  80

Tyr Thr Met His Ile Glu Arg Arg Glu Cys Ala Tyr Cys Leu Thr Ile
                85                  90                  95

Asn Thr Thr Ile Cys Ala Gly Tyr Cys Met Thr Arg Asp Ile Asn Gly
                100                 105                 110

Lys Leu Phe Leu Pro Lys Tyr Ala Leu Ser Gln Asp Val Cys Thr Tyr
            115                 120                 125

Arg Asp Phe Ile Tyr Arg Thr Val Glu Ile Pro Gly Cys Pro Leu His
    130                 135                 140

Val Ala Pro Tyr Phe Ser Tyr Pro Val Ala Leu Ser Cys Lys Cys Gly
145                 150                 155                 160

Lys Cys Asn Thr Asp Tyr Ser Asp Cys Ile His Glu Ala Ile Lys Thr
                165                 170                 175

Asn Tyr Cys Thr Lys Pro Gln Lys Ser Tyr
            180                 185
```

(2) INFORMATION FOR SEQ ID NO:69:

(i) SEQUENCE CHARACTERISTICS:
(A) LENGTH: 212 amino acids
(B) TYPE: amino acid
(C) STRANDEDNESS: unknown
(D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:69:

```
Met Glu Met Phe Gln Gly Leu Leu Leu Leu Leu Leu Ser Met Gly
1               5                   10                  15

Gly Thr Trp Ala Ser Cys Gly Gly Arg Ile Ala Arg Leu Glu Glu Lys
            20                  25                  30

Val Lys Thr Leu Lys Ala Gln Asn Ser Glu Leu Ala Ser Thr Ala Asn
                35                  40                  45

Met Leu Arg Glu Gln Val Ala Gln Leu Lys Gln Lys Val Met Gly Lys
        50                  55                  60

Ser Lys Arg Ser Lys Glu Pro Leu Arg Pro Arg Cys Arg Pro Ile Asn
65                  70                  75                  80

Ala Thr Leu Ala Val Glu Lys Glu Gly Cys Pro Val Cys Ile Thr Val
                85                  90                  95

Asn Thr Thr Ile Cys Ala Gly Tyr Cys Pro Thr Met Thr Arg Val Leu
```

```
                100                 105                 110
Gln Gly Val Leu Pro Ala Leu Pro Gln Val Val Cys Asn Tyr Arg Asp
        115                 120                 125
Val Arg Phe Glu Ser Ile Arg Leu Pro Gly Cys Pro Arg Gly Val Asn
        130                 135                 140
Pro Val Val Ser Tyr Ala Val Ala Leu Ser Cys Gln Cys Ala Leu Cys
145                 150                 155                 160
Asp Ser Asp Ser Thr Asp Cys Thr Val Arg Gly Leu Gly Pro Ser Tyr
                165                 170                 175
Cys Ser Phe Gly Glu Met Lys Glu Ser Ser Ser Lys Ala Pro Pro
                180                 185                 190
Pro Ser Leu Pro Ser Pro Ser Arg Leu Pro Gly Pro Ser Asp Thr Pro
        195                 200                 205
Ile Leu Pro Gln
        210

(2) INFORMATION FOR SEQ ID NO:70:

(i) SEQUENCE CHARACTERISTICS:
        (A) LENGTH: 212 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:70:

Met Glu Met Phe Gln Gly Leu Leu Leu Leu Leu Leu Ser Met Gly
1               5                   10                  15
Gly Thr Trp Ala Ser Cys Gly Gly Arg Ile Ala Arg Leu Glu Glu Lys
                20                  25                  30
Val Lys Thr Leu Lys Ala Gln Asn Ser Glu Leu Ala Ser Thr Ala Asn
        35                  40                  45
Met Leu Arg Glu Gln Val Ala Gln Leu Lys Gln Lys Val Met Gly Lys
    50                  55                  60
Ser Lys Arg Ser Lys Glu Pro Leu Arg Pro Arg Cys Arg Pro Ile Asn
65                  70                  75                  80
Ala Thr Leu Ala Val Glu Lys Glu Gly Cys Pro Val Cys Ile Thr Val
                85                  90                  95
Asn Thr Thr Ile Cys Ala Gly Tyr Cys Pro Thr Met Thr Arg Val Leu
                100                 105                 110
Gln Gly Val Leu Pro Ala Leu Pro Gln Val Val Cys Asn Tyr Arg Asp
        115                 120                 125
Val Arg Phe Glu Ser Ile Arg Leu Pro Gly Cys Pro Arg Gly Val Asn
        130                 135                 140
Pro Val Val Ser Tyr Ala Val Ala Leu Ser Cys Gln Cys Ala Leu Cys
145                 150                 155                 160
Asn Thr Asp Tyr Ser Asp Cys Ile His Glu Ala Ile Lys Thr Asn Tyr
                165                 170                 175
Cys Thr Lys Pro Gln Lys Ser Tyr Ser Ser Ser Lys Ala Pro Pro
                180                 185                 190
Pro Ser Leu Pro Ser Pro Ser Arg Leu Pro Gly Pro Ser Asp Thr Pro
        195                 200                 205
```

Ile Leu Pro Gln
    210

(2) INFORMATION FOR SEQ ID NO:71:

(i) SEQUENCE CHARACTERISTICS:
        (A) LENGTH: 226 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:71:

Met Glu Met Phe Gln Gly Leu Leu Leu Leu Leu Ser Met Gly
1               5                   10                  15

Gly Thr Trp Ala Xaa Xaa Xaa Ala Asp Ala Ala Pro Thr Val Ser Ile
                20                  25                  30

Phe Pro Ser Ser Glu Gln Leu Thr Ser Gly Gly Ala Ser Val Val
            35                  40                  45

Cys Phe Leu Asn Asn Phe Tyr Pro Lys Asp Ile Asn Val Lys Trp Lys
50                      55                  60

Ile Asp Gly Ser Glu Arg Gln Asn Gly Val Leu Asn Ser Trp Thr Asp
65                  70                  75                  80

Gln Asp Ser Lys Asp Ser Thr Tyr Ser Met Ser Ser Thr Leu Thr Trp
                85                  90                  95

Thr Lys Asp Glu Tyr Glu Arg His Asn Ser Tyr Thr Cys Glu Ala Thr
                100                 105                 110

His Lys Thr Ser Thr Ser Pro Ile Val Lys Ser Phe Asn Arg Asn Glu
                115                 120                 125

Cys Gly Lys Ser Lys Arg Ala Pro Asp Val Gln Asp Cys Pro Glu Cys
130                 135                 140

Thr Leu Gln Glu Asn Pro Phe Phe Ser Gln Pro Gly Ala Pro Ile Leu
145                 150                 155                 160

Gln Cys Met Gly Cys Cys Phe Ser Arg Ala Tyr Pro Thr Pro Leu Arg
                165                 170                 175

Ser Lys Lys Thr Met Leu Val Gln Lys Asn Val Thr Ser Glu Ser Thr
                180                 185                 190

Cys Cys Val Ala Lys Ser Tyr Asn Arg Val Thr Val Met Gly Gly Phe
                195                 200                 205

Lys Val Glu Asn His Thr Ala Cys His Cys Ser Thr Cys Tyr Tyr His
    210                 215                 220

Lys Ser
225

(2) INFORMATION FOR SEQ ID NO:72:

(i) SEQUENCE CHARACTERISTICS:
        (A) LENGTH: 276 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:72:

```
Met Glu Met Phe Gln Gly Leu Leu Leu Leu Leu Leu Ser Met Gly
  1               5                  10                  15

Gly Thr Trp Ala Xaa Xaa Xaa Ser Ala Lys Thr Thr Pro Pro Ser Val
               20                  25                  30

Tyr Pro Leu Ala Pro Gly Ser Ala Ala Gln Thr Asn Ser Met Val Thr
           35                  40                  45

Leu Gly Cys Leu Val Lys Gly Tyr Phe Pro Glu Pro Val Thr Val Thr
       50                  55                  60

Trp Asn Ser Gly Ser Leu Ser Ser Gly Val His Thr Phe Pro Ala Val
 65                  70                  75                  80

Leu Glu Ser Asp Leu Tyr Thr Leu Ser Ser Val Thr Val Pro Ser
               85                  90                  95

Ser Pro Arg Pro Ser Glu Thr Val Thr Cys Asn Val Ala His Pro Ala
           100                 105                 110

Ser Ser Thr Lys Val Asp Lys Lys Ile Val Pro Arg Asp Cys Gly Lys
           115                 120                 125

Ser Lys Arg Ser Lys Glu Pro Leu Arg Pro Arg Cys Arg Pro Ile Asn
       130                 135                 140

Ala Thr Leu Ala Val Glu Lys Glu Gly Cys Pro Val Cys Ile Thr Val
145                 150                 155                 160

Asn Thr Thr Ile Cys Ala Gly Tyr Cys Pro Thr Met Thr Arg Val Leu
               165                 170                 175

Gln Gly Val Leu Pro Ala Leu Pro Gln Val Val Cys Asn Tyr Arg Asp
           180                 185                 190

Val Arg Phe Glu Ser Ile Arg Leu Pro Gly Cys Pro Arg Gly Val Asn
       195                 200                 205

Pro Val Val Ser Tyr Ala Val Ala Leu Ser Cys Gln Cys Ala Leu Cys
   210                 215                 220

Arg Arg Ser Thr Thr Asp Cys Gly Gly Pro Lys Asp His Pro Leu Thr
225                 230                 235                 240

Cys Asp Asp Pro Arg Phe Gln Asp Ser Ser Ser Lys Ala Pro Pro
               245                 250                 255

Pro Ser Leu Pro Ser Pro Ser Arg Leu Pro Gly Pro Ser Asp Thr Pro
           260                 265                 270

Ile Leu Pro Gln
       275
```

(2) INFORMATION FOR SEQ ID NO:73:

(i) SEQUENCE CHARACTERISTICS:
        (A) LENGTH: 245 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:73:

```
Met Glu Met Phe Gln Gly Leu Leu Leu Leu Leu Leu Ser Met Gly
  1               5                  10                  15

Gly Thr Trp Ala Xaa Xaa Xaa Ser Ala Lys Thr Thr Pro Pro Ser Val
               20                  25                  30
```

```
Tyr Pro Leu Ala Pro Gly Ser Ala Ala Gln Thr Asn Ser Met Val Thr
            35                  40                  45

Leu Gly Cys Leu Val Lys Gly Tyr Phe Pro Glu Pro Val Thr Val Thr
     50                  55                  60

Trp Asn Ser Gly Ser Leu Ser Ser Gly Val His Thr Phe Pro Ala Val
 65                  70                  75                  80

Leu Glu Ser Asp Leu Tyr Thr Leu Ser Ser Val Thr Val Pro Ser
                 85                  90                  95

Ser Pro Arg Pro Ser Glu Thr Val Thr Cys Asn Val Ala His Pro Ala
            100                 105                 110

Ser Ser Thr Lys Val Asp Lys Lys Ile Val Pro Arg Asp Cys Gly Lys
            115                 120                 125

Ser Lys Arg Ser Arg Glu Pro Leu Arg Pro Trp Cys His Pro Ile Asn
            130                 135                 140

Ala Ile Leu Ala Val Glu Lys Glu Gly Cys Pro Val Cys Ile Thr Val
145                 150                 155                 160

Asn Thr Thr Ile Cys Ala Gly Tyr Cys Pro Thr Met Met Arg Val Leu
                 165                 170                 175

Gln Ala Val Leu Pro Pro Leu Pro Gln Val Val Cys Thr Tyr Arg Asp
            180                 185                 190

Val Arg Phe Glu Ser Ile Arg Leu Pro Gly Cys Pro Arg Gly Val Asp
            195                 200                 205

Pro Val Val Ser Phe Pro Val Ala Leu Ser Cys Arg Cys Ala Leu Cys
            210                 215                 220

Arg Arg Ser Thr Ser Asp Cys Gly Gly Pro Lys Asp His Pro Leu Thr
225                 230                 235                 240

Cys Asp His Pro Gln
                245

(2) INFORMATION FOR SEQ ID NO:74:

(i) SEQUENCE CHARACTERISTICS:
        (A) LENGTH: 242 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:74:

Met Glu Met Phe Gln Gly Leu Leu Leu Leu Leu Leu Ser Met Gly
 1               5                  10                  15

Gly Thr Trp Ala Xaa Xaa Xaa Ser Ala Lys Thr Thr Pro Pro Ser Val
            20                  25                  30

Tyr Pro Leu Ala Pro Gly Ser Ala Ala Gln Thr Asn Ser Met Val Thr
            35                  40                  45

Leu Gly Cys Leu Val Lys Gly Tyr Phe Pro Glu Pro Val Thr Val Thr
     50                  55                  60

Trp Asn Ser Gly Ser Leu Ser Ser Gly Val His Thr Phe Pro Ala Val
 65                  70                  75                  80

Leu Glu Ser Asp Leu Tyr Thr Leu Ser Ser Val Thr Val Pro Ser
                 85                  90                  95

Ser Pro Arg Pro Ser Glu Thr Val Thr Cys Asn Val Ala His Pro Ala
```

-continued

```
                100             105             110
Ser Ser Thr Lys Val Asp Lys Lys Ile Val Pro Arg Asp Cys Gly Lys
        115             120             125

Ser Lys Arg Asn Ser Cys Glu Leu Thr Asn Ile Thr Ile Ala Ile Glu
130             135             140

Lys Glu Glu Cys Arg Phe Cys Ile Ser Ile Asn Thr Thr Trp Cys Ala
145             150             155             160

Gly Tyr Cys Tyr Thr Arg Asp Leu Val Tyr Lys Asp Pro Ala Arg Pro
            165             170             175

Lys Ile Gln Lys Thr Cys Thr Phe Lys Glu Leu Val Tyr Glu Thr Val
            180             185             190

Arg Val Pro Gly Cys Ala His His Ala Asp Ser Leu Tyr Thr Tyr Pro
            195             200             205

Val Ala Thr Gln Cys His Cys Gly Lys Cys Asp Ser Asp Ser Thr Asp
        210             215             220

Cys Thr Val Arg Gly Leu Gly Pro Ser Tyr Cys Ser Phe Gly Glu Met
225             230             235             240

Lys Glu
```

(2) INFORMATION FOR SEQ ID NO:75:

(i) SEQUENCE CHARACTERISTICS:
        (A) LENGTH: 243 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:75:

```
Met Glu Met Phe Gln Gly Leu Leu Leu Leu Leu Leu Ser Met Gly
1               5               10              15

Gly Thr Trp Ala Xaa Xaa Xaa Ser Ala Lys Thr Thr Pro Pro Ser Val
            20              25              30

Tyr Pro Leu Ala Pro Gly Ser Ala Ala Gln Thr Asn Ser Met Val Thr
            35              40              45

Leu Gly Cys Leu Val Lys Gly Tyr Phe Pro Glu Pro Val Thr Val Thr
        50              55              60

Trp Asn Ser Gly Ser Leu Ser Ser Gly Val His Thr Phe Pro Ala Val
65              70              75              80

Leu Glu Ser Asp Leu Tyr Thr Leu Ser Ser Val Thr Val Pro Ser
            85              90              95

Ser Pro Arg Pro Ser Glu Thr Val Thr Cys Asn Val Ala His Pro Ala
            100             105             110

Ser Ser Thr Lys Val Asp Lys Lys Ile Val Pro Arg Asp Cys Gly Lys
            115             120             125

Ser Lys Arg Phe Cys Ile Pro Thr Glu Tyr Thr Met His Ile Glu Arg
            130             135             140

Arg Glu Cys Ala Tyr Cys Leu Thr Ile Asn Thr Thr Ile Cys Ala Gly
145             150             155             160

Tyr Cys Met Thr Arg Asp Ile Asn Gly Lys Leu Phe Leu Pro Lys Tyr
            165             170             175

Ala Leu Ser Gln Asp Val Cys Thr Tyr Arg Asp Phe Ile Tyr Arg Thr
```

```
Val Glu Ile Pro Gly Cys Pro Leu His Val Ala Pro Tyr Phe Ser Tyr
            195                 200                 205

Pro Val Ala Leu Ser Cys Lys Cys Gly Lys Cys Asn Thr Asp Tyr Ser
        210                 215                 220

Asp Cys Ile His Glu Ala Ile Lys Thr Asn Tyr Cys Thr Lys Pro Gln
225                 230                 235                 240

Lys Ser Tyr
```

(2) INFORMATION FOR SEQ ID NO:76:

(i) SEQUENCE CHARACTERISTICS:
        (A) LENGTH: 276 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:76:

```
Met Glu Met Phe Gln Gly Leu Leu Leu Leu Leu Leu Ser Met Gly
1               5                   10                  15

Gly Thr Trp Ala Xaa Xaa Xaa Ser Ala Lys Thr Thr Pro Pro Ser Val
            20                  25                  30

Tyr Pro Leu Ala Pro Gly Ser Ala Ala Gln Thr Asn Ser Met Val Thr
            35                  40                  45

Leu Gly Cys Leu Val Lys Gly Tyr Phe Pro Glu Pro Val Thr Val Thr
        50                  55                  60

Trp Asn Ser Gly Ser Leu Ser Ser Gly Val His Thr Phe Pro Ala Val
65                  70                  75                  80

Leu Glu Ser Asp Leu Tyr Thr Leu Ser Ser Val Thr Val Pro Ser
            85                  90                  95

Ser Pro Arg Pro Ser Glu Thr Val Thr Cys Asn Val Ala His Pro Ala
            100                 105                 110

Ser Ser Thr Lys Val Asp Lys Lys Ile Val Pro Arg Asp Cys Gly Lys
        115                 120                 125

Ser Lys Arg Ser Lys Glu Pro Leu Arg Pro Arg Cys Arg Pro Ile Asn
130                 135                 140

Ala Thr Leu Ala Val Glu Lys Glu Gly Cys Pro Val Cys Ile Thr Val
145                 150                 155                 160

Asn Thr Thr Ile Cys Ala Gly Tyr Cys Pro Thr Met Thr Arg Val Leu
                165                 170                 175

Gln Gly Val Leu Pro Ala Leu Pro Gln Val Val Cys Asn Tyr Arg Asp
            180                 185                 190

Val Arg Phe Glu Ser Ile Arg Leu Pro Gly Cys Pro Arg Gly Val Asn
        195                 200                 205

Pro Val Val Ser Tyr Ala Val Ala Leu Ser Cys Gln Cys Ala Leu Cys
    210                 215                 220

Asp Ser Asp Ser Thr Asp Cys Thr Val Arg Gly Leu Gly Pro Ser Tyr
225                 230                 235                 240

Cys Ser Phe Gly Glu Met Lys Glu Ser Ser Ser Lys Ala Pro Pro
                245                 250                 255

Pro Ser Leu Pro Ser Pro Ser Arg Leu Pro Gly Pro Ser Asp Thr Pro
```

Ile Leu Pro Gln
         275

(2) INFORMATION FOR SEQ ID NO:77:

(i) SEQUENCE CHARACTERISTICS:
       (A) LENGTH: 276 amino acids
       (B) TYPE: amino acid
       (C) STRANDEDNESS: unknown
       (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:77:

Met Glu Met Phe Gln Gly Leu Leu Leu Leu Leu Leu Ser Met Gly
1               5                   10                  15

Gly Thr Trp Ala Xaa Xaa Xaa Ser Ala Lys Thr Thr Pro Pro Ser Val
                20              25                  30

Tyr Pro Leu Ala Pro Gly Ser Ala Ala Gln Thr Asn Ser Met Val Thr
            35                  40                  45

Leu Gly Cys Leu Val Lys Gly Tyr Phe Pro Glu Pro Val Thr Val Thr
50                  55                  60

Trp Asn Ser Gly Ser Leu Ser Ser Gly Val His Thr Phe Pro Ala Val
65                  70                  75                  80

Leu Glu Ser Asp Leu Tyr Thr Leu Ser Ser Ser Val Thr Val Pro Ser
                85                  90                  95

Ser Pro Arg Pro Ser Glu Thr Val Thr Cys Asn Val Ala His Pro Ala
            100                 105                 110

Ser Ser Thr Lys Val Asp Lys Lys Ile Val Pro Arg Asp Cys Gly Lys
        115                 120                 125

Ser Lys Arg Ser Lys Glu Pro Leu Arg Pro Arg Cys Arg Pro Ile Asn
130                 135                 140

Ala Thr Leu Ala Val Glu Lys Glu Gly Cys Pro Val Cys Ile Thr Val
145                 150                 155                 160

Asn Thr Thr Ile Cys Ala Gly Tyr Cys Pro Thr Met Thr Arg Val Leu
                165                 170                 175

Gln Gly Val Leu Pro Ala Leu Pro Gln Val Val Cys Asn Tyr Arg Asp
            180                 185                 190

Val Arg Phe Glu Ser Ile Arg Leu Pro Gly Cys Pro Arg Gly Val Asn
        195                 200                 205

Pro Val Val Ser Tyr Ala Val Ala Leu Ser Cys Gln Cys Ala Leu Cys
210                 215                 220

Asn Thr Asp Tyr Ser Asp Cys Ile His Glu Ala Ile Lys Thr Asn Tyr
225                 230                 235                 240

Cys Thr Lys Pro Gln Lys Ser Tyr Ser Ser Ser Lys Ala Pro Pro
                245                 250                 255

Pro Ser Leu Pro Ser Pro Ser Arg Leu Pro Gly Pro Ser Asp Thr Pro
            260                 265                 270

Ile Leu Pro Gln
         275

(2) INFORMATION FOR SEQ ID NO:78:

(i) SEQUENCE CHARACTERISTICS:
        (A) LENGTH: 226 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:78:

```
Met Glu Met Phe Gln Gly Leu Leu Leu Leu Leu Leu Ser Met Gly
 1               5                  10                  15

Gly Thr Trp Ala Xaa Xaa Xaa Ala Asp Ala Ala Pro Thr Val Ser Ile
            20                  25                  30

Phe Pro Pro Ser Ser Glu Gln Leu Thr Ser Gly Gly Ala Ser Val Val
            35                  40                  45

Cys Phe Leu Asn Asn Phe Tyr Pro Lys Asp Ile Asn Val Lys Trp Lys
50                  55                  60

Ile Asp Gly Ser Glu Arg Gln Asn Gly Val Leu Asn Ser Trp Thr Asp
65                  70                  75                  80

Gln Asp Ser Lys Asp Ser Thr Tyr Ser Met Ser Ser Thr Leu Thr Trp
                85                  90                  95

Thr Lys Asp Glu Tyr Glu Arg His Asn Ser Tyr Thr Cys Glu Ala Thr
                100                 105                 110

His Lys Thr Ser Thr Ser Pro Ile Val Lys Ser Phe Asn Arg Asn Glu
                115                 120                 125

Ala Gly Lys Ser Lys Arg Ala Pro Asp Val Gln Asp Cys Pro Glu Cys
130                 135                 140

Thr Leu Gln Glu Asn Pro Phe Phe Ser Gln Pro Gly Ala Pro Ile Leu
145                 150                 155                 160

Gln Cys Met Gly Cys Cys Phe Ser Arg Ala Tyr Pro Thr Pro Leu Arg
                165                 170                 175

Ser Lys Lys Thr Met Leu Val Gln Lys Asn Val Thr Ser Glu Ser Thr
                180                 185                 190

Cys Cys Val Ala Lys Ser Tyr Asn Arg Val Thr Val Met Gly Gly Phe
                195                 200                 205

Lys Val Glu Asn His Thr Ala Cys His Cys Ser Thr Cys Tyr Tyr His
    210                 215                 220

Lys Ser
225
```

(2) INFORMATION FOR SEQ ID NO:79:

(i) SEQUENCE CHARACTERISTICS:
        (A) LENGTH: 276 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:79:

```
Met Glu Met Phe Gln Gly Leu Leu Leu Leu Leu Leu Ser Met Gly
 1               5                  10                  15
```

```
Gly Thr Trp Ala Xaa Xaa Xaa Ser Ala Lys Thr Thr Pro Pro Ser Val
             20                  25                  30

Tyr Pro Leu Ala Pro Gly Ser Ala Ala Gln Thr Asn Ser Met Val Thr
             35                  40                  45

Leu Gly Cys Leu Val Lys Gly Tyr Phe Pro Glu Pro Val Thr Val Thr
 50                  55                  60

Trp Asn Ser Gly Ser Leu Ser Ser Gly Val His Thr Phe Pro Ala Val
 65                  70                  75                  80

Leu Glu Ser Asp Leu Tyr Thr Leu Ser Ser Val Thr Val Pro Ser
                 85                  90                  95

Ser Pro Arg Pro Ser Glu Thr Val Thr Cys Asn Val Ala His Pro Ala
                100                 105                 110

Ser Ser Thr Lys Val Asp Lys Lys Ile Val Pro Arg Asp Ala Gly Lys
                115                 120                 125

Ser Lys Arg Ser Lys Glu Pro Leu Arg Pro Arg Cys Arg Pro Ile Asn
                130                 135                 140

Ala Thr Leu Ala Val Glu Lys Glu Gly Cys Pro Val Cys Ile Thr Val
145                 150                 155                 160

Asn Thr Thr Ile Cys Ala Gly Tyr Cys Pro Thr Met Thr Arg Val Leu
                165                 170                 175

Gln Gly Val Leu Pro Ala Leu Pro Gln Val Val Cys Asn Tyr Arg Asp
                180                 185                 190

Val Arg Phe Glu Ser Ile Arg Leu Pro Gly Cys Pro Arg Gly Val Asn
                195                 200                 205

Pro Val Val Ser Tyr Ala Val Ala Leu Ser Cys Gln Cys Ala Leu Cys
                210                 215                 220

Arg Arg Ser Thr Thr Asp Cys Gly Gly Pro Lys Asp His Pro Leu Thr
225                 230                 235                 240

Cys Asp Asp Pro Arg Phe Gln Asp Ser Ser Ser Lys Ala Pro Pro
                    245                 250                 255

Pro Ser Leu Pro Ser Pro Ser Arg Leu Pro Gly Pro Ser Asp Thr Pro
                260                 265                 270

Ile Leu Pro Gln
        275

(2) INFORMATION FOR SEQ ID NO:80:

(i) SEQUENCE CHARACTERISTICS:
        (A) LENGTH: 245 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:80:

Met Glu Met Phe Gln Gly Leu Leu Leu Leu Leu Leu Leu Ser Met Gly
 1               5                  10                  15

Gly Thr Trp Ala Xaa Xaa Xaa Ser Ala Lys Thr Thr Pro Pro Ser Val
             20                  25                  30

Tyr Pro Leu Ala Pro Gly Ser Ala Ala Gln Thr Asn Ser Met Val Thr
             35                  40                  45

Leu Gly Cys Leu Val Lys Gly Tyr Phe Pro Glu Pro Val Thr Val Thr
 50                  55                  60
```

```
Trp Asn Ser Gly Ser Leu Ser Ser Gly Val His Thr Phe Pro Ala Val
 65                  70                  75                  80

Leu Glu Ser Asp Leu Tyr Thr Leu Ser Ser Val Thr Val Pro Ser
                 85                  90                  95

Ser Pro Arg Pro Ser Glu Thr Val Thr Cys Asn Val Ala His Pro Ala
                100                 105                 110

Ser Ser Thr Lys Val Asp Lys Lys Ile Val Pro Arg Asp Ala Gly Lys
                115                 120                 125

Ser Lys Arg Ser Arg Glu Pro Leu Arg Pro Trp Cys His Pro Ile Asn
            130                 135                 140

Ala Ile Leu Ala Val Glu Lys Glu Gly Cys Pro Val Cys Ile Thr Val
145                 150                 155                 160

Asn Thr Thr Ile Cys Ala Gly Tyr Cys Pro Thr Met Met Arg Val Leu
                165                 170                 175

Gln Ala Val Leu Pro Pro Leu Pro Gln Val Val Cys Thr Tyr Arg Asp
                180                 185                 190

Val Arg Phe Glu Ser Ile Arg Leu Pro Gly Cys Pro Arg Gly Val Asp
                195                 200                 205

Pro Val Val Ser Phe Pro Val Ala Leu Ser Cys Arg Cys Ala Leu Cys
                210                 215                 220

Arg Arg Ser Thr Ser Asp Cys Gly Gly Pro Lys Asp His Pro Leu Thr
225                 230                 235                 240

Cys Asp His Pro Gln
                245

(2) INFORMATION FOR SEQ ID NO:81:

(i) SEQUENCE CHARACTERISTICS:
        (A) LENGTH: 242 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:81:

Met Glu Met Phe Gln Gly Leu Leu Leu Leu Leu Leu Ser Met Gly
 1               5                  10                  15

Gly Thr Trp Ala Xaa Xaa Xaa Ser Ala Lys Thr Thr Pro Pro Ser Val
                 20                  25                  30

Tyr Pro Leu Ala Pro Gly Ser Ala Ala Gln Thr Asn Ser Met Val Thr
                 35                  40                  45

Leu Gly Cys Leu Val Lys Gly Tyr Phe Pro Glu Pro Val Thr Val Thr
             50                  55                  60

Trp Asn Ser Gly Ser Leu Ser Ser Gly Val His Thr Phe Pro Ala Val
 65                  70                  75                  80

Leu Glu Ser Asp Leu Tyr Thr Leu Ser Ser Val Thr Val Pro Ser
                 85                  90                  95

Ser Pro Arg Pro Ser Glu Thr Val Thr Cys Asn Val Ala His Pro Ala
                100                 105                 110

Ser Ser Thr Lys Val Asp Lys Lys Ile Val Pro Arg Asp Ala Gly Lys
                115                 120                 125

Ser Lys Arg Asn Ser Cys Glu Leu Thr Asn Ile Thr Ile Ala Ile Glu
```

```
            130                 135                 140
Lys Glu Glu Cys Arg Phe Cys Ile Ser Ile Asn Thr Thr Trp Cys Ala
145                 150                 155                 160

Gly Tyr Cys Tyr Thr Arg Asp Leu Val Tyr Lys Asp Pro Ala Arg Pro
                165                 170                 175

Lys Ile Gln Lys Thr Cys Thr Phe Lys Glu Leu Val Tyr Glu Thr Val
                180                 185                 190

Arg Val Pro Gly Cys Ala His His Ala Asp Ser Leu Tyr Thr Tyr Pro
                195                 200                 205

Val Ala Thr Gln Cys His Cys Gly Lys Cys Asp Ser Asp Ser Thr Asp
                210                 215                 220

Cys Thr Val Arg Gly Leu Gly Pro Ser Tyr Cys Ser Phe Gly Glu Met
225                 230                 235                 240

Lys Glu (2) INFORMATION FOR SEQ ID NO:82:

(i) SEQUENCE CHARACTERISTICS:
        (A) LENGTH: 243 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:82:

Met Glu Met Phe Gln Gly Leu Leu Leu Leu Leu Leu Ser Met Gly
1               5                   10                  15

Gly Thr Trp Ala Xaa Xaa Xaa Ser Ala Lys Thr Thr Pro Pro Ser Val
                20                  25                  30

Tyr Pro Leu Ala Pro Gly Ser Ala Ala Gln Thr Asn Ser Met Val Thr
                35                  40                  45

Leu Gly Cys Leu Val Lys Gly Tyr Phe Pro Glu Pro Val Thr Val Thr
50                  55                  60

Trp Asn Ser Gly Ser Leu Ser Ser Gly Val His Thr Phe Pro Ala Val
65                  70                  75                  80

Leu Glu Ser Asp Leu Tyr Thr Leu Ser Ser Ser Val Thr Val Pro Ser
                85                  90                  95

Ser Pro Arg Pro Ser Glu Thr Val Thr Cys Asn Val Ala His Pro Ala
                100                 105                 110

Ser Ser Thr Lys Val Asp Lys Lys Ile Val Pro Arg Asp Ala Gly Lys
                115                 120                 125

Ser Lys Arg Phe Cys Ile Pro Thr Glu Tyr Thr Met His Ile Glu Arg
                130                 135                 140

Arg Glu Cys Ala Tyr Cys Leu Thr Ile Asn Thr Thr Ile Cys Ala Gly
145                 150                 155                 160

Tyr Cys Met Thr Arg Asp Ile Asn Gly Lys Leu Phe Leu Pro Lys Tyr
                165                 170                 175

Ala Leu Ser Gln Asp Val Cys Thr Tyr Arg Asp Phe Ile Tyr Arg Thr
                180                 185                 190

Val Glu Ile Pro Gly Cys Pro Leu His Val Ala Pro Tyr Phe Ser Tyr
                195                 200                 205

Pro Val Ala Leu Ser Cys Lys Cys Gly Lys Cys Asn Thr Asp Tyr Ser
```

```
            210                 215                 220
Asp Cys Ile His Glu Ala Ile Lys Thr Asn Tyr Cys Thr Lys Pro Gln
225                 230                 235                 240

Lys Ser Tyr
```

(2) INFORMATION FOR SEQ ID NO:83:

(i) SEQUENCE CHARACTERISTICS:
        (A) LENGTH: 276 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:83:

```
Met Glu Met Phe Gln Gly Leu Leu Leu Leu Leu Leu Ser Met Gly
1               5                   10                  15

Gly Thr Trp Ala Xaa Xaa Xaa Ser Ala Lys Thr Thr Pro Pro Ser Val
                20                  25                  30

Tyr Pro Leu Ala Pro Gly Ser Ala Ala Gln Thr Asn Ser Met Val Thr
                35                  40                  45

Leu Gly Cys Leu Val Lys Gly Tyr Phe Pro Glu Pro Val Thr Val Thr
            50                  55                  60

Trp Asn Ser Gly Ser Leu Ser Ser Gly Val His Thr Phe Pro Ala Val
65                  70                  75                  80

Leu Glu Ser Asp Leu Tyr Thr Leu Ser Ser Val Thr Val Pro Ser
                85                  90                  95

Ser Pro Arg Pro Ser Glu Thr Val Thr Cys Asn Val Ala His Pro Ala
                100                 105                 110

Ser Ser Thr Lys Val Asp Lys Lys Ile Val Pro Arg Asp Ala Gly Lys
            115                 120                 125

Ser Lys Arg Ser Lys Glu Pro Leu Arg Pro Arg Cys Arg Pro Ile Asn
            130                 135                 140

Ala Thr Leu Ala Val Glu Lys Glu Gly Cys Pro Val Cys Ile Thr Val
145                 150                 155                 160

Asn Thr Thr Ile Cys Ala Gly Tyr Cys Pro Thr Met Thr Arg Val Leu
                165                 170                 175

Gln Gly Val Leu Pro Ala Leu Pro Gln Val Val Cys Asn Tyr Arg Asp
            180                 185                 190

Val Arg Phe Glu Ser Ile Arg Leu Pro Gly Cys Pro Arg Gly Val Asn
            195                 200                 205

Pro Val Val Ser Tyr Ala Val Ala Leu Ser Cys Gln Cys Ala Leu Cys
            210                 215                 220

Asp Ser Asp Ser Thr Asp Cys Thr Val Arg Gly Leu Gly Pro Ser Tyr
225                 230                 235                 240

Cys Ser Phe Gly Glu Met Lys Glu Ser Ser Ser Lys Ala Pro Pro
                245                 250                 255

Pro Ser Leu Pro Ser Pro Ser Arg Leu Pro Gly Pro Ser Asp Thr Pro
            260                 265                 270

Ile Leu Pro Gln
            275
```

(2) INFORMATION FOR SEQ ID NO:84:

(i) SEQUENCE CHARACTERISTICS:
        (A) LENGTH: 276 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:84:

```
Met Glu Met Phe Gln Gly Leu Leu Leu Leu Leu Leu Ser Met Gly
 1               5                  10                  15

Gly Thr Trp Ala Xaa Xaa Xaa Ser Ala Lys Thr Thr Pro Ser Val
                 20                  25                  30

Tyr Pro Leu Ala Pro Gly Ser Ala Ala Gln Thr Asn Ser Met Val Thr
             35                  40                  45

Leu Gly Cys Leu Val Lys Gly Tyr Phe Pro Glu Pro Val Thr Val Thr
     50                  55                      60

Trp Asn Ser Gly Ser Leu Ser Ser Gly Val His Thr Phe Pro Ala Val
 65                  70                  75                  80

Leu Glu Ser Asp Leu Tyr Thr Leu Ser Ser Val Thr Val Pro Ser
                 85                  90                  95

Ser Pro Arg Pro Ser Glu Thr Val Thr Cys Asn Val Ala His Pro Ala
                100                 105                 110

Ser Ser Thr Lys Val Asp Lys Lys Ile Val Pro Arg Asp Ala Gly Lys
            115                 120                 125

Ser Lys Arg Ser Lys Glu Pro Leu Arg Pro Arg Cys Arg Pro Ile Asn
130                 135                 140

Ala Thr Leu Ala Val Glu Lys Glu Gly Cys Pro Val Cys Ile Thr Val
145                 150                 155                 160

Asn Thr Thr Ile Cys Ala Gly Tyr Cys Pro Thr Met Thr Arg Val Leu
                165                 170                 175

Gln Gly Val Leu Pro Ala Leu Pro Gln Val Val Cys Asn Tyr Arg Asp
            180                 185                 190

Val Arg Phe Glu Ser Ile Arg Leu Pro Gly Cys Pro Arg Gly Val Asn
        195                 200                 205

Pro Val Val Ser Tyr Ala Val Ala Leu Ser Cys Gln Cys Ala Leu Cys
    210                 215                 220

Asn Thr Asp Tyr Ser Asp Cys Ile His Glu Ala Ile Lys Thr Asn Tyr
225                 230                 235                 240

Cys Thr Lys Pro Gln Lys Ser Tyr Ser Ser Ser Lys Ala Pro Pro
                245                 250                 255

Pro Ser Leu Pro Ser Pro Ser Arg Leu Pro Gly Pro Ser Asp Thr Pro
                260                 265                 270

Ile Leu Pro Gln
            275
```

(2) INFORMATION FOR SEQ ID NO:85:

(i) SEQUENCE CHARACTERISTICS:
        (A) LENGTH: 203 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:85:

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
50                      55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
            115                 120                 125

Thr Cys Asp Asp Pro Arg Phe Gln Asp Ser Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln Arg Ile Ala Arg Leu Glu Glu Lys Val Lys Thr
                165                 170                 175

Leu Lys Ala Gln Asn Ser Glu Leu Ala Ser Thr Ala Asn Met Leu Arg
            180                 185                 190

Glu Gln Val Ala Gln Leu Lys Gln Lys Val Met
            195                 200

(2) INFORMATION FOR SEQ ID NO:86:

(i) SEQUENCE CHARACTERISTICS:
        (A) LENGTH: 209 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:86:

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
50                      55                  60

Leu Gln Gly Val Leu Pro Ala Leu Pro Gln Val Val Cys Asn Tyr Arg
65                  70                  75                  80

```
Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Ser Thr Thr Asp Cys Gly Gly Pro Lys Asp His Pro Leu
        115                 120                 125

Thr Cys Asp Asp Pro Arg Phe Gln Asp Ser Ser Ser Lys Ala Pro
    130                 135                 140

Pro Ser Leu Pro Ser Pro Ser Arg Leu Pro Gly Pro Ser Asp Thr
145             150                 155                 160

Pro Ile Leu Pro Gln Gly Ser Gly Ser Gly Ser Arg Ile Ala Arg Leu
                165                 170                 175

Glu Glu Lys Val Lys Thr Leu Lys Ala Gln Asn Ser Glu Leu Ala Ser
            180                 185                 190

Thr Ala Asn Met Leu Arg Glu Gln Val Ala Gln Leu Lys Gln Lys Val
            195                 200                 205

Met
```

(2) INFORMATION FOR SEQ ID NO:87:

(i) SEQUENCE CHARACTERISTICS:
        (A) LENGTH: 209 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:87:

```
Met Glu Met Phe Gln Gly Leu Leu Leu Leu Leu Leu Ser Met Gly
 1               5                  10                  15

Gly Thr Trp Ala Ser Arg Glu Pro Leu Arg Pro Trp Cys His Pro Ile
                20                  25                  30

Asn Ala Ile Leu Ala Val Glu Lys Glu Gly Cys Pro Val Cys Ile Thr
            35                  40                  45

Val Asn Thr Thr Ile Cys Ala Gly Tyr Cys Pro Thr Met Met Arg Val
50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Ala Leu
            100                 105                 110

Cys Arg Arg Ser Thr Ser Asp Cys Gly Gly Pro Lys Asp His Pro Leu
        115                 120                 125

Thr Cys Asp Asp Pro Arg Phe Gln Asp Ser Ser Ser Lys Ala Pro
    130                 135                 140

Pro Pro Ser Leu Pro Ser Pro Ser Arg Leu Pro Gly Pro Ser Asp Thr
145             150                 155                 160

Pro Ile Leu Pro Gln Gly Ser Gly Ser Gly Ser Arg Ile Ala Arg Leu
                165                 170                 175

Glu Glu Lys Val Lys Thr Leu Lys Ala Gln Asn Ser Glu Leu Ala Ser
            180                 185                 190
```

```
Thr Ala Asn Met Leu Arg Glu Gln Val Ala Gln Leu Lys Gln Lys Val
            195                 200                 205

Met
```

(2) INFORMATION FOR SEQ ID NO:88:

(i) SEQUENCE CHARACTERISTICS:
        (A) LENGTH: 203 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:88:

```
Met Glu Met Phe Gln Gly Leu Leu Leu Leu Leu Leu Ser Met Gly
1               5                   10                  15

Gly Thr Trp Ala Asn Ser Cys Glu Leu Thr Asn Ile Thr Ile Ala Ile
            20                  25                  30

Glu Lys Glu Glu Cys Arg Phe Cys Ile Ser Ile Asn Thr Thr Trp Cys
            35                  40                  45

Ala Gly Tyr Cys Tyr Thr Arg Asp Leu Val Tyr Lys Asp Pro Ala Arg
50                  55                  60

Pro Lys Ile Gln Lys Thr Cys Thr Phe Lys Glu Leu Val Tyr Glu Thr
65                  70                  75                  80

Val Arg Val Pro Gly Cys Ala His His Ala Asp Ser Leu Tyr Thr Tyr
                85                  90                  95

Pro Val Ala Thr Gln Cys His Cys Gly Lys Cys Asp Ser Asp Ser Thr
                100                 105                 110

Asp Cys Thr Val Arg Gly Leu Gly Pro Ser Tyr Cys Ser Phe Gly Glu
            115                 120                 125

Met Lys Glu Ser Ser Ser Ser Lys Ala Pro Pro Ser Leu Pro Ser
            130                 135                 140

Pro Ser Arg Leu Pro Gly Pro Ser Asp Thr Pro Ile Leu Pro Gln Gly
145                 150                 155                 160

Ser Gly Ser Gly Ser Arg Ile Ala Arg Leu Glu Glu Lys Val Lys Thr
                165                 170                 175

Leu Lys Ala Gln Asn Ser Glu Leu Ala Ser Thr Ala Asn Met Leu Arg
            180                 185                 190

Glu Gln Val Ala Gln Leu Lys Gln Lys Val Met
            195                 200
```

(2) INFORMATION FOR SEQ ID NO:89:

(i) SEQUENCE CHARACTERISTICS:
        (A) LENGTH: 204 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:89:

```
Met Glu Met Phe Gln Gly Leu Leu Leu Leu Leu Leu Ser Met Gly
```

```
1               5                   10                  15
Gly Thr Trp Ala Phe Cys Ile Pro Thr Glu Tyr Thr Met His Ile Glu
                20                  25                  30
Arg Arg Glu Cys Ala Tyr Cys Leu Thr Ile Asn Thr Thr Ile Cys Ala
            35                  40                  45
Gly Tyr Cys Met Thr Arg Asp Ile Asn Gly Lys Leu Phe Leu Pro Lys
        50                  55                  60
Tyr Ala Leu Ser Gln Asp Val Cys Thr Tyr Arg Asp Phe Ile Tyr Arg
65                  70                  75                  80
Thr Val Glu Ile Pro Gly Cys Pro Leu His Val Ala Pro Tyr Phe Ser
                85                  90                  95
Tyr Pro Val Ala Leu Ser Cys Lys Cys Gly Lys Cys Asn Thr Asp Tyr
                100                 105                 110
Ser Asp Cys Ile His Glu Ala Ile Lys Thr Asn Tyr Cys Thr Lys Pro
            115                 120                 125
Gln Lys Ser Tyr Ser Ser Ser Lys Ala Pro Pro Pro Ser Leu Pro
        130                 135                 140
Ser Pro Ser Arg Leu Pro Gly Pro Ser Asp Thr Pro Ile Leu Pro Gln
145                 150                 155                 160
Gly Ser Gly Ser Gly Ser Arg Ile Ala Arg Leu Glu Glu Lys Val Lys
                165                 170                 175
Thr Leu Lys Ala Gln Asn Ser Glu Leu Ala Ser Thr Ala Asn Met Leu
            180                 185                 190
Arg Glu Gln Val Ala Gln Leu Lys Gln Lys Val Met
        195                 200
```

(2) INFORMATION FOR SEQ ID NO:90:

(i) SEQUENCE CHARACTERISTICS:
        (A) LENGTH: 206 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:90:

```
Met Glu Met Phe Gln Gly Leu Leu Leu Leu Leu Leu Ser Met Gly
1               5                   10                  15
Gly Thr Trp Ala Ser Lys Glu Pro Leu Arg Pro Arg Cys Arg Pro Ile
                20                  25                  30
Asn Ala Thr Leu Ala Val Glu Lys Glu Gly Cys Pro Val Cys Ile Thr
            35                  40                  45
Val Asn Thr Thr Ile Cys Ala Gly Tyr Cys Pro Thr Met Thr Arg Val
        50                  55                  60
Leu Gln Gly Val Leu Pro Ala Leu Pro Gln Val Val Cys Asn Tyr Arg
65                  70                  75                  80
Asp Val Arg Phe Glu Ser Ile Arg Leu Pro Gly Cys Pro Arg Gly Val
                85                  90                  95
Asn Pro Val Val Ser Tyr Ala Val Ala Leu Ser Cys Gln Cys Ala Leu
            100                 105                 110
Cys Arg Arg Ser Thr Thr Asp Cys Gly Gly Pro Lys Asp His Pro Leu
        115                 120                 125
```

-continued

```
Thr Cys Asp Asp Pro Arg Phe Gln Asp Ser Ser Ser Ser Lys Ala Pro
        130                 135                 140

Pro Pro Ser Leu Pro Ser Pro Ser Arg Leu Pro Gly Pro Ser Asp Thr
145                 150                 155                 160

Pro Ile Leu Pro Gln Cys Gly Gly Arg Ile Ala Arg Leu Glu Glu Lys
                165                 170                 175

Val Lys Thr Leu Lys Ala Gln Asn Ser Glu Leu Ala Ser Thr Ala Asn
            180                 185                 190

Met Leu Arg Glu Gln Val Ala Gln Leu Lys Gln Lys Val Met
        195                 200                 205
```

METHOD FOR MAKING HORMONE HETERODIMERS

GOVERNMENT LICENSING RIGHTS

The experiments in this application were supported by the National Institutes of Health, Grant Number HD14907. The United States Government has a paid-up license in this invention and the right in limited circumstances to require the patent owner to license others on reasonable terms as provided by the terms of Grant Number HD14907 awarded by the National Institutes of Health.

BACKGROUND OF THE INVENTION

1. Field of the Invention

The present invention relates to a method for preparing heterodimeric analogs of cysteine knot proteins. More specifically, the invention relates to a method for forming a subunit combination of a cysteine knot protein having an α-subunit and a β-subunit to prepare a heterodimeric protein analog which comprises the steps of (a) attaching a dimerization domain to the amino termini of both an α-subunit and a β-subunit of a cysteine knot protein; and (b) dimerizing the α-subunit and β-subunit to form a heterodimeric protein analog. In another embodiment, the invention relates to a method for forming a subunit combination of a cysteine knot protein having an α-subunit and a β-subunit to prepare a heterodimeric protein analog which comprises the steps of (a) attaching a dimerization domain to the amino terminus of an α-subunit and the carboxy terminus of a β-subunit of a cysteine knot protein; and (b) dimerizing the α-subunit and β-subunit to form a heterodimeric protein analog.

2. Description of the Background

The disclosures referred to herein to illustrate the background of the invention and to provide additional detail with respect to its practice are incorporated herein by reference and, for convenience, are numerically referenced in the following text and respectively grouped in the appended bibliography.

The Glycoprotein Hormones and Their Biological Actions

The glycoprotein hormone family (1–3) consists of three α, β heterodimeric glycoproteins found in the anterior pituitary gland where they are made and includes luteinizing hormone (LH), follicle stimulating hormone (FSH), and thyroid stimulating hormone (TSH). These hormones are found in most, if not all vertebrates. In some species, a glycoprotein hormone structurally similar to LH is found in the placenta wherein it is synthesized. The human placental hormone is known as human chorionic gonadotropin (hCG). In primates, significant quantities of all the hormones are also found as excretion products in urine. Urine from pregnant women serves as a convenient source of hCG. After menopause, when the secretion of LH and FSH from the anterior pituitary is greatly increased, significant quantities of LH and FSH are found in the urine and are termed human menopausal gonadotropins (hMG). Urine from menopausal women serves as an important source of LH and FSH activities. Urinary hormones (hCG, hMG, hFSH) and recombinant hormones have important clinical and commercial uses.

Gonadotropins such as CG, LH, and FSH play a major role in the reproductive process (4) while the structurally related hormone, TSH, is important for thyroid function. In women, FSH plays a crucial role in the development of follicles that can be ovulated, primarily through its influence on granulosa cells. LH synergizes with FSH and is normally essential for processes of ovulation, luteinization, and luteal function. Nonetheless, high LH levels can reduce fertility and are thought partly responsible for the loss of fertility associated with polycystic ovarian disease. hCG is important for maintenance of pregnancy and its early neutralization leads to infertility. In males LH is required for puberty and, in its absence, there is a failure to acquire the sexual attributes and fertility of an adult. The biological and clinical activities of these hormones are reviewed extensively in several textbooks including those by Yen and Jaffe (4), Adashi, Rock, and Rosenwaks (5), and DeGroot (6).

Both hCG and LH bind to luteinizing hormone receptors (LHR). In the testis, LHR are found primarily in the Leydig cells. In the ovary, LHR are found primarily in thecal cells, FSH-stimulated granulosa cells, and luteal cells. The major role of LH is to stimulate the formation of steroid hormones including the androgens testosterone and androstenedione (Leydig and thecal cells) and progesterone (FSH-stimulated granulosa, thecal, and luteal cells). LH also causes ovulation of mature follicles. While hCG is normally produced only by the placenta during pregnancy, due to its high affinity for LH receptors, the ease with which it can be purified from urine, and its long biological half-life, hCG has been widely used as a substitute for LH. Important clinical uses for hCG include stimulation of fertility in males and induction of ovulation in females.

FSH binds to FSH receptors (FSHR) located primarily in the Sertoli cells of the testis and the granulosa cells of the ovaries. The primary roles of FSH are to stimulate the conversion of androgens to estrogens, to promote the synthesis of inhibin and activin, to promote the development of Sertoli and granulosa cells, and to stimulate gamete maturation. The effect of FSH on granulosa cells leads to follicular maturation, a process during which the oocyte is prepared for ovulation and in which the granulosa cells acquire the ability to respond to LH. Follicle maturation is essential for the ability of LH to induce ovulation.

The differences in the effects of FSH and LH and the complex endocrine interactions between the two hormones cause them to have synergistic effects. For example, normal estrogen production is due to the effect of LH on androgen formation and the influence of FSH on the conversion of androgens to estradiol. Estrogens can inhibit the secretion of FSH and potentiate the secretion of LH. The ability of androgens to be converted to estrogens in non-ovarian tissues can disrupt this complex feedback interaction between steroidogenesis and the secretion of FSH and LH. For this reason, the ratio of LH/FSH activity as well as the absolute hormone levels in blood are important for reproductive functions such as ovulation of the proper number of oocytes during the menstrual and estrus cycles. Other hormones including activin and inhibin can exert an influence on this process, primarily through their influence on FSH secretion from the pituitary gland and their influence on the ovarian response to FSH.

TSH is produced in the anterior pituitary gland and its major function is to regulate the activity of the thyroid gland, causing it to synthesize and release thyroxin. Circulating levels of TSH and thyroxin are usually regulated by a negative feedback mechanism. Increases in TSH secretion usually lead to increased thyroxin synthesis and secretion by the thyroid. As thyroxin levels increase, the secretion of TSH is decreased. In this way there is a balance between the level of TSH and thyroid hormone. High levels of TSH can also stimulate the thyroid gland to remove iodine from circulation. Clinically, TSH can be used to promote the uptake of radioactive iodine and death of the thyroid cells. This form of thyroidectomy has been used to remove hyperactive thyroid tissues.

Uses of Glycoprotein Hormones and the Desirability of Novel Hormone Analogs

Hormones with FSH and LH activities are routinely used in the treatment of human infertility, a problem experienced by approximately 10–15% of all couples (7,8). A major cause of female infertility is polycystic ovarian disease or syndrome, a condition in which endogenous LH levels often appear to be elevated. In principle, infertility caused by inappropriately high LH activity could be suppressed by administration of an inhibitory hormone analog that competed with LH for binding to LHR. It has been known for many years (9,10) that it is possible to prepare analogs of hCG that act as LH antagonists by removing all or part of the oligosaccharides from the hormone. While it is possible to remove most of the oligosaccharides using endonucleases or exonucleases, in practice, it is not practical to remove all of them without denaturing the hormones. The remaining sugars can serve as substrates for enzymes and other factors that can hasten removal of the proteins from circulation (11–13). One potential means of avoiding this problem is to prepare analogs that have been genetically deglycosylated (i.e., by replacing or deleting amino acids in the signals needed for N-linked glycosylation). These signals have the amino acid sequence Asn-Xaa-Ser/Thr where Asn is asparagine, Xaa is any amino acid except proline, and Ser/Thr are serine or threonine. To disrupt glycosylation, Asn can be changed to any other amino acid, Xaa can be changed to proline and/or Ser or Thr can be changed to any other amino acids.

Using genetic deglycosylation, it has been shown that the oligosaccharide from the hCG α-subunit at Asn52 has the greatest influence on signal transduction (10). Removal of this oligosaccharide leads to a substantial loss in hormone efficacy and enables the preparation of a partial agonist that can partially inhibit the response to hCG. However, because the other hormone oligosaccharides also influence signal transduction, preparation of the most potent antagonists requires that other N-linked amino acids, particularly those on the α-subunit, be removed from the hormone (10). Unfortunately, removal of the α-subunit oligosaccharide at Asn52 reduces the abilities of the α- and β-subunits to combine (10,14–16). While small amounts of heterodimer do form and can be studied in a laboratory setting (10), preparation of larger quantities needed for potential therapeutic uses is impractical. Methods for improving the production of deglycosylated glycoprotein hormone analogs are desirable and, as described later, one such method involves addition of dimerization sequences to the hormone subunits.

Hormone analogs that have prolonged half-lives or universal activities also have potential important uses. It is well known that the half-lives of the subunits is significantly shorter than that of the heterodimers [reviewed in Moyle and Campbell (2)]. Because dimerization domains can potentiate formation of heterodimers, they can also reduce the rate of hormone dissociation and influence circulation time. Hormone analogs that serve as immunogens are also potentially important. Dimerization domains can contain high immunogenic amino acid sequences and therefore increase the immunogenicity of the analogs.

Structures of the Glycoprotein Hormones

The structures of the glycoprotein hormones have been studied for many years and the relative roles of the hormone subunits in receptor binding specificity are well-known (1). Glycoprotein hormones share a common α-subunit and differ in their hormone-specific β-subunits. The latter determine the biological and immunological properties of each hormone. Substitution of the α-subunit of any one hormone for that of another does not change the receptor binding properties of the new hormone. Substitution of the β-subunit is accompanied by a change in receptor binding specificity. Thus, when FSH β-subunit is substituted for the LH β-subunit, the recombined hormone acquires the properties of FSH and loses properties characteristic of LH. The sequences of many hormone subunits were determined several years ago and have been confirmed by their genomic and cDNA sequences (17–21).

The crystal structure of hCG determined in two laboratories (22,23) showed that each subunit had the overall topology characteristic of cysteine knot proteins (24). Each subunit is divided into three large loops by disulfide bonds that create the cysteine knot. Since the relative positions of the cysteines in all the glycoprotein hormones are very similar, it is nearly certain that the β-subunits of LH, FSH, and TSH will also have a cysteine knot architecture. The β-subunit differs from the α-subunit in one important aspect, namely the presence of an additional sequence of approximately twenty amino acids that is attached to the C-terminal cysteine of the cysteine knot. In the β-subunits of hLH, hCG, hFSH, and hTSH, the seatbelt corresponds to amino acid residues Gly91-Cys110, Ala91-Cys110, Gly85-Cys104, and Gly86-Cys105, respectively. This sequence was termed the seatbelt (22) because it is wrapped around the α-subunit and forms a disulfide bond with a cysteine in β-subunit loop 1 to stabilize the heterodimer. As reviewed by Ruddon and colleagues, the cysteine knot that latches the seatbelt appears to be one of the final steps in β-subunit folding and appears to occur after the two subunits have combined (25).

Several attempts have been made to identify portions of the α- and β-subunits of the hormones that are responsible for their unique biological properties. Earlier studies were based on chemical modifications of the hormones (1). Modifications were described that reduced the biological activities of the hormones. Due to the complexity of the hormones, this approach was usually unable to identify single amino acid residues that were involved in receptor binding or binding specificity. In an attempt to simplify the problem of identifying residues involved in receptor binding, some investigators prepared synthetic peptides corresponding to partial sequences of the α- and β-subunits and monitored their abilities to inhibit binding of $^{125}$I-hCG and $^{125}$I-hFSH to LH and FSH receptors. Synthetic peptides corresponding to amino acid residues of hCG β-subunit 38–57 or hFSH β-subunit 31–52 appear to have higher abilities than most other peptides in these assays (26–29). However, they have extremely low affinities for the receptors, an observation that precludes their practical use.

A breakthrough in the ability to make and characterize glycoprotein hormone analogs came in 1985 when genetically engineered mammalian cells were first shown to express biologically active hCG heterodimers (30). Since that time several laboratories have used mammalian cells to express glycoprotein hormone analogs that are capable of binding to receptors and inducing or inhibiting signal transduction (14,31–37). These analogs appear to be glycosylated similarly to the naturally occurring hormones. In these procedures one introduces a "gene" that encodes the desired amino acid sequences into mammalian cells downstream of a promoter. Construction of these genes is a standard recombinant DNA procedure. By changing, adding and/or deleting codons in the hormone α- or β-subunit cDNAs or genomic DNA fragments using standard procedures, it is possible to build gene constructs that encode the desired analogs (38, 39). When these constructs are transfected into mammalian cells by calcium phosphate precipitation, electroporation, or other standard protocols (38–40), they direct the synthesis of the hormone analogs and their secretion into the culture media. These media can be assayed for the presence of immunological or biological activity (31,32,41). Unfortunately, not all such constructs yield practical amounts of heterodimers. This is especially evident with hormones that lack one or more glycosylation signals.

Using mammalian cell expression systems to make hormone analogs, Campbell, et al. (31) showed that it was possible to switch the receptor binding activity of hCG. They engineered an analog that was chemically and immunologically more similar to hCG than hFSH, but that bound to FSH receptors much better than hCG and had only slightly higher affinity for LH receptors than FSH. Subsequent reports (33) showed that it was possible to prepare analogs of hCG that had a high affinity for both LH and FSH receptors. This was accomplished by replacing hCG seatbelt residues 101–109 with their hFSH β-subunit counterparts (i.e., hFSH β-subunit residues 95–103). These hCG analogs (31,33) elicit signal transduction at either LH and/or FSH receptors. This demonstrated that the seatbelt of the β-subunit had a major influence on receptor binding specificity. It is anticipated that removing the oligosaccharides from analogs in which the specificity is modified by substitutions in the seatbelt will reduce their efficacy and cause them to become partial agonists and/or antagonists. Their ability to bind to receptors requires that the β-subunits of these analogs combine with the α-subunit to form heterodimers. The method described here will be useful for expressing these analogs as heterodimers and represents a significant advance in heterodimer preparation.

Slaughter et al. (42) showed that an interaction between the N-terminal portion of hCG β-subunit and the seatbelt had a substantial influence on subunit combination. Removal of the hCG β-subunit N-terminus led to loss in its ability to combine with the α-subunit to form a heterodimer. This could be restored in part by changing the seatbelt residues of the β-subunit to those found in the β-subunit of hFSH. This suggested that interactions between different parts of the hormone subunits had significant roles in subunit combination. It also suggested that subunit combination was complex and that any modification of this region of the hCG β-subunit might be expected to interfere with subunit combination. Indeed, work by Keutmann and colleagues (43) showed that synthetic peptides similar in structure to the N-Terminal region of the hCG β-subunit inhibited subunit combination and that this portion of hCG was likely to be near the α-subunit.

Sugahara et al. (44) showed that a fusion protein between the α- and β-subunits would lead to a protein that had many of the same properties as the heterodimeric parental molecule, including the ability to bind to receptors. Nonetheless, these analogs have all the amino acids of the protein connected together in a single-chain and therefore differ substantially from proteins that have two subunits. Unlike single chain proteins that are folded differently from the native hormones, hormone analogs that have two separate subunits similar to those found naturally would be expected to have receptor binding and immunological properties that are more similar to those of the parental molecules.

BRIEF DESCRIPTION OF THE FIGURES

FIG. 1 illustrates the coding sequence of the hCG β-subunit cDNA between the XhoI and BamHI sites except that the codons for amino acids 2–8 have been deleted.

FIG. 2 illustrates the coding sequence of a vector that encodes the hCG β-subunit signal sequence upstream (5') of bases that encode serine, cysteine, two glycines, and portions of the Fos dimerization domain (one letter code).

FIG. 3 illustrates the coding sequence of a vector that encodes the hCG β-subunit signal sequence upstream (5') of bases that encode serine, cysteine, two glycines, and portions of the Jun dimerization domain (one letter code).

FIG. 4 illustrates the sequences of oligonucleotides used in this work including primers used to create a cassette that permitted insertion of the Fos and Jun dimerization domain amino acid coding sequences into the construct illustrated in FIG. 1.

FIG. 5 shows the coding sequence of the entire Fos-hCG-α-subunit construct.

FIG. 6 shows the coding sequence of the entire Jun-hCGβ'-subunit construct.

FIG. 9 illustrates the sequence of an α-subunit construct that is lacking the glycosylation signal normally found at Asn52 of the mature human α-subunit.

FIG. 10 illustrates the sequence of the Fos-α-subunit construct that is lacking the glycosylation signal corresponding to human α-subunit residue 52 caused by substitution of an aspartic acid residue for the asparagine normally found at this residue of the human α-subunit.

FIG. 11 illustrates the sequence of the Fos-α-subunit construct in which the cysteine normally found at position 7 of the human α-subunit has been replaced by an alanine.

FIG. 12 illustrates the sequence of the Jun-hCGβ'-subunit in which the tyrosine normally found in the hCG β-subunit at residue 37 has been replaced by a cysteine.

FIG. 13 illustrates the Jun-hCGβ'-Y37C-C26A construct.

FIG. 14 illustrates the Jun-hCGβ'-Y37C-C26A-δ92 construct.

FIG. 17 illustrates the sequences of constructs of Fos-hCG α-subunit containing a furin cleavage site and the sequences of Jun-hCG β-subunit, Jun-hLH β-subunit, Jun-hFSH β-subunit, Jun-hTSH β-subunit, Jun-hCG/hFSH β-subunit chimera, and Jun-hCG/hTSH β-subunit chimera containing a furin cleavage site.

FIG. 18 illustrates the sequences of constructs containing immunoglobulin dimerization domains at their N-termini.

FIG. 19 illustrates the sequences of constructs containing immunoglobulin dimerization domains at their N-termini.

FIG. 20 illustrates the amino acid sequences of β-subunit constructs containing the dimerization domain from Jun at the carboxyterminus of their dimerization domains.

SUMMARY OF THE INVENTION

Figure 7:
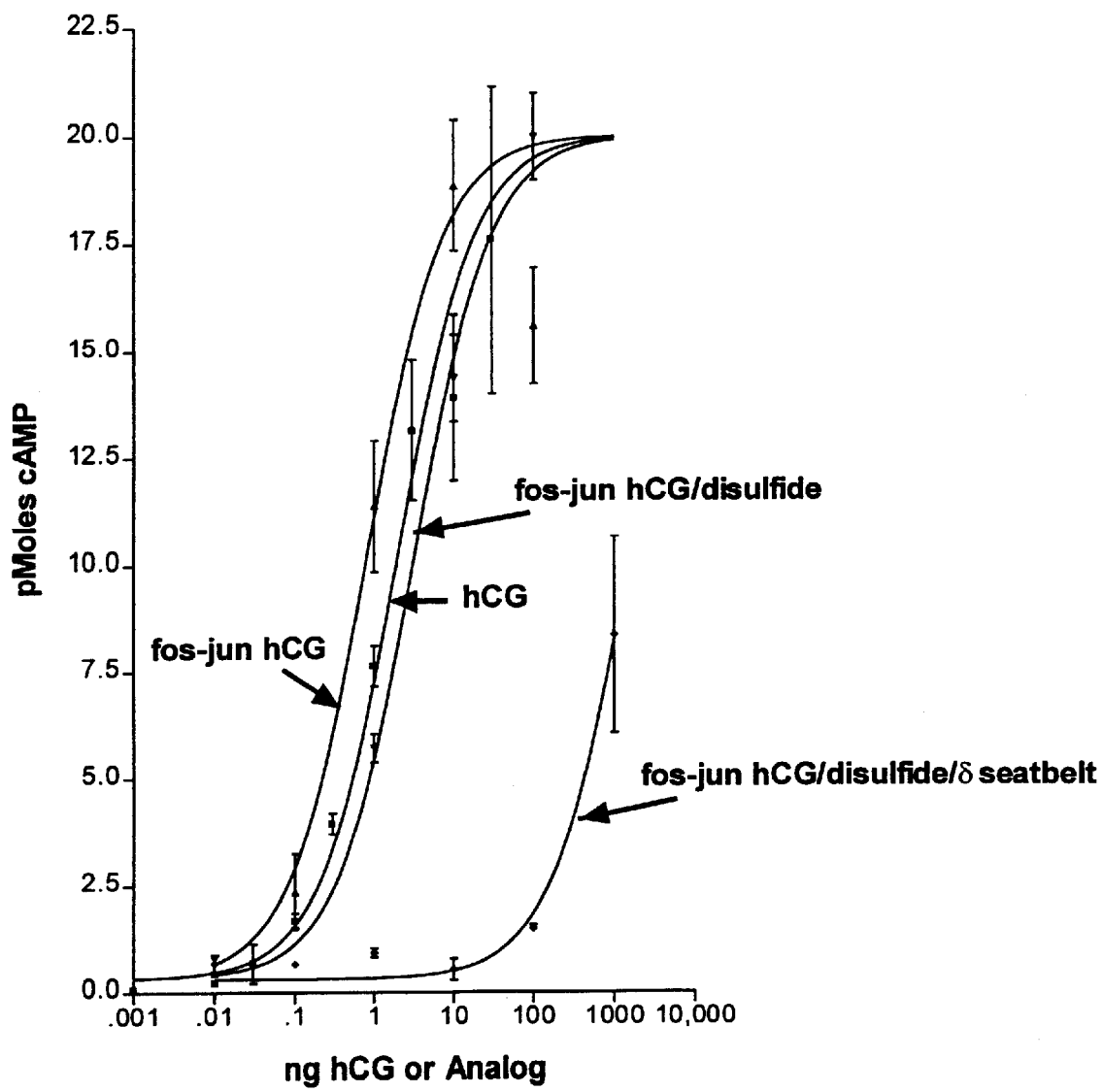
FIG. 7 shows that the heterodimer containing the Fos-Jun amino acid sequences at its N-termini can stimulate signal transduction in a similar fashion as hCG.

The present invention pertains to a method for forming a subunit combination of a cysteine knot protein having an α-subunit and a β-subunit to prepare a heterodimeric protein analog which comprises the steps of:
  (a) attaching a dimerization domain to the amino termini of both an α-subunit and a β-subunit of a cysteine knot protein; and
  (b) dimerizing the α-subunit and β-subunit to form a heterodimeric protein analog.

In a preferred embodiment, a Fos dimerization sequence domain is attached to the amino-terminus of the β-subunit and a Jun dimerization sequence domain is attached to the amino-terminus of the α-subunit. In another preferred embodiment, a Fos dimerization sequence domain is attached to the amino-terminus of the α-subunit and a Jun dimerization sequence domain is attached to the amino-terminus of the β-subunit. A glycine or serine residue may be inserted between the Fos or Jun dimerization sequence domain and a furin cleavage site to facilitate cleavage of the dimerization sequence domain from the heterodimer. The dimerization domain may also be a heavy or light chain of an immunoglobulin. The heterodimeric protein analog may be a glycoprotein hormone heterodimer selected from the group consisting of hCG, hLH, hFSH, hTSH, TGFβ, PDGF, NGF, Veg1, bone morphogenic proteins, activin, inhibin, and analogs thereof. The heterodimeric protein analog may also be selected from the group consisting of hCG/hFSH chimeras, hCG/hTSH chimeras, deglycosylated hormones, truncated glycoprotein hormones, mutant glycoprotein hormones, and glycoprotein hormones containing an hCG carboxyl terminus. Protease cleavage sites may be incorporated between additional N-terminal sequences and the α-subunit and the β-subunit of the cysteine knot protein to remove the dimerization domains from the heterodimeric protein analog. The cysteine knot protein may be a glycoprotein hormone heterodimer having the oligosaccharide genetically removed from the α-subunit at Asn52. The cysteine knot protein may also be a glycoprotein hormone heterodimer lacking a seatbelt.

In another embodiment, the present invention pertains to a method for forming a subunit combination of a cysteine knot protein having an α-subunit and a β-subunit to prepare a heterodimeric protein analog which comprises the steps of:
  (a) attaching a dimerization domain to the amino terminus of an α-subunit and the carboxy terminus of a β-subunit of a cysteine knot protein; and
  (b) dimerizing the α-subunit and β-subunit to form a heterodimeric protein analog.

In a preferred embodiment, a Fos dimerization sequence domain is attached to the carboxy-terminus of the β-subunit and a Jun dimerization sequence domain is attached to the amino-terminus of the α-subunit. In another preferred embodiment, a Fos dimerization sequence domain is attached to the amino-terminus of the α-subunit and a Jun dimerization sequence domain is attached to the carboxy terminus of the β-subunit. A protease cleavage site may be inserted between the dimerization sequence domain and the α-subunit and a protease cleavage site may be inserted between the dimerization sequence domain and the β-subunit. Preferably, the protease cleavage site is furin. The dimerization domain may be a heavy or light chain of an immunoglobulin. The heterodimeric protein analog may be selected from the group consisting of hCG/hFSH chimeras, hCG/hTSH chimeras, deglycosylated hormones, truncated glycoprotein hormones, mutant glycoprotein hormones, and glycoprotein hormones containing an hCG carboxyl terminus. The cysteine knot protein may be a glycoprotein hormone heterodimer having the oligosaccharide genetically removed from the α-subunit at Asn52.

DETAILED DESCRIPTION OF THE INVENTION

Human chorionic gonadotropin (hCG), luteinizing hormone (LH), follicle stimulating hormone (FSH), and thyroid stimulating hormone (TSH) are members of the heterodimeric glycoprotein hormone family. LH and hCG bind to LH receptors (LHR), FSH binds to FSH receptors (FSHR), and TSH binds to TSH receptors (TSHR). Interactions of LH and FSH with gonadal LHR and FSHR are essential for fertility. Interactions of TSH with TSHR are essential for proper functioning of the thyroid gland. All four hormones are heterodimers containing an α-subunit produced from the same gene and a hormone-specific β-subunit. The crystal structure of hCG shows that both subunits are members of the cysteine knot family of proteins. Because the endocrine activities of the heterodimers exceed those of the isolated subunits, it is usually desirable to prepare heterodimers in which the α- and β-subunits are combined similarly to the native hormones. Formation of non-native or mutant heterodimers is often impeded by changes to one or both subunits needed to elicit desirable properties. The present method promotes subunit combination of the cysteine knot family of proteins and thereby improves the synthesis of heterodimeric hormone analogs. This method involves attaching dimerization domains to the amino termini of both hormone subunits, a process that facilitates combination of the remainder of the proteins into active heterodimers. By incorporating appropriate protease cleavage sites between the additional N-terminal sequences and the α- and β-subunits, it is also possible to remove the dimerization domains from the hormone dimers to create hormone analogs that are similar in structure to the native molecules.

By employing the method of the present invention, it is possible to increase the efficiency of subunit combination for subunits that would otherwise not combine or that would combine very poorly by adding sequences dimerization domains to the N-terminus of each subunit. This method can also be applied to the preparation of glycoprotein hormone heterodimers in which the oligosaccharide has been genetically removed from the α-subunit at Asn52. This method can also be used to produce heterodimers lacking the seatbelt. The method outlined in this invention should be useful for facilitating the dimerization of any cysteine knot proteins including but not limited to TGFβ, PDGF, NGF, Veg1, bone morphogenic proteins, activin, inhibin and their analogs. The present invention also teaches that the N-terminal portions of the glycoprotein hormones can be modified without disrupting the activity of the protein.

The dimerization domain strategy can be used to prepare any heterodimeric analog of the glycoprotein hormones, glycoprotein hormone including hCG/hFSH and hCG/hTSH chimeras (31,33,48,52) and/or deglycosylated hormones including those missing oligosaccharides at one or more positions on the α- or β-subunits (10), truncated glycoprotein hormone subunits, glycoprotein hormone subunits containing the hCG carboxyl terminus (52), glycoprotein hormones from different vertebrates, glycoprotein hormones in which the subunits are derived from different species, and heterodimers of other members of the cysteine knot family. Most members of the cysteine knot family with the exception of the glycoprotein hormones contain their own dimerization domains that are included in the "pro" portion of the prohormone. Dimerization domains from these other cysteine knot proteins can be substituted for the Fos and Jun sequences described above to promote dimerization of the glycoprotein hormones. In addition, the use of Fos, Jun, or other dimerization domains will facilitate production of heterodimeric cysteine knot proteins. For example, inhibin is composed of an α- and a β-subunit. When these are expressed in the same cell there is the potential for the formation of activin, a ββ homodimer, particularly when the Fos dimerization sequence is added to the N-terminus of the β-subunit and the Jun dimerization sequence is added to the N-terminus of the α-subunit. Use of the Fos-Jun or other heterodimerization strategy outlined here is expected to reduce the formation of these homodimers and facilitate the production of heterodimers that inhibit rather than potentiate FSH secretion. It should also be noted that the furin cleavage site can be replaced with other cleavage sites. In addition, residues such as glycine and/or serine can be inserted between the Fos or Jun and the furin cleavage sites to facilitate cleavage of the dimerization domain from the remainder of the heterodimer. The heterodimers produced by addition of the dimerization domains will retain the properties of the native or mutant hormones produced without the presence of the dimerization domains. The heterodimers produced by addition of the dimerization domains will also serve as useful antigens. Thus, when the dimerization domain is retained on the protein, its antigenicity will be enhanced. When the dimerization domain is used to produce a protein containing a subunit or part of a subunit from a different species, its antigenicity will also be enhanced.

EXAMPLE 1

Preparation and Characterization of Fos-Jun hCG, an hCG Analog Containing the Dimerization Domain of Fos Attached to the N-terminus of the α-subunit and the Dimerization Domain of Jun Attached to the N-terminus of the β-subunit The hCG β-subunit cDNA was modified to add an NheI restriction endonuclease site at the end of the leader sequence (FIG. 1). This enabled insertion of the dimerization domains of Fos or Jun at the C-terminal end of the hCG β-subunit signal sequence. The modification was made by manipulating the sequence of the naturally occurring hCG β-subunit cDNA starting with vectors that have been described (31,32,42). The coding sequence of the resulting vector is shown in FIG. 1. When this coding sequence is expressed in mammalian cells, the signal sequence (i.e., amino acids MEMFQGLLLLLLLLSMGGTWA, (SEQ. ID NO: 384) single amino acid code) will be removed and like the hCG β-subunit, the resulting protein should have a serine residue at its N-terminus. The codons between the NheI and BamHI restriction sites shown in FIG. 1 were replaced with bases that included the coding sequences for the portions of the Fos and Jun dimerization domains capable of forming heterodimers. This created the constructs shown in FIGS. 2 and 3. The Fos construct was prepared by annealing oligonucleotides 1002 and 1003 (FIG. 4) and filling them in with Vent Polymerase (New England Biolabs, Beverly, Mass.). Oligonucleotides 1004 and 1005 (FIG. 4) were used in a polymerase chain reaction (PCR) with the filled-in product of oligonucleotides 1002 and 1003 to produce a DNA fragment approximately 175 base pairs long. This was purified by agarose gel electrophoresis, digested with NheI and BamHI and the large fragment that resulted was subcloned into the NheI-BamHI sites of the construct shown in FIG. 1 to produce the construct shown in FIG. 2. The Jun construct (FIG. 3) was prepared in a similar fashion except that oligonucleotides 1006 and 1007 (FIG. 4) were used for the fill-in reaction and oligonucleotides 1008 and 1009 (FIG. 4) were used for PCR.

Following DNA sequencing to make certain that the complex having the desired codons had been obtained, the construct containing the Fos codons described in FIG. 2 was digested with BsmI and BamHI. The short piece of DNA between these sites was replaced with the BsmI-BamHI digestion product of the human α-subunit cDNA to create the construct containing the codons illustrated in FIG. 5. The final coding construct shown in FIG. 5 was then subcloned into an expression vector (pCI') that was a modification of pCI, a vector obtained from promega, Madison, Wis. and created pCI'-Fos-α. The modification of pCI to create pCI' consisted of moving the BamHI site from a region outside the polyadenylation signal to a position near the 3' end of the polylinker. This was accomplished using the polymerase chain reaction and was done to facilitate cloning the coding constructs into the expression vector. It is not necessary to use this vector to observe expression in mammalian cells. Virtually any vector capable of expressing proteins in mammalian cells will suffice including that known as pSVL, commercially available from Pharmacia Co., Piscataway, N.J. pSVL can be used directly without modification since it contains a polylinker with appropriately positioned XhoI and BamHI sites to facilitate the cloning and expression of the protein.

Using a similar strategy, a DNA construct that encodes a sequence having the hCG β-subunit leader, a segment related to the Jun oncoprotein, and the hCG β-subunit was prepared. The construct shown in FIG. 3 was digested with BspMI and BamHI and the small fragment that was produced was replaced with the fragment obtained from pKBM-hCGβ' (31) by digestion with BamI and BamHI to create the construct shown in FIG. 6. XhoI-BamHI fragment obtained from the resulting construct was ligated into the pCI' expression vector using the XhoI-BamHI sites to create pCI'-Jun-hCGβ'. As noted earlier, it would not be necessary to use pCI' for this purpose. pSVL has the appropriate restriction sites and would permit expression of the protein in COS-7 cells.

PCI'-Fos-α and pCI-Jun-hCGβ' were co-transfected into CHO cells using a calcium phosphate method as described (31) to cause the secretion of heterodimers comprised of Fos-a and Jun-hCGβ'. The heterodimers were recognized by monoclonal antibodies to the hCG α- and β-subunits A113 and B112, respectively (45,46). These specific antibodies are not required to measure the presence of heterodimers in the cell culture media and nearly any monoclonal or polyclonal antibodies that have epitopes on the surface of hCG α- and β-subunits that does not involve the N-terminus of the α- or β-subunits will be adequate. The Fos-α/Jun-hCGβ' heterodimer stimulated signal transduction (cyclic AMP accumulation) in CHO cells that express the rat LH receptor with approximately the same potency as hCG (FIG. 7). This showed that the addition of the dimerization domains to the N-termini of both subunits did not adversely affect the biological activity of hCG.

This construct inhibited binding of 125I-hCG to cells that express LH receptors with approximately equal potency as hCG that had been purified from urine (FIG. 8) indicating that the presence of the Fos and Jun sequences on the N-termini of the subunits did not interfere with receptor interaction. Methods for monitoring binding of radioiodinated hCG to LH receptors have been described previously (31,33,45–48) and are well-known in the art.

EXAMPLE 2

Preparation and Characterization of Fos-Jun hCGαδ2, an hCG Analog Containing the Dimerization Domain of Fos Attached to the N-terminus of the α-subunit Lacking the Glycosylation Signal at α-subunit Residue 52 and the Dimerization Domain of Jun Attached to the N-terminus of the β-subunit Removal of the oligosaccharide normally found on the human α-subunit at residue 52 reduces the ability of the α-subunit analog to combine with the hCG β-subunit (10). This example shows that addition of the Fos dimerization domain to an α-subunit analog lacking the glycosylation signal responsible for adding an oligosaccharide at residue 52 (Fos-αδ52) facilitated formation of heterodimers with Jun-hCGβ'.

A construct encoding the human α-subunit lacking the glycosylation signal at residue 52 was prepared by PCR mutagenesis. Oligonucleotides 739 and 839 (FIG. 4) were used as primers and pKBM-α (31) as template to create an α-subunit construct (pMB507) encoding a glutamine at residue 52 and to introduce BglII and SpeI restriction endonuclease sites. A second PCR was performed using oligonucleotides 850 and 851 (FIG. 4) as primers and pKBM-α (31) as template to create an α-subunit construct encoding an aspartic acid at residue 52 and a glutamine at residue 78. The BglII-SpeI fragment of this construct was subcloned into the BglII-SpeI sites of pMB507 to create an α-subunit construct encoding an aspartic acid corresponding to human α-subunit residue 52. The coding sequence of this mutation (FIG. 9) was confirmed by dideoxy DNA sequencing. Although this sequence also adds silent restriction sites for BglII and SpeI to facilitate preparation of additional mutants, these are not needed to express an analog lacking the oligosaccharide at amino acid 52. Construction of the vector encoding Fos-αδ52 was similar to that encoding Fos-α except that the construct encoding the αδ52-subunit (FIG. 9) was used in place of that encoding the α-subunit to create the sequence shown in FIG. 10.

Co-expression of Fos-αδ52 and Jun-βsubunits in COS-7 cells led to secretion of heterodimer that could be readily detected in a sandwich radioimmunoassay (41) using monoclonal antibodies A113 and B112 to the α- and β-subunits of hCG. Under these same conditions, much lower amounts of heterodimer were obtained by co-expression of αδ52 and hCG-β subunits lacking the Fos and Jun dimerization domain in COS-7 cells. This showed that the presence of the Fos and Jun sequences at the N-termini of the αδ52- and β-subunits facilitated dimer formation. These results are shown in Table 1.

TABLE 1

Formation of hCG heterodimers in which the α-subunit is missing an glycosylation signal needed for efficient subunit combination.

| Subunit Combination | Amount of Heterodimer* |
|---|---|
| No heterodimer (blank) | 2554 ± 215 |
| hCG α + hCG β | 15281 ± 493 |
| Fos-αδ52 + Jun-hCGβ' | 25506 ± 750 |

TABLE 1-continued

Formation of hCG heterodimers in which the α-subunit is missing an glycosylation signal needed for efficient subunit combination.

| Subunit Combination | Amount of Heterodimer* |
|---|---|

*Values represent the results of sandwich immunoassays in which the analyte was captured using an anti-α-subunit antibody (A113) and detected using a radioiodinated anti-β-subunit antibody (B112). The amount of culture media used in each assay was identical (50 μl). the higher the number of counts bound in the assay, the greater the amount of heterodimer. The presence of the Fos-Jun dimerization domain increased the ability of the deglycosylated α-subunit to combine with hCG β-subunit to at least as high a level as that seen for hCG.

EXAMPLE 3

Preparation and Characterization of Fos-Jun hCG Analogs Containing the Dimerization Domain of Fos Attached to the N-terminus of the α-subunit and the Dimerization Domain of Jun Attached to the N-terminus of the β-subunit Lacking the Seatbelt or with a Seatbelt that Cannot be Latched The seatbelt is known to be essential for heterodimer formation. Mutations that disrupt the seatbelt or disrupt the seatbelt latch prevent subunit combination (49). Use of a dimerization domain can enable the formation of glycoprotein hormone analogs that lack the seatbelt and that are able to stimulate signal transduction.

The coding sequence of hCG β-subunit was modified to eliminate the seatbelt latch by replacing Cys26 with alanine. Some other analogs were prepared in which the coding sequence was truncated after the codon for amino acid 92. In addition, to increase the probability that the two subunits would be held together in the heterodimer lacking a properly closed seatbelt in the same orientation as they would be in hCG, an intersubunit disulfide was engineered between the two subunits. This disulfide was placed between the two cysteine knots corresponding to residue 31 from the α-subunit and residue 38 from the β-subunit. Residue 31 is already a cysteine in the α-subunit and normally forms a disulfide with the cysteine at α-subunit residue 7. Changing Cys7 to alanine, provided a free disulfide from the α-subunit for use in the intersubunit disulfide. It's counterpart in the β-subunit was created by changing Tyr37 to cysteine.

The coding sequences of Fos-αC7A, Jun-hCGβ'Y37C, Jun-hCGβ'Y37C/C26A, and Jun-hCGβ'Y37C/C26A5Seatbelt are illustrated in FIGS. 11, 12, 13, and 14, respectively. These were prepared using a combination of PCR and cassette mutagenesis starting with constructs that have already been described. Fos-αC7A (FIG. 11) was prepared by taking advantage of the fact that the construct encoding Fos-α contains HindIII and BspEI endonuclease restriction sites on either side of the codon corresponding to human α-subunit Cys7. Fos-αC7A was prepared by replacing the small HindIII-BspEI fragment of the coding vector for Fos-α with a cassette prepared from oligonucleotides 1053 and 1054 (FIG. 4). The coding sequence of Jun-hCGβ'Y37C (FIG. 12) was prepared by taking advantage of the fact that the pKBM-hCGβ' (31) contains NgoMI and PstI endonuclease restriction sites surrounding the codon to be changed (i.e., hCG β-subunit Tyr37). Jun-hCGβ'Y37C was prepared in two steps. First, the small NgoMI-PstI site in pKBM-hCGβ' was replaced with a cassette prepared by annealing oligonucleotides 845 and 877 (FIG. 4). Second, the fragment of pKBM-hCGβ' between the BanI and BamHI sites was cloned into the BspMI-BamHI sites of the vector illustrated in FIG. 3 to create the coding sequence of Jun-hCGβ'Y37C. The coding sequence of Jun-hCGβ'Y37C/C26A (FIG. 13) was prepared using oligonucleotides 1026 and 1027 (FIG. 4). These were annealed and filled-in to create a cassette having AvrII and NgoMI restriction sites at its ends. This was digested with AvrII and NgoMI and the resulting fragment was cloned into the AvrII-NgoMI fragment of Jun-hCGβ'Y37C. The coding sequence of Jun-hCGβ'Y37C/C26AΔ92 (FIG. 14) was prepared by replacing the XhoI-PvuII fragment of a truncated hCG β-subunit construct with that from Jun-hCGβ'Y37C/C26A. The truncated hCG β-subunit construct had been prepared in two steps. First, the PvuII-BamHI fragment was replaced with a cassette prepared by annealing and filling-in oligonucleotides 435 and 436 (FIG. 4). This cassette was digested with PvuII and BamHI sites and cloned into the PvuII-BamHI fragment of pKBM-hCG β' (31). This created a BssHII site at the codons for hCG β-subunit amino acids 90–92. The truncated hCG β-subunit was prepared by replacing the BssHII-BamHI fragment of this construct with a cassette prepared by annealing oligonucleotides 837 and 838 (FIG. 4).

Fos-αC7A was co-expressed in CHO and/or COS-7 cells with Jun-hCGβ'Y37C, Jun-hCGβ'Y37C/C26A, or Jun-hCGβ'Y37C/C26AΔ92 to yield heterodimers Fos-Jun-hCG-SS, Fos-Jun-hCG-SS-δlatch, or Fos-Jun-hCG-SS-δseatbelt. The heterodimers were readily detected in assays employing A113 and $^{125}$I-B112 for capture and detection, respectively. The activities of Fos-Jun-hCG-SS and Fos-Jun-hCG-SS-δseatbelt were determined in signal transduction assays (FIG. 7). The presence of the second intersubunit disulfide in Fos-Jun-hCG-SS reduced the activity of Fos-Jun-hCG slightly in signal transduction assays (FIG. 7) and in receptor binding assays (FIG. 8) as can be seen by comparing the activities of and Fos-Jun-hCG in both assays. The analog lacking the seatbelt was much less active than that of hCG, Fos-Jun-hCG, and Fos-Jun-hCG-SS indicating that the seatbelt had a substantial influence on the activities of hCG in these assays. However, the presence of the Fos-Jun dimerization enabled production of sufficient heterodimer to be able to detect the activities of the material lacking the seatbelt. Without a dimerization domain, it would have been nearly impossible to prepare sufficient heterodimer lacking the seatbelt to test its activity.

These analogs were also tested in FSH and TSH signal transduction assays. hCG has very low ability to stimulate signal transduction in cells containing FSH or TSH receptors (50). The presence of Fos and Jun did not increase the ability of hCG to elicit signal transduction in cells expressing either FSH (FIG. 15) or TSH receptors (FIG. 16). Thus, the presence of the dimerization domain did not alter receptor specificity. In addition, the presence of the disulfide did not influence receptor specificity. The analog lacking the seatbelt had low activity, however, its activity in the FSH and TSH assays was only slightly lower than its activity in the LH receptor signal transduction assays. This shows that the presence of the dimerization domain would not be expected to alter receptor interaction or specificity. However, removing the seatbelt increased the maximal amount of signal transduction that could be obtained in TSH assays (FIG. 16).

EXAMPLE 4

Fos-Jun hCG Analogs Containing Domains that can be Cleaved During Synthesis in Eucaryotic Cells The dimerization domains of the analogs whose sequences are described in FIGS. 5, 6, and 9 remain associated with the heterodimers. In some cases such as when the heterodimer is to be used as an antigen or a pharmaceutical compound, it may be desirable to remove the dimerization domain. This can be accomplished by a variety of proteolytic methods including digestion with aminopeptidases and/or endopeptidases. In the latter case it usually necessary to incorporate a specific endopeptidase restriction site between the dimerization sequence and the protein to be produced. Many of these are well-known in the art and include the sequences recognized by enterokinase (i.e., DDDDK, (SEQ ID NO: 34) single letter amino acid code) and FactorXa (i.e., IEGR, (SEQ ID NO: 52) single letter amino acid code). It is also possible to include a furin cleavage sequence in this location as illustrated in FIG. 17. The protein heterodimer to be produced is expected to form a heterodimer in the lumen of the endoplasmic reticulum and then be cleaved by a furin protease located in a downstream part of the secretion pathway. This strategy has the advantage in that it does not require protease digestion of the secreted product.

EXAMPLE 5

Addition of Dimerization Domains to Other Glycoprotein Hormones

Fos-Jun constructs similar to those described in Example 1 can be prepared from other glycoprotein hormone α- and β-subunits including those of hLH, hFSH, hTSH and other vertebrate glycoprotein hormones. FIG. 17 lists the amino acid sequences of some of these with the presence of the furin cleavage site. Addition of the N-terminal dimerization domains would be expected to increase the efficiency of heterodimer formation, particularly with α- and β-subunit analogs that do not readily dimerize. Production and analysis of these analogs would be similar to that of Fos-Jun hCG. It would involve their expression in eucaryotic cells, measurement in sandwich immunoassays using antibodies to the α-subunit for capture and radiolabeled antibodies to the β-subunit for detection, and assay using CHO cells expressing LH, FSH, or TSH receptors. By analogy to Example 4, it should be possible to include endopeptidase sites to cleave the dimerization domain. It should be noted that the location of the furin site shown is not essential to produce these proteins as heterodimers.

EXAMPLE 6

Addition of Different Dimerization Domains to Enhance the Formation of Glycoprotein Hormone Heterodimers It is not necessary to use the Fos-Jun dimerization strategy to enhance the formation of heterodimers. Addition of nearly any other dimerization domains should suffice. This includes any coiled-coil pair that forms heterodimers. These would be introduced onto the α- and β-subunits of the glycoprotein hormones in a fashion similar to that used to prepare the Fos-Jun analogs. Alternatively, it would be possible to modify the sequences of the Fos and Jun sequences to create additional coiled-coils. Methods for producing and aligning coiled-coils are well known in the art (51). One could also use the heavy and light chains of the immunoglobulins to promote dimerization. An example of the use of the light chain coupled to the α-subunit and the heavy chain coupled to the β-subunit is illustrated in FIGS. 18 and 19. This could also be reversed such that the light chain is coupled to the β-subunit and the heavy chain is coupled to the α-subunit. Since the heavy and light chains of the antibodies can be selected to bind to various targets, this approach has the additional advantage of enabling one to direct the heterodimers to particular tissues that contain binding sites for the antibodies. By incorporating an enzyme cleavage site, it would be possible to obtain selected release of the hormones from the antibodies at the site in which they had been localized by the presence of the immunoglobulins. The sequences shown in FIGS. 18 and 19 illustrate furin cleavage sites between the immunoglobulin domains and the α- and β-subunits. These could be replaced by any target-specific cleavage site to promote release of the heterodimeric glycoprotein hormone or hormone analog at a desired location. Further, it would be possible to include a furin cleavage site in only the light chain—α-subunit construct or the heavy chain—β-subunit construct and to include a target-specific cleavage site in the other subunit construct at the location shown in FIGS. 18 or 19 by the furin sites. It should be noted that the constructs illustrated in FIG. 18 will be crosslinked by a disulfide near the junction of the immunoglobulin constant domains with the α- and β-subunits. This disulfide may constrict the conformation of the subunits and reduce their activities. To eliminate this, the cysteine near this junction should be replaced with an alanine. Finally, it should be noted that the immunoglobulins illustrated are from the mouse. This would not be expected to be a requirement for the immunoglobulin domain to facilitate subunit combination or targeting. Thus, one could use immunoglobulin domains from other proteins and from other species. The use of immunoglobulin domains from humans would be an advantage for preparing glycoprotein hormone homodimers for use in humans. These domains would also be expected to enhance the half-lives of hormone analogs such as hLH that are known to have short half-live

EXAMPLE 7

Addition of a Dimerization Domain at the C-terminus of the β-subunit that can Form a Heterodimer with a Dimerization Domain Attached to the N-terminus of the α-subunit Another method of forming heterodimers of the glycoprotein hormones involves addition of the coding region for a dimerization domain such as the sequence needed for dimerization of Fos or Jun or any other protein heterodimer to the C-terminus of the β-subunit unit. When this protein is expressed with a protein that has a complementary dimerization domain attached to the N-terminal end of the α-subunit, it will also form a heterodimer. An example of a β-subunit analog that can enhance dimerization of hCG analogs that would otherwise dimerize poorly is illustrated in FIG. 20. This illustrates the hCG β-subunit sequence containing a Jun dimerization domain at its C-terminus. When expressed with an α-subunit construct that encodes a Fos dimerization domain at its N-terminus this will lead to the formation of a heterodimer capable of interacting with LH receptors. α-subunit constructs capable of dimerizing with the β-subunit sequences illustrated in FIG. 20 are illustrated in FIGS. 5 and 10. These α-constructs have the potential to form an intersubunit disulfide bond with the last two β-subunit Jun analogs illustrated in FIG. 20. When this intersubunit bond is not desired, it can be eliminated by removing the codons for the amino acid sequence Cys-Gly-Gly (CGG). It should be noted that it is not necessary to use Fos and Jun sequences to augment dimerization. It should also be noted that because the C-terminus of the glycoprotein hormone β-subunits is not needed for their hormone activities and that the N-terminus of the glycoprotein hormone α-subunits is not needed for their hormone activities, this process could be applied to all the glycoprotein hormones. It should also be noted that the presence of the hCG β-subunit C-terminus can be used to extend the half-life of all the circulating hormones. Thus, it would be expected that addition of the C-terminus of the hCG β-subunit to the C-terminus of the other glycoprotein hormone β-subunits would be useful in preparing this type of heterodimers and eliciting heterodimers that would have prolonged half-lives. It would also be expected that heterodimers in which the dimerization domain was crosslinked by a disulfide bond could be prepared by expressing the α-subunit constructs illustrated in FIGS. 5 or 10 with either of the last two β-subunit constructs illustrated in FIG. 20. This would be expected to stabilize the heterodimer.

FIG. 1 illustrates the coding sequence of the hCG β-subunit cDNA between the XhoI and BamHI sites except that the codons for amino acids 2–8 have been deleted. This sequence contains an NheI restriction site between the codons for alanine and serine (i.e., codons −1 and +1, respectively) and is similar to that described by Slaughter et al. (31). The leader sequence from this vector encodes the same amino acids found in hCG β-subunit and was used to prepare subsequent expression constructs because it enables the proteins to enter the secretion pathway. It should be noted that it is not necessary to use the hCG β-subunit leader for this purpose. Most other known leader sequences can be used to drive secretion.

FIG. 2 illustrates the coding sequence of a vector that encodes the hCG β-subunit signal sequence upstream (5') of bases that encode serine, cysteine, two glycines, and portions of the Fos dimerization domain (one letter code). While this sequence serves well to elicit formation of homodimers, other sequences are expected to work equally well. Indeed, it is expected that most other amino acid sequences known to participate in heterodimer formation will function as a dimerization domain similar to the sequence illustrated in FIG. 2. Dimerization domains can be designed to be similar to proteins or portions of proteins that are known to form coiled coils. They can be derived from other proteins known to form heterodimers such as portions of the heavy and light chains of immunoglobulins. It is not essential to use the sequence "cysteine-glycine-glycine" shown at the N-terminus of the protein in FIG. 2. The sequence "glycine-glycine-cysteine" can also be incorporated at the C-terminal end of the Fos dimerization domain such that the cysteine residue would occupy the position normally occupied by glutamine at residue 5 of the human α-subunit. The cysteine has been incorporated to promote the formation of a disulfide to stabilize the heterodimer.

FIG. 3 illustrates the coding sequence of a vector that encodes the hCG β-subunit signal sequence upstream (5') of bases that encode serine, cysteine, two glycines, and portions of the Jun dimerization domain (one letter code). While this sequence serves well to elicit formation of homodimers, other sequences are expected to work equally well. Indeed, it is expected that most other amino acid sequences known to participate in heterodimer formation will function as a dimerization domain similar to the sequence illustrated in FIG. 3. Dimerization domains can be designed to be similar to proteins or portions of proteins that are known to form coiled coils. They can be derived from other proteins known to form heterodimers such as portions of the heavy and light chains of immunoglobulins. It is not essential to use the sequence "cysteine-glycine-glycine" shown at the N-terminus of the protein in FIG. 3. The sequence "glycine-glycine-cysteine" can also be incorporated at the C-terminal end of the Jun dimerization domain such that the cysteine residue would occupy the position normally occupied by glutamine at residue 6 of the human β-subunit. The cysteine has been incorporated to promote the formation of a disulfide to stabilize the heterodimer.

FIG. 4 illustrates the sequences of oligonucleotides used in this work including primers used to create a cassette that permitted insertion of the Fos and Jun dimerization domain amino acid coding sequences into the construct illustrated in FIG. 1. Each oligonucleotide was synthesized by standard methods. Oligonucleotides 1002 and 1003 (shown in the positions that they hybridize) were mixed and heated to 95° C. for 2 minutes. Vent DNA polymerase (New England Biolabs, Beverly, Mass.) was added and the reaction allowed to cool slowly to 68° C. and maintained at that temperature for 5 min to permit the fill-in reaction to occur. An aliquot of the reaction was added to a second tube containing primers 1004 and 1005 and the tube was heated to 95° C. for 2 minutes. Vent DNA polymerase was added and the reaction allowed to cycle repeatedly between 55° C. (30 seconds), 72° C. (30 seconds), and 95° C. (30 seconds). After 20 cycles, the DNA was removed and purified by electrophoresis through 2% agarose gels. The band at approximately 174 base pairs was electroeluted from the gel, ethanol precipitated, and digested with NheI and BamHI endonucleases. The resulting fragment was ligated into a vector containing the construct illustrated in FIG. 1 at the NheI and BamHI sites. Similarly, oligonucleotides 1006 and 1007 (shown in the positions that they hybridize) were mixed and heated to 95° C. for 2 minutes. Vent DNA polymerase (New England Biolabs) was added and the reaction allowed to cool slowly to 68° C. and maintained at that temperature for 5 min to permit the fill-in reaction to occur. An aliquot of the reaction was added to a second tube containing primers 1008 and 1009 and the tube was heated to 95° C. for 2 minutes. Vent DNA polymerase was added and the reaction allowed to cycle repeatedly between 55° C. (30 seconds), 72° C. (30 seconds), and 95° C. (30 seconds). After 20 cycles, the DNA was removed and purified by electrophoresis through 2% agarose gels. The band at approximately 174 base pairs was electroeluted from the gel, ethanol precipitated, and digested with NheI and BamHI endonucleases. The resulting fragment was ligated into a vector containing the construct illustrated in FIG. 1 at the NheI and BamHI sites. Use of the other oligonucleotides is described in the Examples.

FIG. 5 shows the coding sequence of the entire Fos-hCG-α-subunit construct. It should be noted that it differs from the native hCG α-subunit by the presence of the hCG β-subunit leader sequence, the presence of the Fos sequence, and the lack of 4 α-subunit amino acids, namely Ala1-Pro2-Asp3-Val4(SEQ ID NO:53). These residues were omitted to facilitate formation of the heterodimer. However, it is possible to retain these residues by inserting a linker between the Fos and α-subunit coding regions. When this linker contains a protease cleavage recognition site (e.g., amino acids arginine-serine-lysine-arginine) and when a similar protease cleavage recognition site is introduced between the Jun sequence and the β-subunit construct described later, the heterodimer that is created will lack its Fos sequence at the N-terminus.

FIG. 6 shows the coding sequence of the entire Jun-hCGβ'-subunit construct. It should be noted that it differs from the native hCG β-subunit by the presence of the Jun sequence and the lack of 6 β-subunit amino acids, namely Ser1-Lys2-Glu3-Pro4-Leu5-Arg6(SEQ ID NO:54). These residues were omitted to facilitate formation of the heterodimer. However, it is possible to retain these residues by inserting a linker between the Jun and β-subunit coding regions. When this linker contains a protease cleavage recognition site and when a similar protease cleavage recognition site is introduced between the Fos sequence and the α-subunit construct described earlier, the heterodimer that is created will lack its Jun sequence at the N-terminus.

FIG. 7 shows that the heterodimer containing the Fos-Jun amino acid sequences at its N-termini can stimulate signal transduction in a similar fashion as hCG. Signal transduction (production of cyclic AMP) was monitored using CHO cells that express rat LH receptors as described (33).

Figure 8:
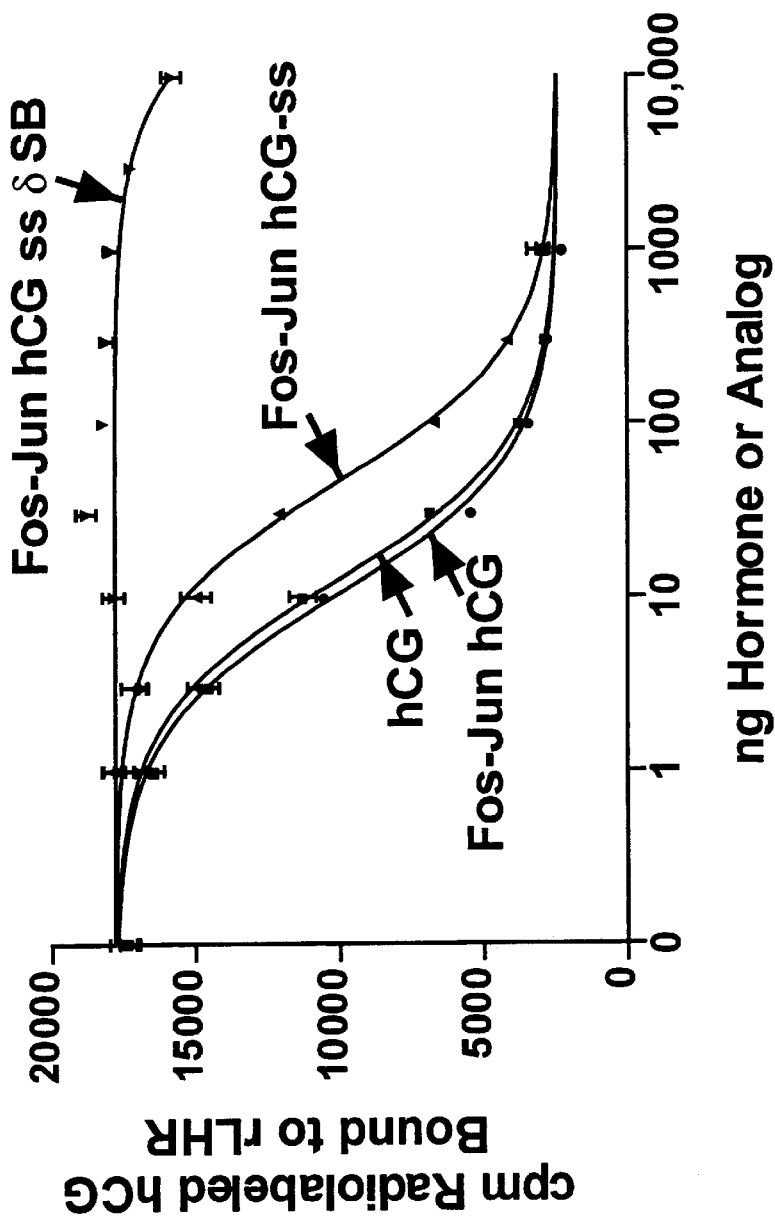
FIG. 8 shows that the heterodimer containing the Fos-Jun amino acid sequences at its N-termini can inhibit the binding of radioiodinated hCG to CHO cells expressing rat LH receptors in a similar fashion as hCG.

FIG. 8 shows that the heterodimer containing the Fos-Jun amino acid sequences at its N-termini can inhibit the binding of radioiodinated hCG to CHO cells expressing rat LH receptors in a similar fashion as hCG. Receptor binding was monitored by inhibiting the binding of radioiodinated hCG to cells expressing LH receptors as described (33).

FIG. 9 illustrates the sequence of an α-subunit construct that is lacking the glycosylation signal normally found at Asn52 of the mature human α-subunit. This construct can be prepared by anyone skilled in the art of DNA mutagenesis by using polymerase chain reaction or other mutagenesis to introduce BglII and SpeI endonuclease restriction sites into the cDNA for the human α-subunit. This will permit making of the construct illustrated here by cassette mutagenesis between the BglII and SpeI sites. Elimination of the glycosylation signal is illustrated here by replacing the codon for Asn52 with that of Asp. Constructs with this mutation are known to have reduced efficacy for LH receptors (10). However, it is not essential that this specific mutation be prepared to eliminate the oligosaccharide at this location.

FIG. 10 illustrates the sequence of the Fos-α-subunit construct that is lacking the glycosylation signal corresponding to human α-subunit residue 52 caused by substitution of an aspartic acid residue for the asparagine normally found at this residue of the human α-subunit. Unlike human α-subunit that has been deglycosylated by this mutation that combines with hCG β-subunit poorly, the construct shown here combines well with the Jun-hCGβ'-subunit to form a heterodimer that binds to LH receptors.

FIG. 11 illustrates the sequence of the Fos-α-subunit construct in which the cysteine normally found at position 7 of the human α-subunit has been replaced by an alanine. When expressed with the Jun-hCGβ'-subunit construct shown in FIG. 12, this will cause the formation of an intersubunit disulfide between residues of the cysteine knots.

FIG. 12 illustrates the sequence of the Jun-hCGβ'-subunit in which the tyrosine normally found in the hCG β-subunit at residue 37 has been replaced by a cysteine. When expressed with the construct illustrated in FIG. 11, the heterodimer that is formed will have an intersubunit between residues of its cysteine knots.

FIG. 13 illustrates the Jun-hCGβ'-Y37C-C26A construct. This construct is similar to that in FIG. 12 except that the codon for cysteine normally found at residue 26 in the hCG β-subunit has been changed to alanine. This will prevent closure of the seatbelt. Expression of this construct along with the construct illustrated in FIG. 11 was shown to cause the formation of a heterodimer even though the heterodimer is unable to latch the seatbelt loop.

FIG. 14 illustrates the Jun-hCGβ'-Y37C-C26A-δ92 construct. This construct is similar to that in FIG. 13 except that the codons for all hCG β-subunit seatbelt residues except 91 and 92 are missing. This construct is also missing the residues in the C-terminus normally found in the hCG β-subunit. Expression of this construct along with the construct illustrated in FIG. 11 was shown to cause the formation of a heterodimer even though the heterodimer lacked the seatbelt loop.

Figure 15:
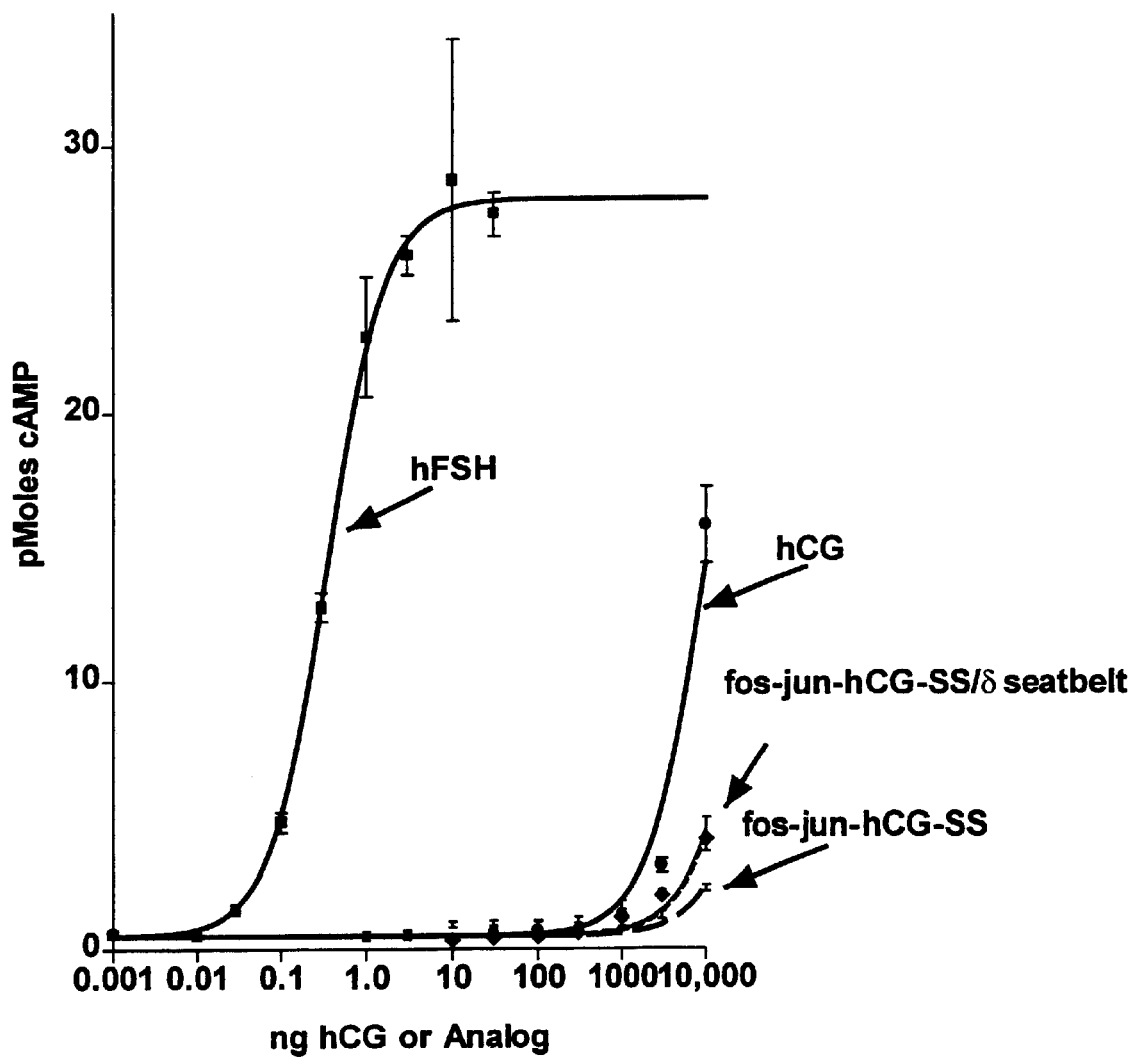
FIG. 15 illustrates the abilities of hFSH, hCG, Fos-Jun-hCG-SS/δseatbelt, and Fos-Jun-hCG-SS to stimulate signal transduction in CHO cells expressing human FSH receptors.
Figure 16:
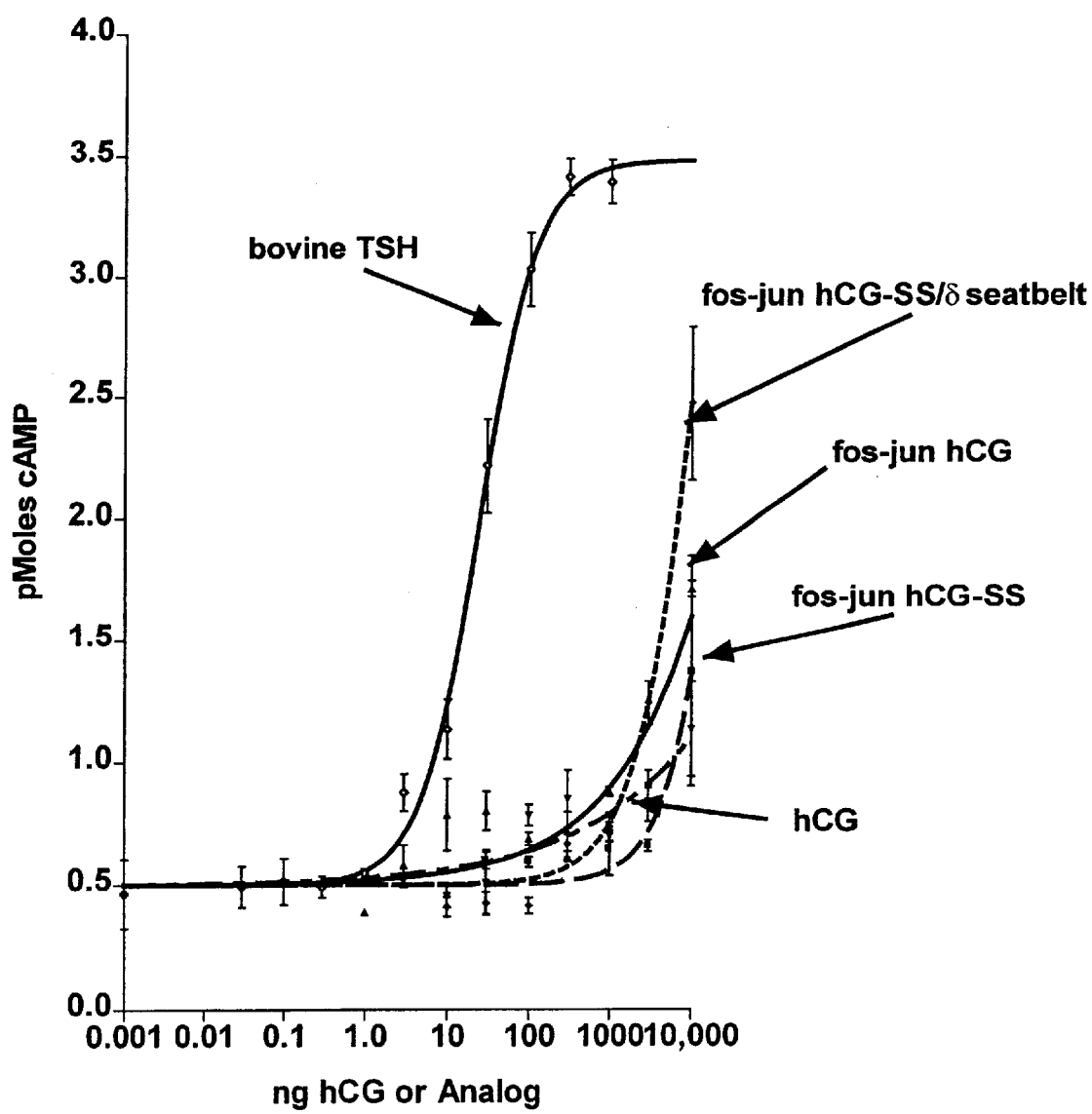
FIG. 16 illustrates the abilities of bovine TSH, hCG, Fos-Jun-hCG-SeS/δseatbelt, and Fos-Jun-hCG-SS to stimulate signal transduction in CHO cells expressing human FSH receptors.

FIG. 15 illustrates the abilities of hFSH, hCG, Fos-Jun-hCG-SS/δseatbelt, and Fos-Jun-hCG-SS to stimulate signal transduction in CHO cells expressing human FSH receptors. This shows that hCG is much less potent than hFSH as expected. However, the absence of the seatbelt causes only a small additional influence on the activity of hCG.

FIG. 16 illustrates the abilities of bovine TSH, hCG, Fos-Jun-hCG-SS/δseatbelt, and Fos-Jun-hCG-SS to stimulate signal transduction in CHO cells expressing human FSH receptors. This shows that hCG is much less potent than TSH as expected. However, the absence of the seatbelt causes only a small additional influence on the activity of hCG.

FIG. 17 illustrates the sequences of constructs of Fos-hCG α-subunit containing a furin cleavage site and the sequences of Jun-hCG β-subunit, Jun-hLH β-subunit, Jun-hFSH β-subunit, Jun-hTSH β-subunit, Jun-hCG/hFSH β-subunit chimera, and Jun-hCG/hTSH β-subunit chimera containing a furin cleavage site. Expression of the α-subunit constructs with the β-subunit constructs is expected to lead to the formation of α/β heterodimers similar to the formation of Fos-Jun-hCG and analogs of Fos-Jun-hCG. Following subunit combination in the lumen of the endoplasmic reticulum, the Fos and Jun dimerization domains are expected to be removed during passage of the heterodimer through the Golgi apparatus and trans-Golgi network as it is being readied for secretion. These constructs can be prepared following the steps used to prepare Fos-α and Jun-β except that the codons for the amino acids in a furin cleavage site (e.g., KSKR) are inserted into the oligonucleotides used to encode the Fos and Jun sequences (i.e., the sequences illustrated in FIG. 3 and FIG. 7). The internal hyphens are included to facilitate identification of the portions of the molecule that correspond to the hCG β-subunit leader, Fos or Jun dimerization domains, furin cleavage signal, and mature protein. The hyphens at the ends of the lines indicate that the sequence continues uninterrupted on the next line.

FIG. 18 illustrates the sequences of constructs containing immunoglobulin dimerization domains at their N-termini. When the α-subunit construct and a β-subunit construct are expressed in the same cell, an α/β heterodimer will be formed. When the furin cleavage site is present as illustrated in these sequences, the immunoglobulin domains will be removed. Inclusion of the furin cleavage site in only the α- or β-construct is expected to create a dimer that is held to the immunoglobulin domains through bonds to one subunit.

FIG. 19 illustrates the sequences of constructs containing immunoglobulin dimerization domains at their N-termini. Unlike those in FIG. 18, these immunoglobulin dimerization domains will not form an intersubunit disulfide.

FIG. 20 illustrates the amino acid sequences of β-subunit constructs containing the dimerization domain from Jun at the carboxyterminus of their dimerization domains. As noted, some of these have the ability to form a disulfide crosslink between the two subunits.

Throughout this application, various publications have been referenced. The disclosures in these publications are incorporated herein by reference in order to more fully describe the state of the art.

APPENDIX OF REFERENCES

1. Pierce, J. G. and T. F. Parsons. 1981. Glycoprotein hormones: structure and function. Ann.Rev.Biochem. 50:465–495.
2. Moyle, W. R. and R. K. Campbell. 1995. Gonadotropins. In Reproductive endocrinology, surgery, and technology. E. Y. Adashi, J. A. Rock, and Z. Rosenwaks, editors. Lippincott-Raven, Philadelphia. 683–724.
3. Moyle, W. R. and R. K. Campbell. 1995. The Gonadotropins. In Endocrinology. L. J. DeGroot, editor. Saunders, Philadelphia. 230–241.
4. Yen, S. S. C. and R. B. Jaffe. 1986. Reproductive Endocrinology: Physiology, Pathophysiology and Clinical Management. W. B.Saunders, Philadelphia.
5. Adashi, E. Y., J. A. Rock, and Z. Rosenwaks. 1996. Reproductive endocrinology, surgery, and technology. Lippincott-Raven, Philadelphia. 5 pp.
6. DeGroot, L. J. 1995. Endocrinology. W.B.Saunders Company, Philadelphia. 3 pp.
7. Anonymous. 1988. Office of Technology Assessment: Report Brief—Infertility: Medical and Social Choices. Washington, D.C.: OTA, US Congress.
8. Anonymous. 1989. Institute of Medicine and National Research Council, Medically Assisted Conception: an agenda for research. Washington, D.C.: National Academy Press.
9. Moyle, W. R., O. P. Bahl, and L. Marz. 1975. Role of the carbohydrate of human choriogonadotropin in the mechanism of hormone action. J.Biol.Chem. 250:9163–9169.
10. Matzuk, M. M., J. L. Keene, and I. Boime. 1989. Site specificity of the chorionic gonadotropin N-linked oligosaccharides in signal transduction. J.Biol.Chem. 264:2409–2414.
11. Morell, A. G., G. Gregoriadis, I. H. Scheinberg, J. Hickman, and G. Ashwell. 1971. The role of sialic acid in determining the survival of glycoproteins in the circulation. J.Biol.Chem. 246:1461–1467.
12. Baenziger, J. U. and E. D. Green. 1988. Pituitary glycoprotein hormone oligosaccharides: structure, synthesis and function of the asparagine-linked oligosaccharides on lutropin, follitropin and thyrotropin. Biochim .Biophys.Acta. 947:287–306.
13. Fiete, D., V. Srivastava, O. Hindsgaul, and J. U. Baenziger. 1991. A hepatic reticuloendothelial cell receptor specific for SO4-4GalNAc (1,4GlcNAc (1,2Man(that mediates rapid clearance of lutropin. Cell 67:1103–1110.
14. Matzuk, M. M. and I. Boime. 1988. Site-specific mutagenesis defines the intracellular role of the asparagine-linked oligosaccharides of chorionic gonadotropin (-subunit. J.Biol.Chem. 263:17106–17111.
15. Matzuk, M. M. and I. Boime. 1988. The role of the asparagine-linked oligosaccharides of the (-subunit in the secretion and assembly of human chorionic gonadotrophin. J.Cell.Biol. 106:1049–1059.
16. Matzuk, M. M. and I. Boime. 1989. Mutagenesis and gene transfer define site-specific roles of the gonadotropin oligosaccharides. Biol.Reprod. 40:48–53.
17. Fiddes, J. C. and K. Talmadge. 1984. Structure, Expression, and Evolution of the genes for the human glycoprotein hormones. In Recent Progress in Hormone Research. Vol 40. R. O. Greep, editor. Academic Press, New York. 43–78.
18. Talmadge, K., N. C. Vamvakopoulos, and J. C. Fiddes. 1984. Evolution of the genes for the beta subunits of human chorionic gonadotropin and luteinizing hormone. Nature 307:37–40.
19. Fiddes, J. C. and H. M. Goodman. 1979. Isolation cloning and sequence analysis of the cDNA for the (-subunit of human chorionic gonadotropin. Nature. 281:351–356.
20. Fiddes, J. C. and H. M. Goodman. 1980. The cDNA for the (-subunit of human chorionic gonadotropin suggests 20. evolution of a gene by readthrough into the 3'-untranslated region. Nature. 286:684–687.
21. Fiddes, J. C. and H. M. Goodman. 1981. The gene encoding the common alpha subunit of the four human glycoprotein hormones. J.Mol.Appl.Genet. 1:3–18.
22. Lapthorn, A. J., D. C. Harris, A. Littlejohn, J. W. Lustbader, R. E. Canfield, K. J. Machin, F. J. Morgan, and N. W. Isaacs. 1994. Crystal structure of human chorionic gonadotropin. Nature 369:455–461.
23. Wu, H., J. W. Lustbader, Y. Liu, R. E. Canfield, and W. A. Hendrickson. 1994. Structure of human chorionic gonadotropin at 2.6Å resolution from MAD analysis of the selenomethionyl protein. Structure 2:545–558.
24. Sun, P. D. and D. R. Davies. 1995. The cysteine-knot growth-factor superfamily. Annu.Rev.Biophys.Biomol.Struct. 24:269–291.
25. Ruddon, R. W., S. A. Sherman, and E. Bedows. 1996. Protein folding in the endoplasmic reticulum: lessons from the human chorionic gonadotropin (-subunit. Prot.Sci. 8:1443–1452.
26. Keutmann, H. T., M. C. Charlesworth, K. A. Mason, T. Ostrea, L. Johnson, and R. J. Ryan. 1987. A receptor-binding region in human choriogonadotropin/lutropin beta subunit. Proc.Natl.Acad.Sci.USA 84:2038–2042.
27. Santa Coloma, T. A., B. Dattatreyamurty, and L. E. Reichert, Jr. 1990. A synthetic peptide corresponding to human FSH ?-subunit 33–53 binds to FSH receptor stimulates basal estradiol synthesis and is a partial antagonist of FSH. Biochemistry. 29:1194–1200.
28. Santa Coloma, T. A. and L. E. Reichert, Jr. 1990. Identification of a follicle-stimulating hormone receptor-binding region in hFSH-(81–95) using synthetic peptides. J.Biol.Chem. 265:5037–5042.
29. Schneyer, A. L., P. M. Sluss, J. S. Huston, R. J. Ridge, and L. E. Reichert, Jr. 1988. Identification of a receptor binding region on the ?-subunit of human follicle-stimulating hormone. Biochemistry. 27:666–671.
30. Reddy, V. B., A. K. Beck, A. J. Garramone, V. Vellucci, J. Lustbader, and E. G. Bernstein. 1985. Expression of human choriogonadotropin in monkey cells using a single simian virus 40 vector. Proc.Natl.Acad.Sci.USA 82:3644–3648.
31. Campbell, R. K., D. M. Dean Emig, and W. R. Moyle. 1991. Conversion of human choriogonadotropin into a follitropin by protein engineering. Proc.Natl.Acad.Sci.USA 88:760–764.
32. Moyle, W. R., M. M. Matzuk, R. K. Campbell, E. Cogliani, D. M. Dean Emig, A. Krichevsky, R. W. Barnett, and I. Boime. 1990. Localization of residues that confer antibody binding specificity using human chorionic gonadotropin/luteinizing hormone beta subunit chimeras and mutants. J.Biol.Chem. 265:8511–8518.
33. Moyle, W. R., R. K. Campbell, R. V. Myers, M. P. Bernard, Y. Han, and X. Wang. 1994. Co-evolution of ligand-receptor pairs. Nature 368:251–255.
34. Matzuk, M. M., M. Krieger, C. L. Corless, and I. Boime. 1987. Effects of preventing β-glycosylation on the secretion of human chorionic gonadotropin in Chinese hamster ovary cells. Proc.Natl.Acad.Sci.USA 84:6354–6358.
35. Matzuk, M. M., C. M. Kornmeier, G. K. Whitfield, I. A. Kourides, and I. Boime. 1988. The glycoprotein (-subunit is critical for secretion and stability of the human thyrotropin (-subunit [published erratum appears in Mol Endocrinol 1988:713]. Mol.Endocrinol. 2:95–100.
36. Kaetzel, D. M., J. K. Browne, F. Wondisford, T. M. Nett, A. R. Thomason, and J. H. Nilson. 1985. Expression of biologically active bovine luteinizing hormone in Chinese hamster ovary cells. Proc.Natl.Acad.Sci.USA 82:7280–7283.
37. Kaetzel, D. M. and J. H. Nilson. 1988. Methotrexate-induced amplification of the bovine lutropin genes in Chinese hamster ovary cells. Relative concentration of the alpha and beta subunits determines the extent of heterodimer assembly. Journal of Biological Chemistry 263:6344–6351.
38. Maniatis, T., E. F. Fritsch, and J. Sambrook. 1989. Molecular cloning: a laboratory manual. Cold Spring Harbor Laboratory, Cold Spring Harbor, N.Y.
39. Ausubel, F. M., R. Brent, R. E. Kingston, R. E. Moore, J. G. Seidman, J. A. Smith, and K. Struhl. 1987. Current protocols in molecular biology. Green Publishing Associates and Wiley-Interscience, New York.
40. Kriegler, M. 1990. Gene Transfer and Expression: A Laboratory Manual. Stockton Press, New York.
41. Moyle, W. R., P. H. Ehrlich, and R. E. Canfield. 1982. Use of monoclonal antibodies to hCG subunits to examine the orientation of hCG in the hormone-receptor complex. Proc.Natl.Acad.Sci.USA 79:2245–2249.
42. Slaughter, S., Y. H. Wang, R. V. Myers, and W. R. Moyle. 1995. The lutropin (-subunit N-terminus facilitates subunit combination by offsetting the inhibitory effects of residues needed for LH activity. Mol.Cell.Endocrinol. 112:21–25.
43. Keutmann, H. T. and D. A. Rubin. 1993. A subunit interaction site in human luteinizing hormone: identification by photoaffinity cross-linking. Endocrinology 132:1305–1312.
44. Sugahara, T., M. R. Pixley, S. Minami, E. Perlas, D. Ben-Menahem, A. J. W. Hsueh, and I. Boime. 1995. Biosynthesis of a biologically active single peptide chain containing the human common (and chorionic gonadotropin (subunits in tandem. Proc.Natl.Acad.Sci.USA 92:2041–2045.
45. Cosowsky, L., S. N. V. Rao, G .J. Macdonald, H. Papkoff, R. K. Campbell, and W. R. Moyle. 1995. The groove between the (-and (-subunits of hormones with lutropin (LH) activity appears to contact the LH receptor and its conformation is changed during hormone binding. J.Biol.Chem. 270:20011–20019.
46. Moyle, W. R., R. K. Campbell, S. N. V. Rao, N. G. Ayad, M. P. Bernard, Y. Han, and Y. Wang. 1995. Model of human chorionic gonadotropin (hCG) and lutropin receptor (LHR) interaction that explains signal transduction of the glycoprotein hormones. J. Biol. Chem. 270:20020–20031.
47. Cosowsky, L., W. Lin, Y. Han, M.β. Bernard, R. K. Campbell, and W. R. Moyle. 1997. Influence of subunit interactions on lutropin specificity: implications for studies of glycoprotein hormone function. J.Biol.Chem. 272:3309–3314.
48. Han, Y., M.β. Bernard, and W. R. Moyle. 1996. hCG? Residues 94–96 alter LH activity without appearing to make key receptor contacts. Mol.Cell.Endocrinol. 124:151–161.
49. Suganuma, N., M. M. Matzuk, and I. Boime. 1989. Elimination of disulfide bonds affects assembly and secretion of the human chorionic gonadotropin beta subunit. J.Biol.Chem. 264:19302–19307.
50. Campbell, R. K., E. R. Bergert, Y. Wang, J. C. Morris, and W. R. Moyle. 1997. Chimeric proteins can exceed the sum of their parts: implications for evolution and protein design. Nature Biotech. 15:439–443.

51. Berger, B., D. B. Wilson, E. Wolf, T. Tonchev, M. Milla, and P. S. Kim. 1995. Predicting coiled coils by use of pairwise residue correlations. Proc.Natl.Acad.Sci.USA 92:8259–8263.
52. Fares, F. A., N. Suganuma, K. Nishimori, P. S. LaPolt, A. J. Hsueh, and I. Boime. 1992. Design of a long-acting follitropin agonist by fusing the C-terminal sequence of the chorionic gonadotropin beta subunit to the follitropin beta subunit. Proc.Natl.Acad.Sci.USA 89:4304–4308.

The invention being thus described, it will be obvious that the same may be varied in many ways. Such variations are not to be regarded as a departure from the spirit and scope of the invention and all such modifications are intended to be included within the scope of the following claims.

---

I claim:

1. A method for forming a subunit combination of a cysteine knot glycoprotein hormone having an α-subunit and a β-subunit to prepare a heterodimeric protein analog which comprises the steps of:
   (a) attaching a dimerization domain to the amino termini of both an α-subunit and a β-subunit of a cysteine knot glycoprotein hormone; and
   (b) dimerizing the α-subunit and β-subunit to form a heterodimeric protein analog.

2. The method according to claim 1, wherein a Fos dimerization sequence domain is attached to the amino-terminus of the β-subunit and a Jun dimerization sequence domain is attached to the amino-terminus of the α-subunit.

3. The method according to claim 1, wherein a Fos dimerization sequence domain is attached to the amino-terminus of the α-subunit and a Jun dimerization sequence domain is attached to the amino-terminus of the β-subunit.

4. The method according to claim 2, wherein a glycine or serine residue is inserted between the Fos or Jun dimerization sequence domain and a furin cleavage site to facilitate cleavage of the dimerization sequence domain from the heterodimer.

5. The method according to claim 3, wherein a glycine or serine residue is inserted between the Fos or Jun dimerization sequence domain and a furin cleavage site to facilitate cleavage of the dimerization sequence domain from the heterodimer.

6. The method according to claim 1, wherein the heterodimeric protein analog is selected from the group consisting of hCG/hFSH chimeras, hCG/hTSH chimeras, deglycosylated hormones, truncated glycoprotein hormones, mutant glycoprotein hormones, and glycoprotein hormones containing an hCG carboxyl terminus.

7. The method according to claim 1, further comprising incorporating protease cleavage sites between additional N-terminal sequences and the α-subunit and the β-subunit of the cysteine knot protein to remove the dimerization domains from the heterodimeric protein analog.

8. The method according to claim 1, wherein the cysteine knot glycoprotein hormone has an oligosaccharide genetically removed from the α-subunit at Asn52.

9. The method according to claim 1, wherein the cysteine knot glycoprotein hormone lacks a seatbelt.

10. A method for forming a subunit combination of a cysteine knot glycoprotein hormone having an α-subunit and a β-subunit to prepare a heterodimeric protein analog which comprises the steps of:
    (a) attaching a dimerization domain to the amino terminus of an α-subunit and the carboxy terminus of a β-subunit of a cysteine knot glycoprotein hormone; and
    (b) dimerizing the α-subunit and β-subunit to form a heterodimeric protein analog.

11. The method according to claim 10, wherein a Fos dimerization sequence domain is attached to the carboxy-terminus of the β-subunit and a Jun dimerization sequence domain is attached to the amino-terminus of the α-subunit.

12. The method according to claim 10, wherein a Fos dimerization sequence domain is attached to the amino-terminus of the α-subunit and a Jun dimerization sequence domain is attached to the carboxy terminus of the β-subunit.

13. The method according to claim 11, wherein a protease cleavage site is inserted between the dimerization sequence domain and the α-subunit and a protease cleavage site is inserted between the dimerization sequence domain and the β-subunit.

14. The method according to claim 13, wherein the protease cleavage site is furin.

15. The method according to claim 10, wherein the heterodimeric protein analog is selected from the group consisting of hCG/hFSH chimeras, hCG/hTSH chimeras, deglycosylated hormones, truncated glycoprotein hormones, mutant glycoprotein hormones, and glycoprotein hormones containing an hCG carboxyl terminus.

16. The method according to claim 10, wherein the cysteine knot glycoprotein hormone has an oligosaccharide genetically removed from the α-subunit at Asn52.

17. The method according to claim 1, wherein a Fos dimerization sequence domain is attached to the amino-terminus of an hCG β-subunit and a Jun dimerization sequence domain is attached to the amino-terminus of an hFSH α-subunit.

18. The method according to claim 10, wherein a Fos dimerization sequence domain is attached to the carboxy-terminus of an hCG β-subunit and a Jun dimerization sequence domain is attached to the amino-terminus of an hFSH α-subunit.

* * * * *